(12) United States Patent
Numata et al.

(10) Patent No.: US 9,266,865 B2
(45) Date of Patent: Feb. 23, 2016

(54) MATERIAL FOR ORGANIC ELECTROLUMINESCENT ELEMENT, AND ORGANIC ELECTROLUMINESCENT ELEMENT USING SAME

(75) Inventors: Masaki Numata, Sodegaura (JP); Hideaki Nagashima, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 740 days.

(21) Appl. No.: 13/637,988

(22) PCT Filed: Mar. 29, 2011

(86) PCT No.: PCT/JP2011/057905
§ 371 (c)(1),
(2), (4) Date: Sep. 28, 2012

(87) PCT Pub. No.: WO2011/125680
PCT Pub. Date: Oct. 13, 2011

(65) Prior Publication Data
US 2013/0020565 A1    Jan. 24, 2013

(30) Foreign Application Priority Data

Mar. 31, 2010  (JP) ................................ 2010-084476

(51) Int. Cl.
| | |
|---|---|
| *C07D 409/14* | (2006.01) |
| *C07D 403/14* | (2006.01) |
| *C07D 405/14* | (2006.01) |
| *C07D 209/86* | (2006.01) |
| *C07D 403/10* | (2006.01) |
| *C07D 405/04* | (2006.01) |
| *C09K 11/06* | (2006.01) |
| *H05B 33/14* | (2006.01) |
| *H05B 33/20* | (2006.01) |
| *H01L 51/00* | (2006.01) |
| *H01L 51/50* | (2006.01) |

(52) U.S. Cl.
CPC ............ *C07D 405/14* (2013.01); *C07D 209/86* (2013.01); *C07D 403/10* (2013.01); *C07D 405/04* (2013.01); *C09K 11/06* (2013.01); *H01L 51/0062* (2013.01); *H05B 33/14* (2013.01); *H05B 33/20* (2013.01); *C09K 2211/1029* (2013.01); *C09K 2211/1044* (2013.01); *C09K 2211/1059* (2013.01); *C09K 2211/1074* (2013.01); *C09K 2211/1092* (2013.01); *C09K 2211/185* (2013.01); *H01L 51/0072* (2013.01); *H01L 51/0074* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 2008/0191618 A1 | 8/2008 | Mishima | |
| 2008/0238305 A1 | 10/2008 | Kondo et al. | |
| 2009/0302745 A1 | 12/2009 | Otsu et al. | |
| 2010/0207515 A1 | 8/2010 | Moyama | |
| 2011/0260138 A1* | 10/2011 | Xia et al. | 257/40 |

FOREIGN PATENT DOCUMENTS

| | | |
|---|---|---|
| JP | 9 3448 | 1/1997 |
| JP | 2000 173774 | 6/2000 |
| JP | 2004 311413 | 11/2004 |
| JP | 2008-84913 A | 4/2008 |
| JP | 2008-523049 A | 7/2008 |
| JP | 2008 227462 | 9/2008 |
| JP | 2009 84622 | 4/2009 |
| JP | 2009 94124 | 4/2009 |
| JP | 2010 21336 | 1/2010 |
| JP | 2010 40830 | 2/2010 |
| WO | 2007 077810 | 7/2007 |
| WO | 2007 108459 | 9/2007 |
| WO | 2007 119816 | 10/2007 |
| WO | WO 2008/029652 A1 | 3/2008 |
| WO | WO 2008/029729 A1 | 3/2008 |
| WO | 2010 004877 | 1/2010 |

OTHER PUBLICATIONS

Machine translation of WO 2010/004877. Date of publication: Jan. 14, 2010.*
U.S. Appl. No. 13/638,317, filed Sep. 28, 2012, Numata, et al.
Japanese Office Action Issued Feb. 5, 2013 in Patent Application No. 2012-508130.
Japanese Office Action issued Apr. 22, 2014, in Japan Patent Application No. 2013-094610.
Extended European Search Report issued Aug. 21, 2013, in European Patent Application No. 11765580.3.
Vaitkeviciene, V., et al., "Well-defined [3,3']bicarbazolyl-based electroactive compounds for optoelectronics," Synthetic Metals, vol. 158, pp. 383-390, (2008).

(Continued)

*Primary Examiner* — Andrew K Bohaty

(74) *Attorney, Agent, or Firm* — Oblon, McClelland, Maier & Neustadt, L.L.P.

(57) ABSTRACT

Provided is a material for an organic electroluminescence device having a specific structure in which a dibenzothiophenyl group or a carbazolyl group is bonded to a carbazolyl group at its N-position (9-position) directly or through a linking group. Further provided is an organic electroluminescence device including one or more organic thin film layers including a light emitting layer between a cathode and an anode, in which at least one organic thin film layer contains the material for an organic electroluminescence device of the present invention.

26 Claims, No Drawings

(56) References Cited

OTHER PUBLICATIONS

Baldo, M.A., et al., "Very high-efficiency green organic light-emitting devices based on electrophosphorescence," Applied Physics Letters, vol. 75, No. 1, pp. 4-6 (Jul. 5, 1999).

O'Brien, D.F., et al., "Improved energy transfer in electrophosphorescent devices," Applied Physics Letters, vol. 74, No. 3, pp. 442-444, (Jan. 18, 1999).

International Search Report Issued Jul. 5, 2011 in PCT/JP11/57905 Filed Mar. 29, 2011.

* cited by examiner

MATERIAL FOR ORGANIC ELECTROLUMINESCENT ELEMENT, AND ORGANIC ELECTROLUMINESCENT ELEMENT USING SAME

CROSS REFERENCE TO RELATED APPLICATIONS

This application is a 371 of PCT/JP11/57905, filed Mar. 29, 2011, the disclosure of which is incorporated herein by reference in its entirety. Priority to Japanese patent application 2010-084476, filed Mar. 31, 2010, the disclosure of which is incorporated herein by reference in its entirety.

TECHNICAL FIELD

The present invention relates to a material for an organic electroluminescence device and an organic electroluminescence device using the material.

BACKGROUND ART

An organic electroluminescence device (hereinafter, "electroluminescence" may be abbreviated as "EL") is a spontaneous light emitting device which utilizes the principle that a fluorescent substance or a phosphorescent substance emits light by energy of recombination of holes injected from an anode and electrons injected from a cathode when an electric field is applied. Since an organic EL device of the laminate type driven under a low electric voltage was reported, many studies have been conducted on organic EL devices using organic materials as the constituent materials. The devices of the laminate type use tris(8-quinolinolato) aluminum for a light emitting layer and a triphenyldiamine derivative for a hole transporting layer. Advantages of the laminate structure are that the efficiency of hole injection into the light emitting layer can be increased, that the efficiency of forming exciton which are formed by blocking and recombining electrons injected from the cathode can be increased, and that exciton formed within the light emitting layer can be enclosed. As described above, for the structure of the organic EL device, a two-layered structure having a hole transporting (injecting) layer and an electron transporting light emitting layer and a three-layered structure having a hole transporting (injecting) layer, a light emitting layer, and an electron transporting (injecting) layer are well known. To increase the efficiency of recombination of injected holes and electrons in the devices of the laminate type, the structure of the device and the process for forming the device have been studied.

As the light emitting material of the organic EL device, a metal complex such as a tris(8-quinolinolato) aluminum complex, a coumarine derivative, a tetraphenylbutadiene derivative, a distyrylarylene derivative, and an oxadiazole derivative are known. It is reported that light emission ranging from blue light to red light in the visible light region can be obtained by using those light emitting materials, and a device exhibiting color images was realized.

A fluorescent light emitting material that emits light by means of a singlet exciton has been conventionally used as a light emitting material for an organic EL device. In recent years, the utilization of a phosphorescent light emitting material that emits light by means of a triplet exciton as well as the fluorescent light emitting material has also been proposed (for example, Non Patent Literature 1 and Non Patent Literature 2). An organic EL device using the phosphorescent light emitting material can achieve luminous efficiency three to four times as high as that of an organic EL device using only the fluorescent light emitting material because it is assumed that singlet excitons and triplet excitons are produced at a ratio of 1:3 upon recombination of electrons and holes in an organic EL device by virtue of a difference in spin multiplicity. In blue phosphorescent light emission, however, high efficiency and a long lifetime are hard to achieve, and hence the development of a host material that achieves the high efficiency and the long lifetime has been desired.

Patent Literature 1 proposes a compound in which two carbazole skeletons are bonded to each other through a linking group. Patent Literature 2 describes a compound in which two carbazole skeletons are bonded to one dibenzothiophene skeleton (for example, Compound 24). Patent Literature 3 describes a compound in which two carbazole skeletons and two dibenzothiophene skeletons are combined with one another (for example, Compound 21).

However, none of those literatures describes a compound having two carbazole skeletons bonded to each other through a linking group as required in which a dibenzothiophene skeleton or a carbazole skeleton is bonded to at least one of the carbazole skeletons at its N-position through a linking group as required.

Patent Literature 4 describes a compound (H-12) in which two carbazole skeletons are bonded to each other through an m-phenylene linking group and each of the carbazole skeletons is substituted at its N-position with a dibenzothiophene skeleton through an m-phenylene linking group.

However, the compound has a large molecular weight and is considered to have a large intermolecular force because its molecular skeleton is linear (one-dimensional). Accordingly, it is assumed that the compound has low sublimation property and hence requires a high temperature in its sublimation step or vapor deposition step, with the result that the step involves its thermal decomposition. Therefore, the compound is considered to be unsuitable as a material to be used in an organic EL device produced by employing a sublimation step or a vapor deposition step.

In addition, Patent Literature 4 intends to provide, for example, an organic EL device showing a small number of dark spots, a small leak current, and small light emission unevenness in the light emitting device. The literature does not reveal whether the organic EL device emits phosphorescence with high efficiency at a low driving voltage.

Further, Non Patent Literature 3 describes a compound (Compound 8) having two carbazole skeletons in which each of the carbazole skeletons is further substituted at its N-position with a carbazole skeleton at its 3-position. However, the compound has a low glass transition temperature because the compound has a long-chain alkyl group. In addition, it is assumed that owing to its molecular weight and an effect of the entanglement of its long-chain alkyl groups, the compound has low sublimation property and hence requires a high temperature in its sublimation step or vapor deposition step, with the result that the step involves its thermal decomposition. Therefore, the compound is considered to be unsuitable as a material to be used in an organic EL device produced by employing a sublimation step or a vapor deposition step.

In addition, a blue phosphorescent light emitting device using any one of the compounds described in Patent Literatures 1 to 3 has had an insufficiently low driving voltage, insufficiently high efficiency, and an insufficiently long lifetime.

CITATION LIST

Patent Literature

[PTL 1] WO 2007/108459 A1
[PTL 2] WO 2007/119816 A1
[PTL 3] WO 2007/077810 A1
[PTL 4] WO 2010/004877 A1

Non Patent Literature

[NPL 1] Applied Physics letters Vol. 74 No. 3, p 442-444
[NPL 2] Applied Physics letters Vol. 75 No. 1, p 4-6
[NPL 3] Synthetic Metals (2008), Vol. 158, p 383-390

SUMMARY OF INVENTION

Technical Problem

The present invention has been made to solve the problems, and an object of the present invention is to provide an organic EL device that emits phosphorescence at a low driving voltage, and has high efficiency and a long lifetime, and a material for an organic electroluminescence device for realizing the device.

Solution to Problem

The inventors of the present invention have made extensive studies to achieve the object, and as a result, have found that when a compound of such a construction as represented by the following formula (1) is used as a material for an organic EL device, the device can emit phosphorescence at a low driving voltage with high efficiency, and can have a lengthened lifetime by reasons to be described later. Thus, the inventors have reached the present invention.

That is, the present invention provides a material for an organic electroluminescence device, which is represented by the following formula (1):

[Chem. 1]

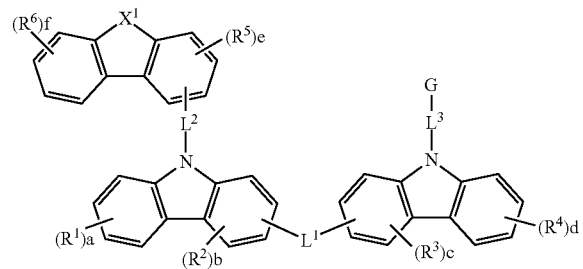

(1)

in the formula (1), G represents a substituted or unsubstituted aryl group having 6 to 18 ring carbon atoms, or the following formula (A):

[Chem. 2]

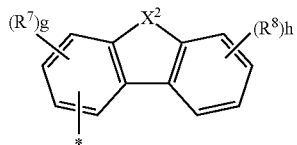

(A)

in the formula (A), * represents a bond to $L^3$, and in the formula (1), $X^1$ represents a sulfur atom or N—$R^9$, and in the formula (A), $X^2$ represents a sulfur atom or N—$R^{10}$;

$R^1$ to $R^8$ each independently represent a substituted or unsubstituted alkyl group having 1 to 4 carbon atoms, a substituted or unsubstituted cycloalkyl group having 3 to 6 ring carbon atoms, a substituted or unsubstituted alkoxy group having 1 to 4 carbon atoms, a substituted or unsubstituted cycloalkoxy group having 3 to 6 ring carbon atoms, a substituted or unsubstituted aryl group having 6 to 18 ring carbon atoms, a substituted or unsubstituted aryloxy group having 6 to 18 ring carbon atoms, a substituted or unsubstituted heteroaryl group having 5 to 18 ring atoms, an amino group which is substituted with an alkyl group having 1 to 4 carbon atoms or is unsubstituted, a silyl group which is substituted with an alkyl group having 1 to 6 carbon atoms or is unsubstituted, a fluoro group, or a cyano group, and alkyl groups represented by $R^1$ to $R^8$ may form a ring;

when G and $R^1$ to $R^8$ have substituents, the substituents R's each independently represent an alkyl group having 1 to 4 carbon atoms, a cycloalkyl group having 3 to 6 ring carbon atoms, an alkoxy group having 1 to 4 carbon atoms, a cycloalkoxy group having 3 to 6 ring carbon atoms, an aryl group having 6 to 18 ring carbon atoms, a heteroaryl group having 5 to 18 ring atoms, an aryloxy group having 6 to 18 ring carbon atoms, an amino group which is substituted with an alkyl group having 1 to 4 carbon atoms or is unsubstituted, a silyl group which is substituted with an alkyl group having 1 to 6 carbon atoms or is unsubstituted, a fluoro group, or a cyano group;

a, d, and f each independently represent an integer of any one of 0 to 4, b, c, and e each independently represent an integer of any one of 0 to 3, and a relationship of 0≤(a+b+c+d+e+f)≤4 is established;

$R^9$ and $R^{10}$ each independently represent an alkyl group having 1 to 5 carbon atoms, a phenyl group, a toluoyl group, a dimethylphenyl group, a trimethylphenyl group, a biphenyl group, a dibenzofuranyl group, or a dibenzothiophenyl group;

g represents an integer of any one of 0 to 3, h represents an integer of any one of 0 to 4, and a relationship of 0≤(g+h)≤4 is established;

provided that when $X^1$ and $X^2$ each represent nitrogen, and the substituent $R^9$ represents a phenyl group, a case where the substituent $R^{10}$ represents a phenyl group is excluded;

$L^1$ represents a single bond, a divalent linking group including N, a divalent linking group including O, a divalent linking group including Si, a divalent linking group including P, a divalent linking group including S, an alkylene group having 1 to 5 carbon atoms, a cycloalkylene group having 3 to 6 ring carbon atoms, an arylene group having 6 to 18 ring carbon atoms, or a heteroarylene group having 5 to 18 ring atoms;

$L^2$ and $L^3$ each independently represent a single bond, an alkylene group having 1 to 5 carbon atoms, a cycloalkylene group having 3 to 6 ring carbon atoms, an arylene group having 6 to 18 ring carbon atoms, or a heteroarylene group having 5 to 18 ring atoms; and $L^1$ to $L^3$ may each be further substituted with any one of the substituents R's, provided that when $L^1$ represents an arylene group or a heteroarylene group, relationships of 1≤a≤4 and 1≤d≤4 are established.

The present invention also provides an organic EL device, including one or more organic thin film layers including a light emitting layer between a cathode and an anode, in which at least one layer of the organic thin film layers contains the material for an organic electroluminescence device represented by the formula (1).

Advantageous Effects of Invention

According to the present invention, there can be provided an organic EL device that emits phosphorescence at a low driving voltage, and has high efficiency and a long lifetime, and a material for an organic electroluminescence device for realizing the device.

DESCRIPTION OF EMBODIMENTS

A material for an organic electroluminescence device of the present invention is represented by the following formula (1):

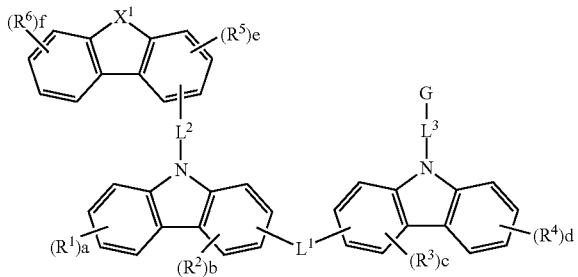

in the formula (1), G represents a substituted or unsubstituted aryl group having 6 to 18 ring carbon atoms, or the following formula (A):

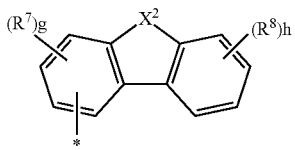

in the formula (A), * represents a bond to $L^3$, and in the formula (1), $X^1$ represents a sulfur atom or N—$R^9$, and in the formula (A), $X^2$ represents a sulfur atom or N—$R^{10}$;

$R^1$ to $R^8$ each independently represent a substituted or unsubstituted alkyl group having 1 to 4 carbon atoms, a substituted or unsubstituted cycloalkyl group having 3 to 6 ring carbon atoms, a substituted or unsubstituted alkoxy group having 1 to 4 carbon atoms, a substituted or unsubstituted cycloalkoxy group having 3 to 6 ring carbon atoms, a substituted or unsubstituted aryl group having 6 to 18 ring carbon atoms, a substituted or unsubstituted aryloxy group having 6 to 18 ring carbon atoms, a substituted or unsubstituted heteroaryl group having 5 to 18 ring atoms, an amino group which is substituted with an alkyl group having 1 to 4 carbon atoms or is unsubstituted, a silyl group which is substituted with an alkyl group having 1 to 6 carbon atoms or is unsubstituted, a fluoro group, or a cyano group, and alkyl groups represented by $R^1$ to $R^8$ may form a ring;

when G and $R^1$ to $R^8$ have substituents, the substituents R's each independently represent an alkyl group having 1 to 4 carbon atoms, a cycloalkyl group having 3 to 6 ring carbon atoms, an alkoxy group having 1 to 4 carbon atoms, a cycloalkoxy group having 3 to 6 ring carbon atoms, an aryl group having 6 to 18 ring carbon atoms, a heteroaryl group having 5 to 18 ring atoms, an aryloxy group having 6 to 18 ring carbon atoms, an amino group which is substituted with an alkyl group having 1 to 4 carbon atoms or is unsubstituted, a silyl group which is substituted with an alkyl group having 1 to 6 carbon atoms or is unsubstituted, a fluoro group, or a cyano group;

a, d, and f each independently represent an integer of any one of 0 to 4, b, c, and e each independently represent an integer of any one of 0 to 3, and a relationship of 0≤(a+b+c+d+e+f)≤4 is established;

$R^9$ and $R^{10}$ each independently represent an alkyl group having 1 to 5 carbon atoms, a phenyl group, a toluoyl group, a dimethylphenyl group, a trimethylphenyl group, a biphenyl group, a dibenzofuranyl group, or a dibenzothiophenyl group;

g represents an integer of any one of 0 to 3, h represents an integer of any one of 0 to 4, and a relationship of 0≤(g+h)≤4 is established;

provided that when $X^1$ and $X^2$ each represent nitrogen, and the substituent $R^9$ represents a phenyl group, a case where the substituent $R^{10}$ represents a phenyl group is excluded;

$L^1$ represents a single bond, a divalent linking group including N, a divalent linking group including O, a divalent linking group including Si, a divalent linking group including P, a divalent linking group including S, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms;

$L^2$ and $L^3$ each independently represent a single bond, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms; and $L^1$ to $L^3$ may each be further substituted with any one of the substituents R's, provided that when $L^1$ represents an arylene group or a heteroarylene group, relationships of 1≤a≤4 and 1≤c≤4 are established.

In particular, when a dibenzothiophenyl group or a carbazolyl group is bonded to a carbazolyl group at its N-position (9-position) directly or through a linking group like the formula (1), the LUMO level of the dibenzothiophene or carbazolyl group deepens, which facilitates the injection of an electron into, for example, the light emitting layer of an organic EL device using the material for an organic electroluminescence device of the present invention. As a result, the carrier balance of the device can be easily adjusted and hence an effect of the present invention is favorably exerted.

Examples of the alkyl group represented by each of $R^1$ to $R^8$ include a methyl group, an ethyl group, a propyl group, an isopropyl group, a n-butyl group, a s-butyl group, an isobutyl group, a t-butyl group, a n-pentyl group, and a neopentyl group.

Examples of the cycloalkyl group represented by each of $R^1$ to $R^8$ include a cyclopropyl group, a cyclobutyl group, a cyclopentyl group, and a cyclohexyl group.

Examples of the alkoxy group represented by each of $R^1$ to $R^8$ include a methoxy group, an ethoxy group, a propoxy group, a butoxy group, and a pentyloxy group, and groups having three or more carbon atoms may be linear, cyclic, or branched.

Examples of the cycloalkoxy group represented by each of $R^1$ to $R^8$ include a cyclopentoxy group and a cyclohexyloxy group.

Examples of the aryloxy group represented by each of $R^1$ to $R^8$ include a phenoxy group and a biphenyloxy group.

Examples of the aryl group represented by G and each of $R^1$ to $R^8$ include a phenyl group, a tolyl group, a xylyl group, amesityl group, an o-biphenyl group, am-biphenyl group, a p-biphenyl group, an o-terphenyl group, a m-terphenyl group, a p-terphenyl group, a naphthyl group, and a phenanthryl group. Of those, a phenyl group and a mesityl group are preferred.

Examples of the heteroaryl group represented by each of $R^1$ to $R^8$ include a carbazolyl group, a dibenzofuranyl group, a dibenzothiophenyl group, a pyrrolyl group, a furyl group, a thienyl group, a silolyl group, a pyridyl group, a quinolyl group, an isoquinolyl group, a benzofuryl group, an imidazolyl group, a pyrimidyl group, a selenophenyl group, an oxadiazolyl group, and a triazolyl group.

The amino group and silyl group, which are represented by each of $R^1$ to $R^8$ may be substituted by such substituent as described previously. As the silyl group, a trimethylsilyl group is preferred.

In addition, for example, when a≥2 in the compound represented by the formula (1), a plurality of groups each represented by $R^1$ exist. In this case, the groups each represented by $R^1$ may be identical to or different from each other. The same holds true for $R^2$, $R^3$, $R^4$, $R^5$, $R^6$, $R^7$, and $R^8$.

Examples of the substituent with which $R^1$ to $R^8$ may each be substituted include an alkyl group having 1 to 5 carbon atoms, a cycloalkyl group having 3 to 6 ring carbon atoms, an alkoxy group having 1 to 5 carbon atoms, a cycloalkoxy group having 3 to 6 ring carbon atoms, an aryl group having 6 to 18 ring carbon atoms, a heteroaryl group having 5 to 18 ring atoms, an aryloxy group having 6 to 18 ring carbon atoms, an amino group which is substituted with an alkyl group having 1 to 4 carbon atoms or is unsubstituted, and a silyl group which is substituted with an alkyl group having 1 to 6 carbon atoms or is unsubstituted. Specific examples thereof include the same specific examples as those described for $R^1$ to $R^8$.

a, d, f, and h each independently represent preferably an integer of any one of 0 to 3, more preferably an integer of any one of 0 to 2. In addition, b, c, e, and g each independently represent preferably an integer of any one of 0 to 2, more preferably an integer of 0 or 1. Further, the total of a to h is preferably 4 or less in consideration of the fact that the sublimation or vapor deposition of the compound is apt to involve its thermal decomposition when its molecular weight becomes excessively large.

Examples of the divalent linking group including N, the divalent linking group including O, the divalent linking group including Si, the divalent linking group including P, and the divalent linking group including S each represented by $L^1$ include the following groups.

[Chem. 5]

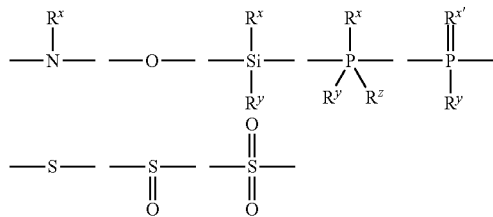

In the respective formulae, $R^x$, $R^y$, and $R^z$ each independently represent a hydrogen atom or a group selected from the substituents R's, and $R^{x'}$ represents oxygen.

Of the groups, an "—S—" group (sulfide group), a sulfoxide group, a phosphoxide group, or an ether group is preferred.

Examples of the alkylene group having 1 to 5 carbon atoms, the cycloalkylene group having 3 to 6 ring carbon atoms, the arylene group having 6 to 18 ring carbon atoms, the heteroarylene group having 5 to 18 ring carbon atoms, the divalent amino group, and the divalent silyl group each represented by any one of $L^1$ to $L^3$ include groups each obtained by replacing one hydrogen atom of a group described for $R^1$ to $R^8$ with a bonding hand. In the present invention, a 9,9-fluorenylidene group is also included in the arylene group.

A p-phenylene group, an m-phenylene group, or a biphenylene group as well as the foregoing is suitable as the arylene group, and a biphenylamino group as well as the foregoing is suitable as the amino group.

Linking groups represented by $L^1$ to $L^3$ may each further have a substituent, and the substituent has the same meaning as that of a substituent described for the groups R's with which $R^1$ to $R^8$ are substituted.

In the formula (1) of the material for an organic electroluminescence device of the present invention, the case where the $X^1$ represents a sulfur atom and the G satisfies one of the following items (a) and (b) is preferred, and the case where the G satisfies the item (b) is more preferred:
(a) the G represents an aryl group having 6 to 18 ring carbon atoms; and
(b) the G represents the formula (A) where $X^2$ represents a sulfur atom.

The material for an organic electroluminescence device of the present invention is preferably represented by the following formula (2):

[Chem. 6]

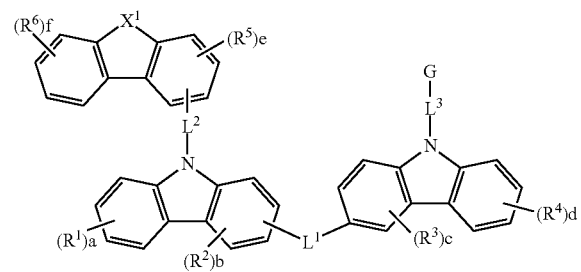

(2)

in the formula (2), $X^1$, $R^1$ to $R^6$, a to f, $L^1$ to $L^3$, and G each have the same meaning as that described in the formula (1).

The advantages of the case where two carbazolyl groups are bonded to each other at their 3-positions directly or through a linking group like the formula (2) are as described below.

(1) Convenience in synthesis is high.
(2) As the 3- and 6-positions of carbazole are positions poor in chemical stability, the introduction of a substituent except a hydrogen atom into even one of the 3- and 6-positions may improve the chemical stability. Accordingly, such a structure that a substituent is further introduced into the 6-position is more preferred.
(3) When carbazole molecules are bonded to each other at their 3-positions through a single bond, N atoms on the two carbazole molecules conjugate with each other to shallow the HOMO level of the material. As a result, its hole injecting/transporting property is improved and hence the carrier balance of a device using the material can be easily adjusted.

The material for an organic electroluminescence device of the present invention is preferably a host material, hole transporting material, or electron transporting material to be used together with a phosphorescent light emitting material. The material is more preferably a host material or a hole transporting material directly adjacent to a light emitting layer.

The material for an organic electroluminescence device of the present invention is preferably such that $L^2$ and $L^3$ each represent a single bond because of the following reason. A deepening effect on the LUMO level of the dibenzothiophenyl group or carbazolyl group bonded to the N-position (9-position) of the carbazolyl group strengthens as compared with that in the case where $L^2$ and $L^3$ each represent a linking group. Such case is preferred also because of the following reason. When $L^2$ and $L^3$ each represent a single bond, the molecular weight of the material reduces and hence a temperature needed in its sublimation or vapor deposition step can be lowered. As a result, when the material is used as a material for an organic electroluminescence device produced by employing a sublimation or vapor deposition method, its thermal decomposition can be easily suppressed.

In addition, the material for an organic electroluminescence device of the present invention is preferably represented by the following formula (3) in order that its chemical stability may be additionally improved.

[Chem. 7]

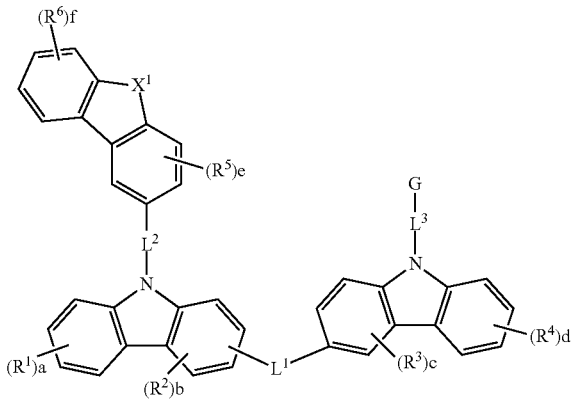

(3)

in the formula (3), $R^1$, $R^4$, and $R^6$ each independently represent a hydrogen atom or an aryl group having 6 to 18 ring carbon atoms, and the aryl group may be further substituted with the substituent $R^1$, and $R^2$, $R^3$, $R^5$, $X^1$, $L^1$ to $L^3$, and G each have the same meaning as that described in the formula (1).

The case where $L^1$ in any one of the formulae (1) to (3) represents a single bond is preferred because of the following reason. A π-conjugation effect between the N atoms on the two carbazole molecules becomes higher than that in the case where $L^1$ represents a linking group, and hence the HOMO level shallows. As a result, the hole injecting/transporting property is improved and hence the carrier balance can be easily adjusted.

Such case is preferred also because of the following reason. When $L^1$ represents a single bond, the molecular weight of the material reduces and hence a temperature needed in its sublimation or vapor deposition step can be lowered. As a result, when the material is used as a material for an organic electroluminescence device produced by employing a sublimation or vapor deposition method, its thermal decomposition can be easily suppressed.

In addition, from the viewpoint of an improvement in sublimation property based on the properties of a substituent and its molecular weight, the material for an organic electroluminescence device represented by the formula (1) is preferably such that when G represents a group represented by the formula (A), and $X^1$ and $X^2$ each represent nitrogen, $R^9$ and $R^{10}$ each represent an alkyl group having 5 or less carbon atoms.

Further, from the same viewpoint, the case where $X^1$ and $X^2$ do not simultaneously represent nitrogen (that is, one of $X^1$ and $X^2$ represents a nitrogen atom, and the other represents a sulfur atom) is preferred because the molecular weight can be easily reduced.

In the formula (1), when $L^1$ represents an arylene group or a heteroarylene group, $R^1$ or $R^4$ preferably represents any one of an unsubstituted phenyl group, a toluoyl group, a xylyl group, and a mesityl group. In this case, $R^1$ and $R^4$ may be identical to or different from each other.

In addition, the arylene group having 6 to 18 ring carbon atoms represented by $L^1$, $L^2$, or $L^3$ is suitably an o-phenylene group, an m-phenylene group, a p-phenylene group, or an arylene group having 10 to 18 ring carbon atoms.

In addition, the case where $L^1$ represents one selected from a divalent linking group including O, a divalent linking group including Si, a divalent linking group including P, a divalent linking group including S, an alkylene group having 1 to 5 carbon atoms, and a cycloalkylene group having 3 to 6 ring carbon atoms is preferred because the triplet energy of the material can be easily increased as compared with that in the case where $L^1$ represents an arylene group or a heteroarylene group.

In consideration of the fact that the sublimation or vapor deposition of the material for an organic electroluminescence device of the present invention is apt to involve its thermal decomposition when its molecular weight becomes excessively large, the molecular weight is preferably 1,000 or less, more preferably 950 or less, still more preferably 925 or less, still further more preferably 900 or less.

It has been known that the sublimation temperature of a material for an organic electroluminescence device tends to become higher as its intermolecular force enlarges or its molecular weight increases.

On the other hand, many organic materials for organic electroluminescence devices each have a thermal decomposition temperature ranging from around 400° C. to at most less than 500° C. Of the compounds conventionally known as materials for organic EL devices, a large number of such compounds as described below exist. Each of the compounds can sublimate at such a temperature that its thermal decomposition does not occur, but performance to be obtained when an organic EL device is produced from the compound is insufficient.

In view of the foregoing, when its molecular weight is set to fall within such range as described above, the material can sublimate at such a temperature that its thermal decomposition does not occur to a very large extent, and can show suitable properties when used in an organic EL device (especially a phosphorescent device).

The material for an organic electroluminescence device of the present invention preferably has as high a triplet energy as possible because of the following reason. As the triplet energy increases, a confining effect on a triplet exciton of a phosphorescent light emitting dopant becomes higher, which leads to an improvement in luminous efficiency of the device. The triplet energy is preferably 2.70 eV or more. In particular, when the material is used in a blue light emitting device, the triplet energy is preferably 2.90 eV or more.

Here, the triplet energy in the present invention is specified as described below. A sample is dissolved in an EPA solvent (diethyl ether, isopentane, and ethanol at a volume ratio of 5:5:2) at 10 μmol/L, and then the resultant solution is used as a sample for phosphorescence measurement. Then, the sample for phosphorescence measurement is charged into a quartz cell. After that, the cell is irradiated with excitation light at a temperature of 77 K, and then the phosphorescence spectrum of radiated phosphorescence is measured. The triplet energy is defined as a value determined on the basis of the spectrum from a conversion equation "$E^T$ (eV)=1,239.85/$\lambda_{edge}$." When the phosphorescence spectrum is represented with an axis of ordinate indicating a phosphorescence intensity and an axis of abscissa indicating a wavelength, the symbol "$\lambda_{edge}$" represents a wavelength value (unit: nm) for the point of intersection of the tangent drawn to the rise-up at shorter wavelengths of the phosphorescence spectrum and the axis of abscissa.

In addition, the material for an organic electroluminescence device of the present invention has a glass transition point of preferably 140° C. or more, more preferably 150° C. or more because the material is excellent in thermal stability. An upper limit for the glass transition point is typically about 260° C. Here, the glass transition point in the present invention is defined as described below. About 3 mg of a sample are subjected to a two-cycle temperature increase and decrease process including the following steps (1) to (6) with a DSC8500 manufactured by PerkinElmer Inc., and the intermediate temperature of a point of inflection at which the baseline of the DSC curve at the time of the temperature increase in the step (6) changes in a stepwise fashion is defined as the glass transition point.

(1) The sample is held at 30° C. for 1 minute.
(2) The sample is heated from 30° C. to a certain temperature less than the thermal decomposition temperature of the sample at a rate of temperature increase of 10° C./min.
(3) The sample is held at the certain temperature for 3 minutes.
(4) The sample is cooled from the certain temperature to 0° C. at 200° C./min.
(5) The sample is held at 0° C. for 10 minutes.
(6) The sample is heated from 0° C. to 200° C. at a rate of temperature increase of 10° C./min.

Specific examples of the material for an organic electroluminescence device represented by the general formula (1) of the present invention are shown below. However, the present invention is not limited to these exemplified compounds. It should be noted that substituents shown in the following specific examples can be given as preferred substituents in the present invention.

[Chem. 8]

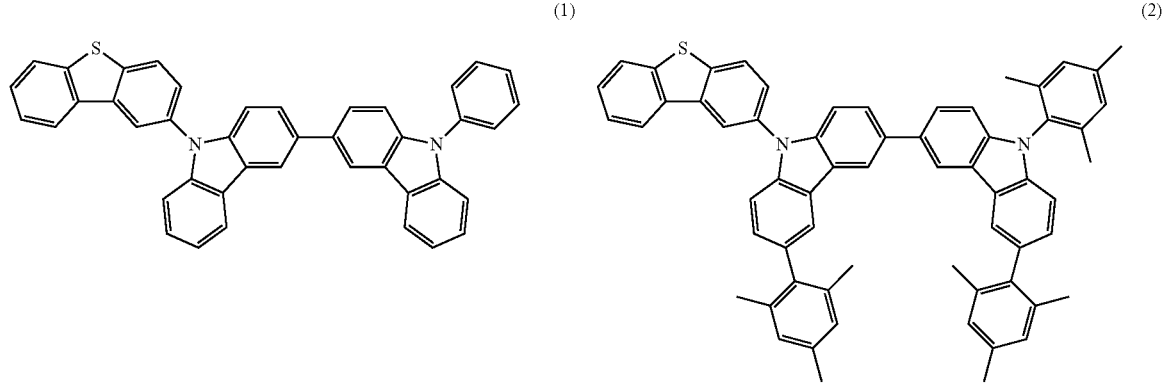

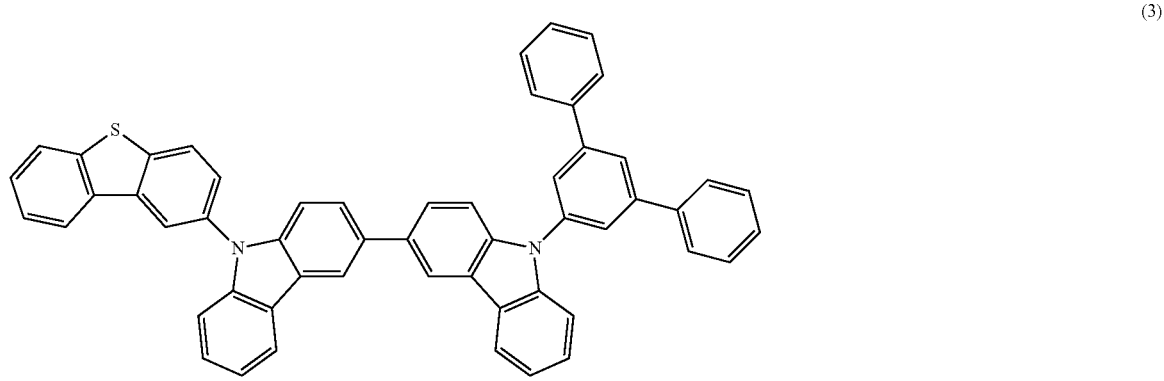

-continued
(4)
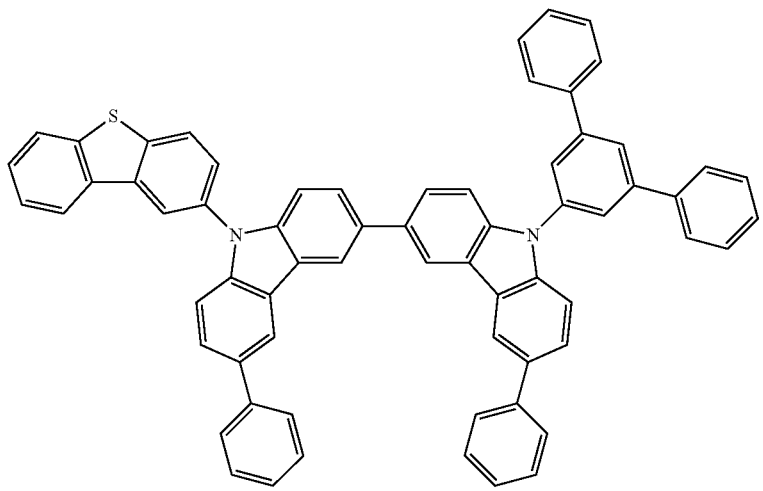
(5)
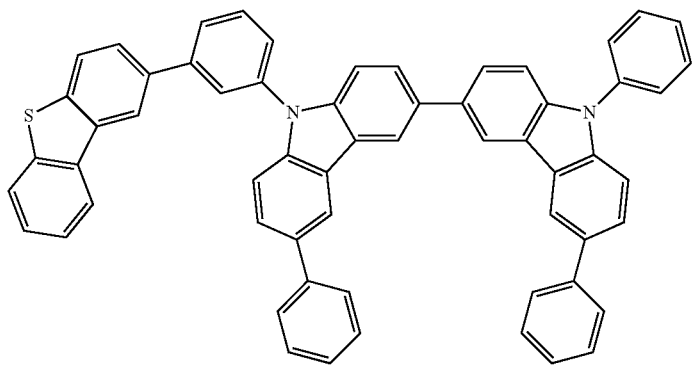
(6)
(7)
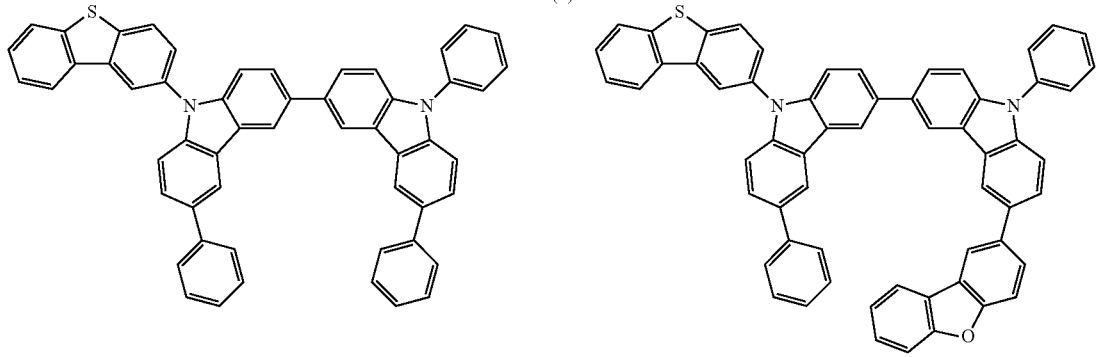
(8)
(9)
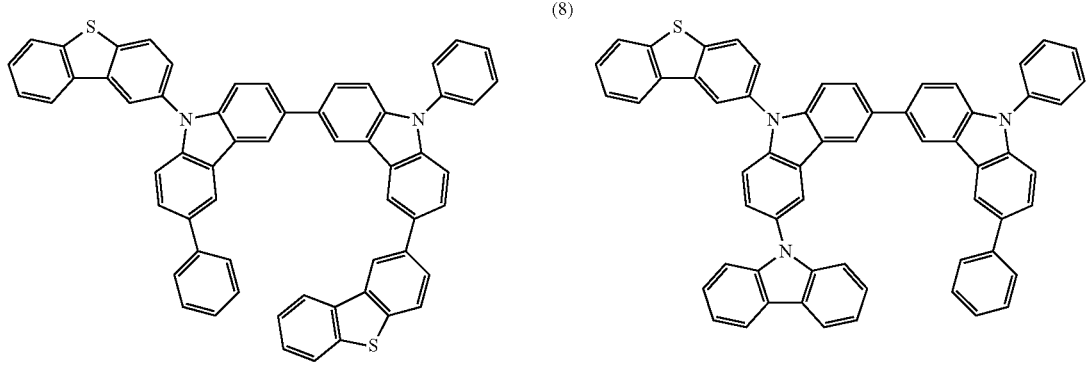

(10)
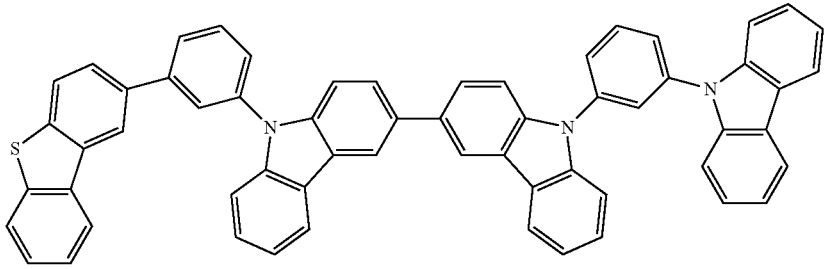
(11)
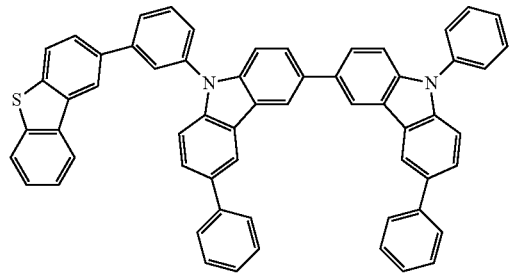
(12)
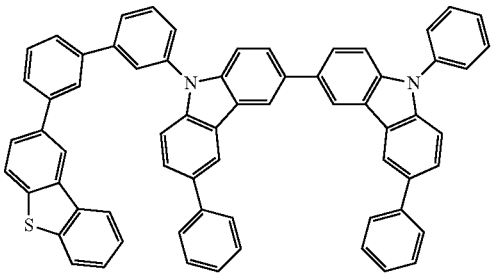
(13)
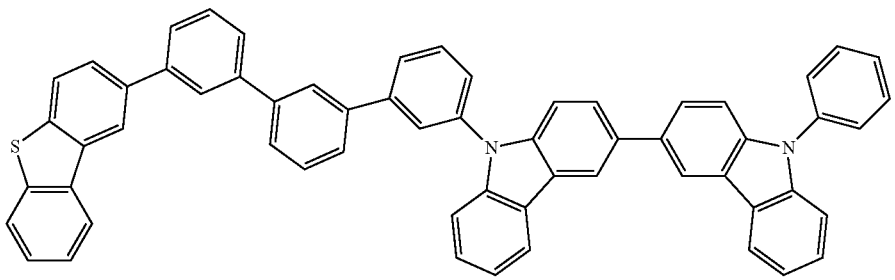
(14)
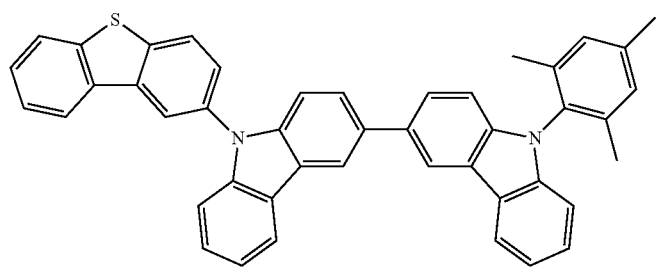
(15)
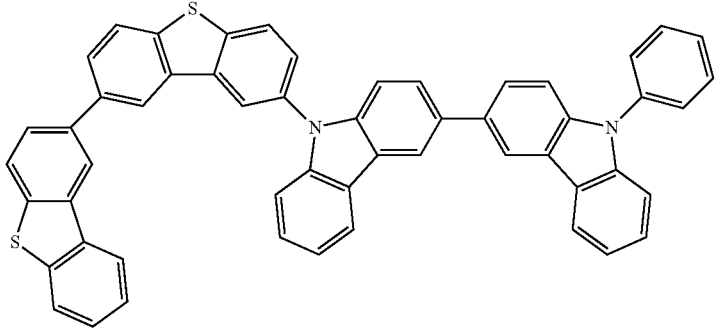

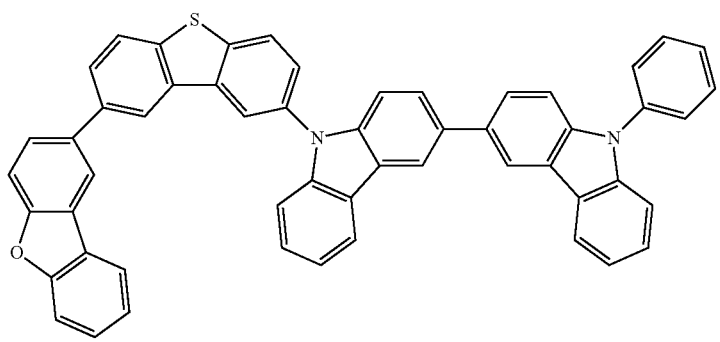
(16)
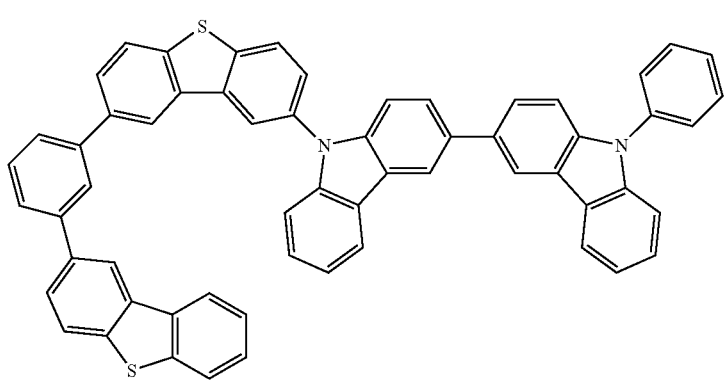
(17)
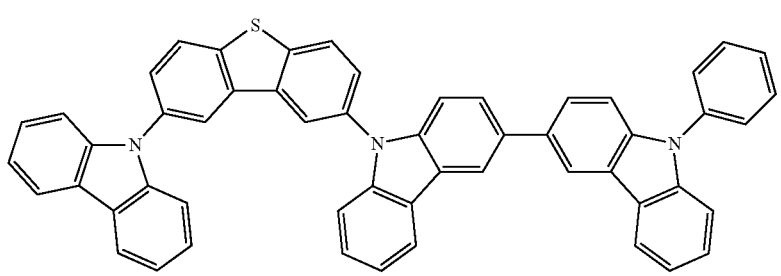
(18)
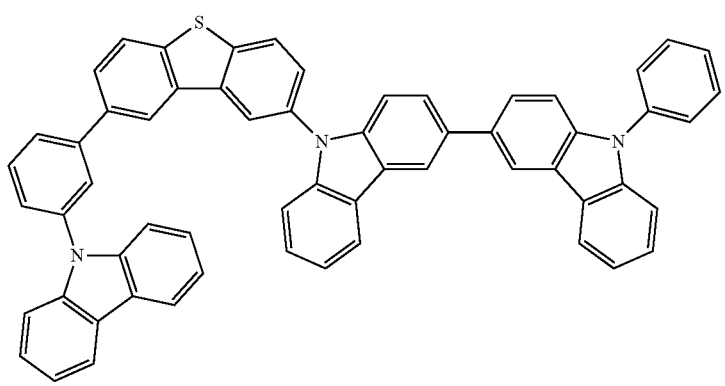
(19)

-continued
(20)
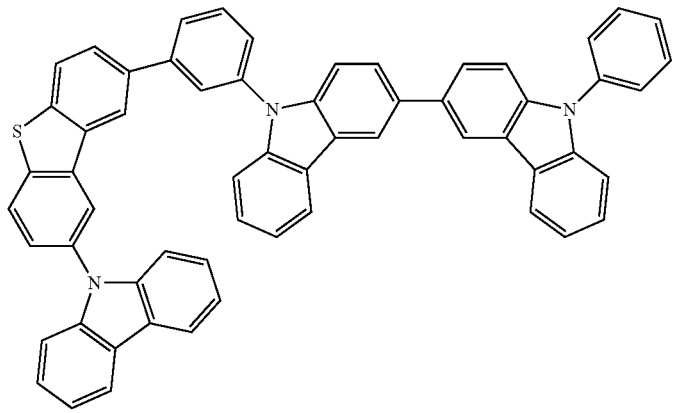
(21)
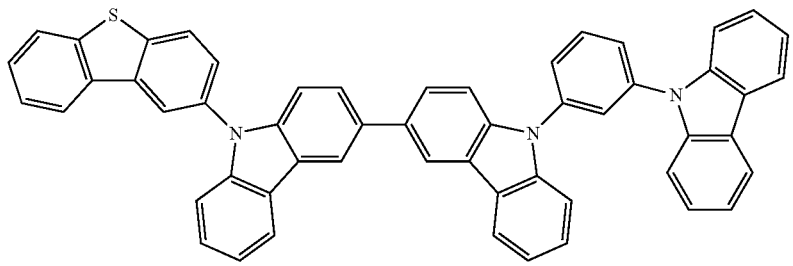
(22)
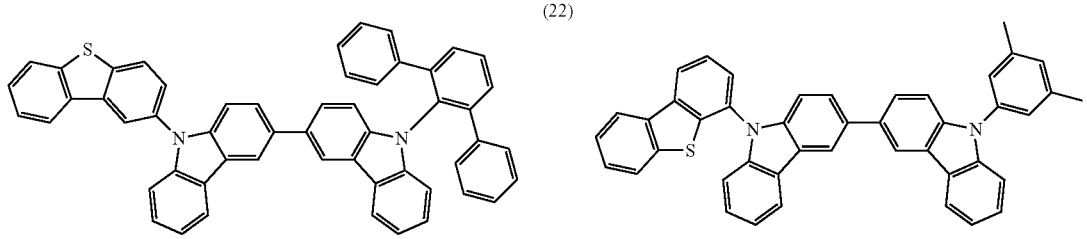
(23)
(24)
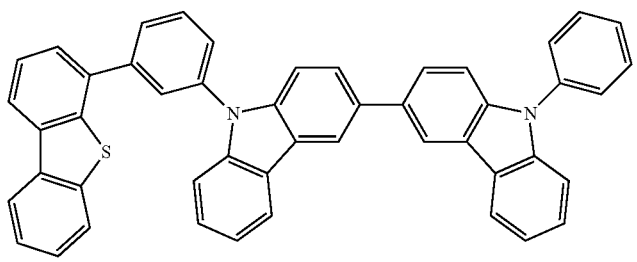
[Chem. 9]
(25)
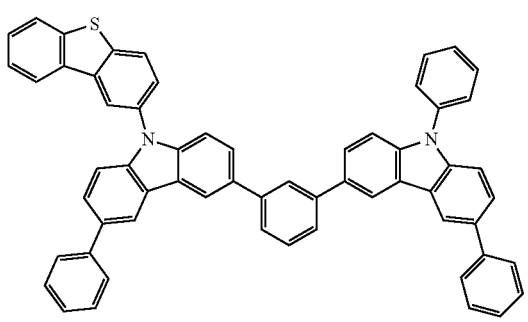
(26)
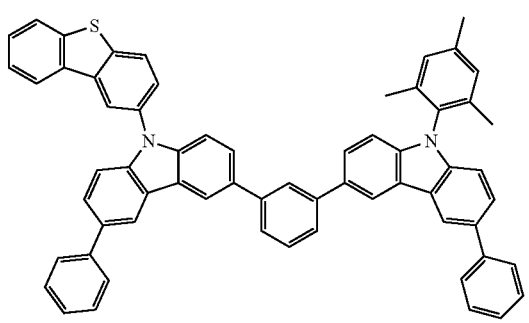

(27)
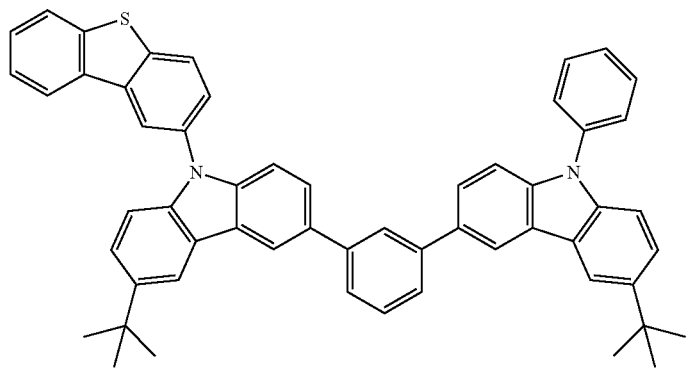
(28)
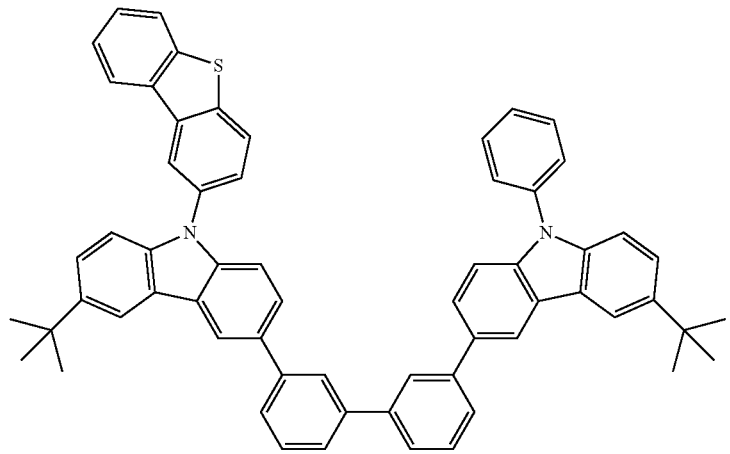
(29)
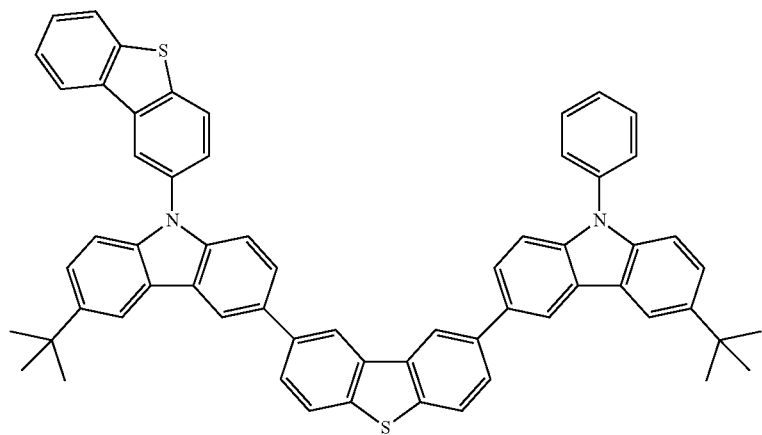
(30)
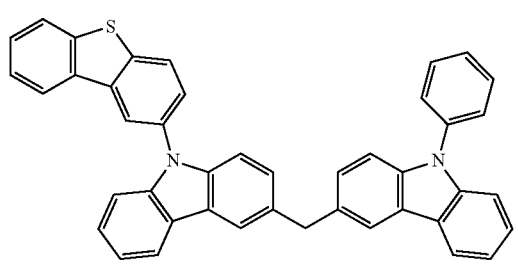
(31)
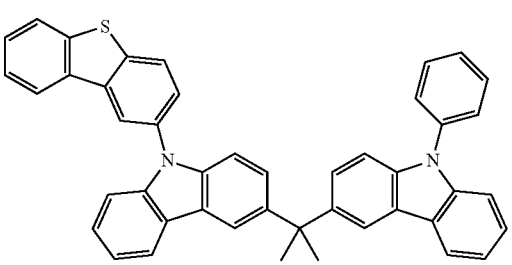

-continued
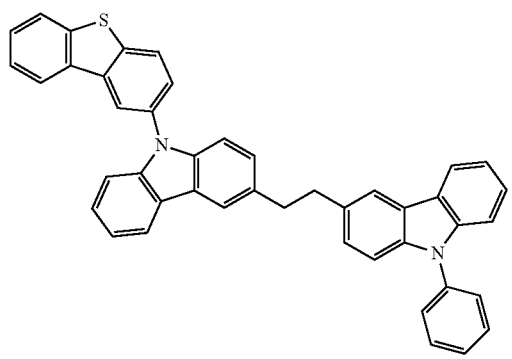
(32)
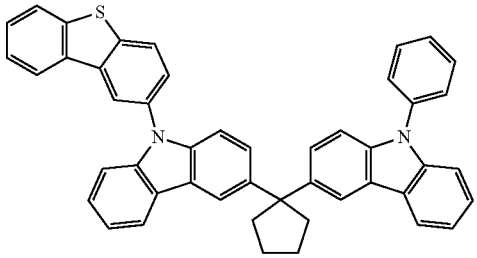
(33)
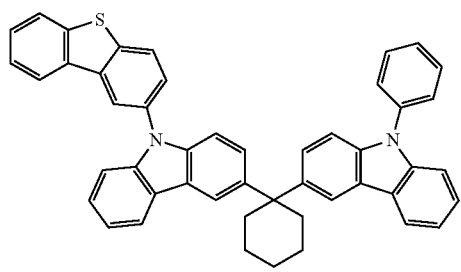
(34)
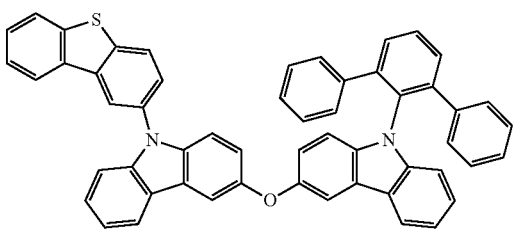
(35)
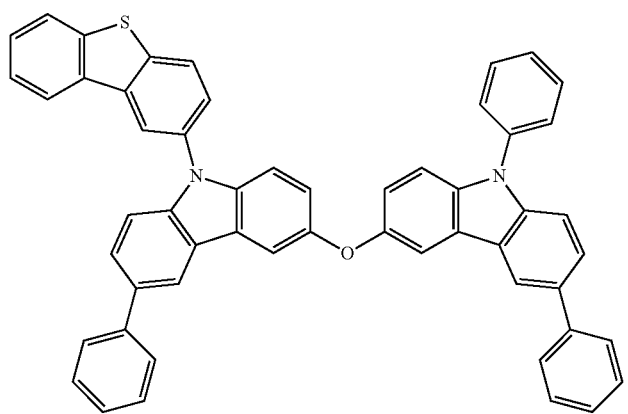
(36)
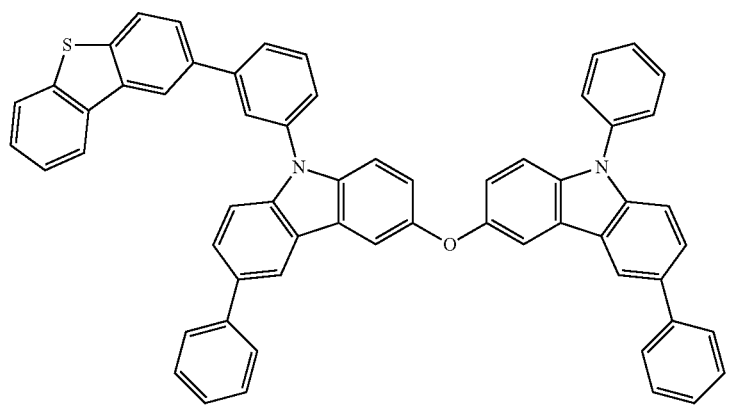
(37)

-continued
(38)
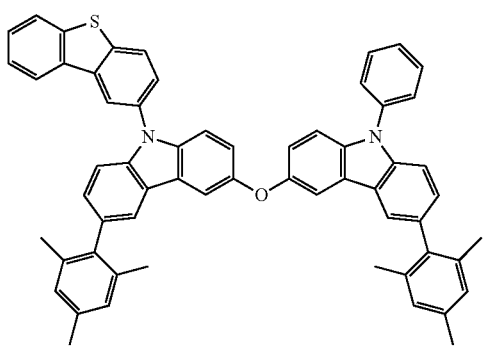
(39)
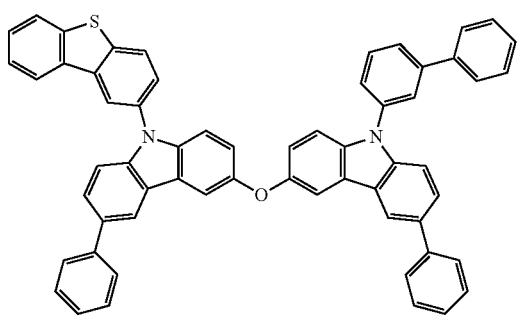
(40)
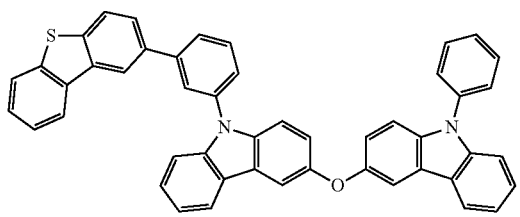
(41)
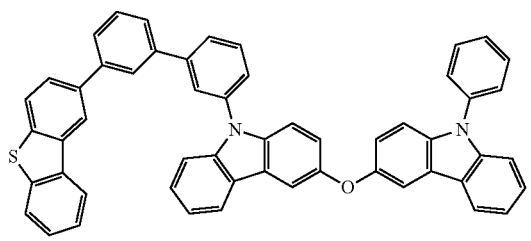
(42)
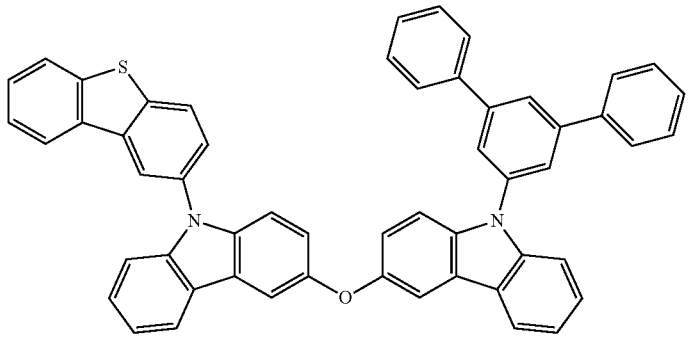
(43)
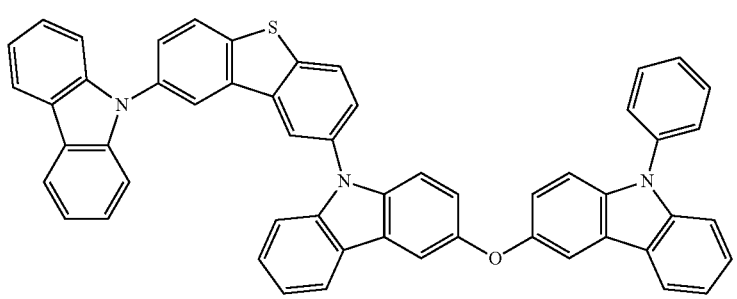
(44)
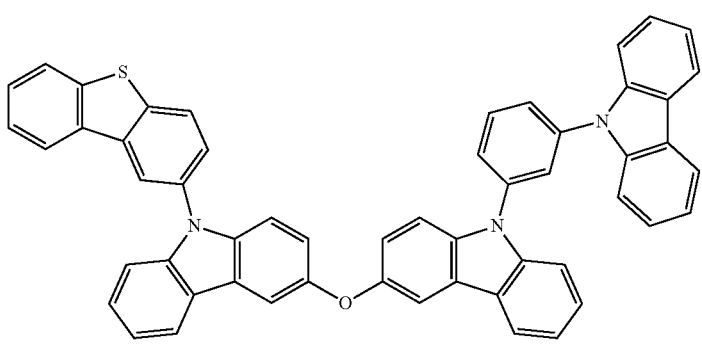

-continued
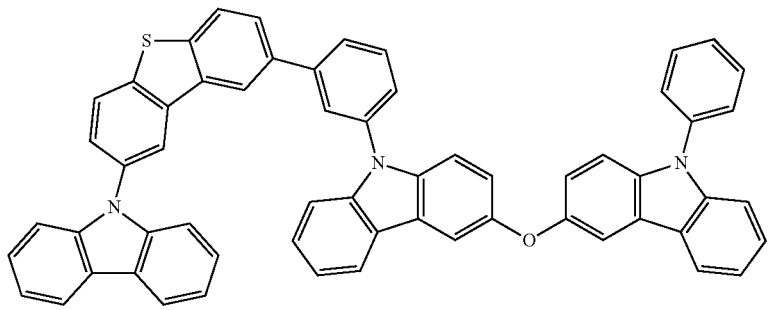
(45)
[Chem. 10]
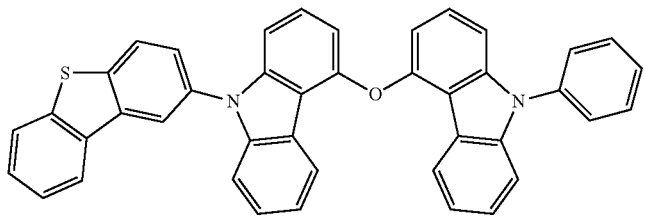
(46)
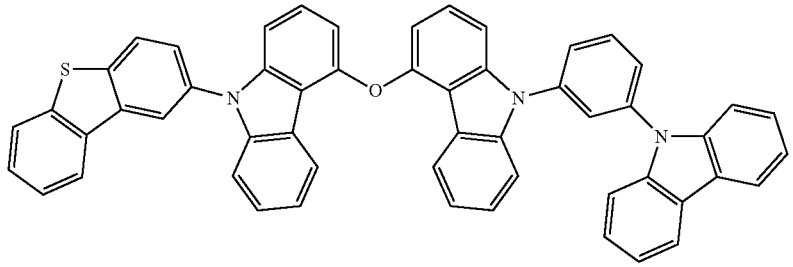
(47)
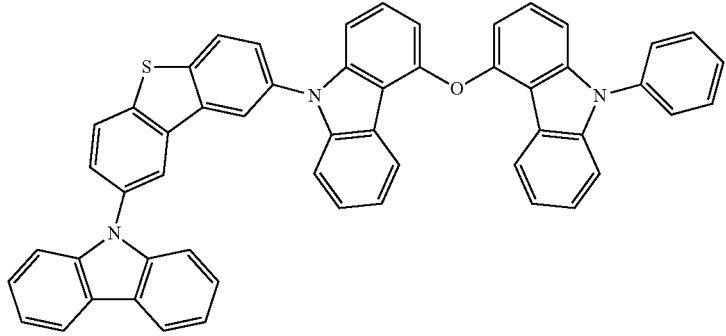
(48)
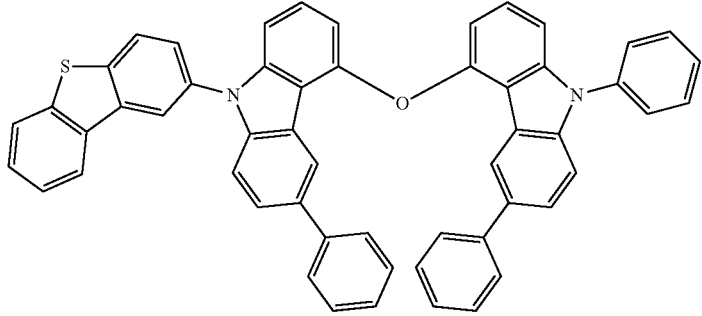
(49)

-continued
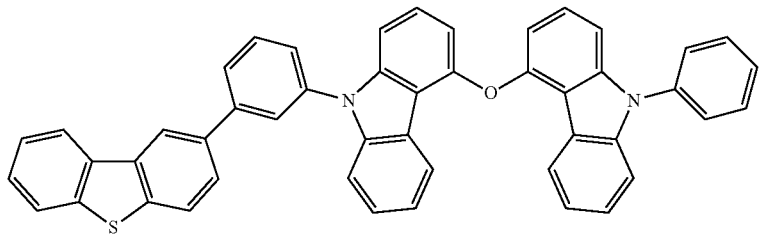
(50)
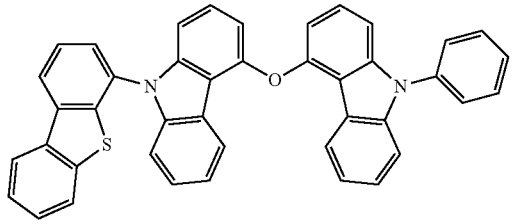
(51)
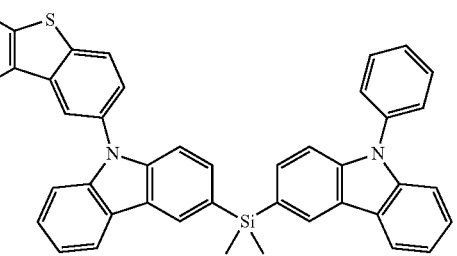
(52)
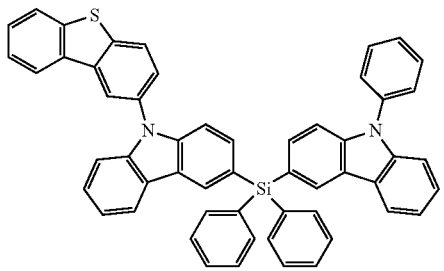
(53)
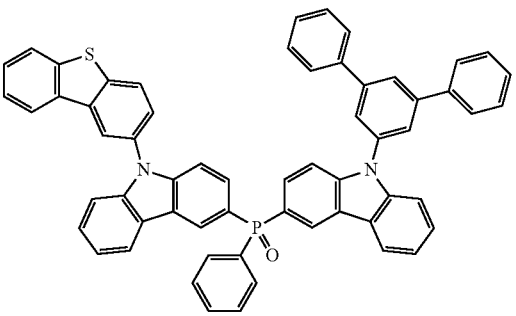
(54)
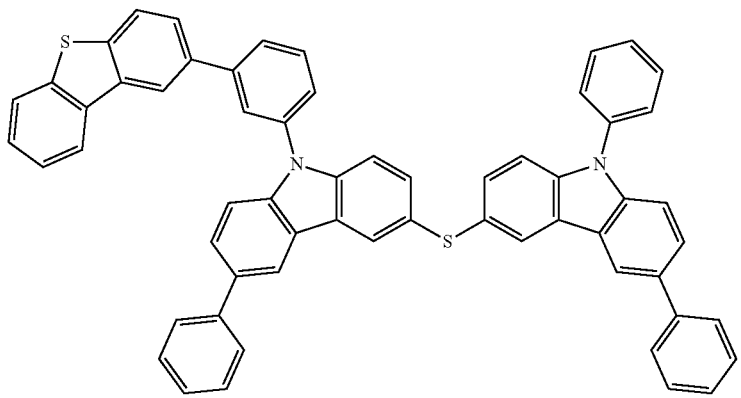
(55)
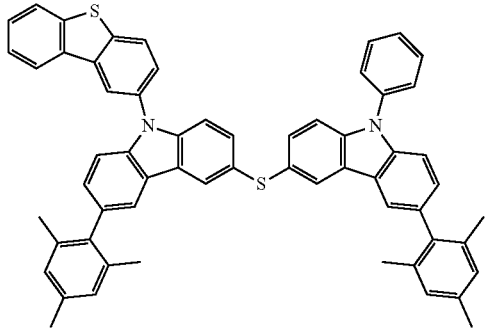
(56)
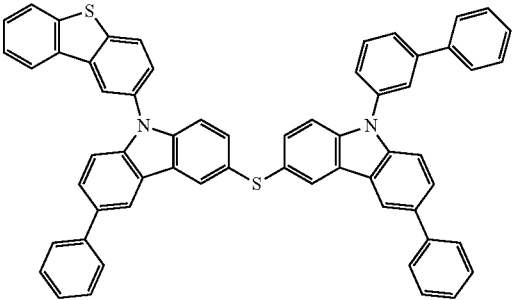
(57)

-continued
(58)
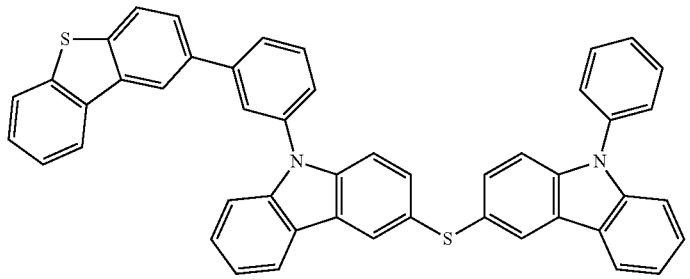
(59)
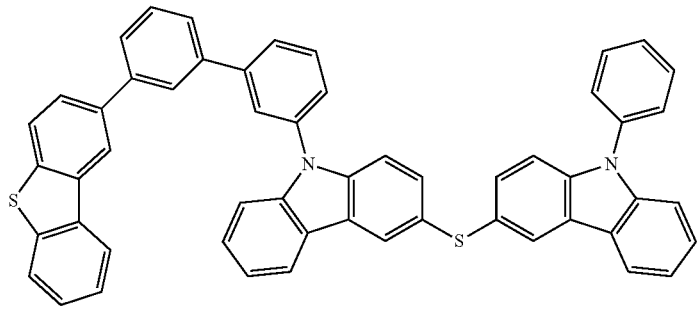
(60)
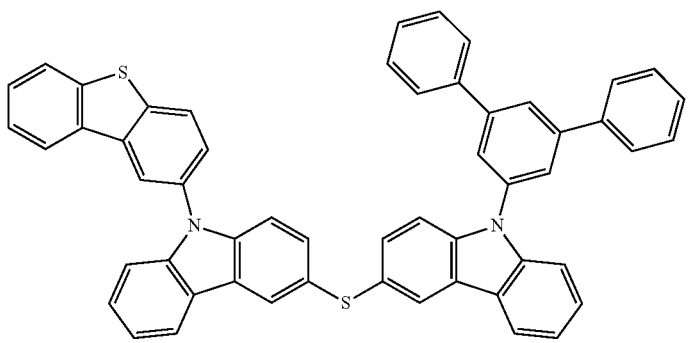
(61)
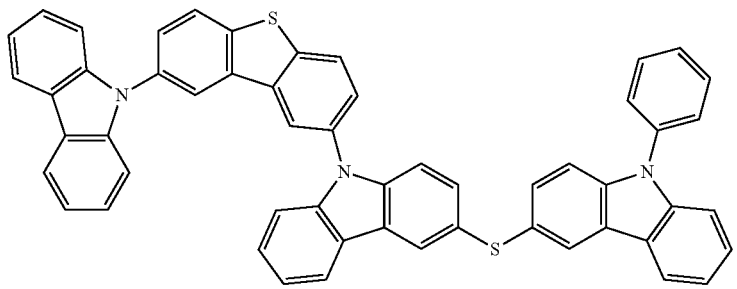
(62)
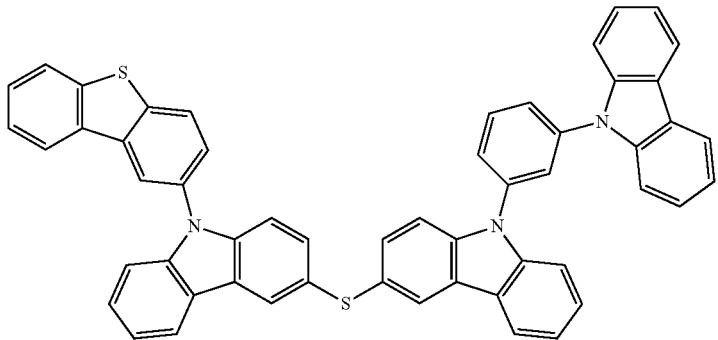

-continued
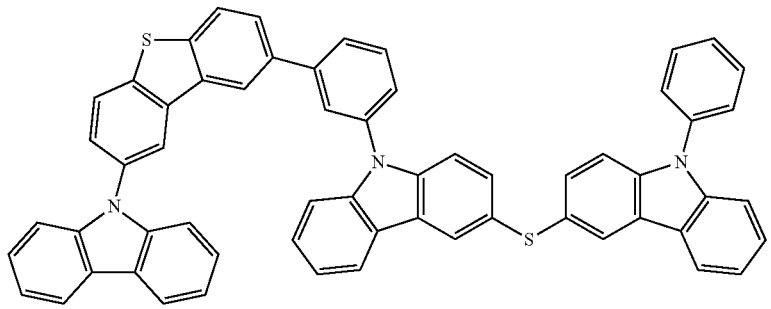
(63)
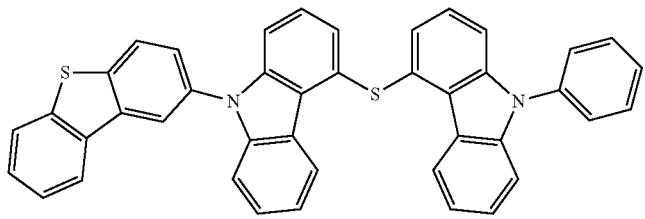
(64)
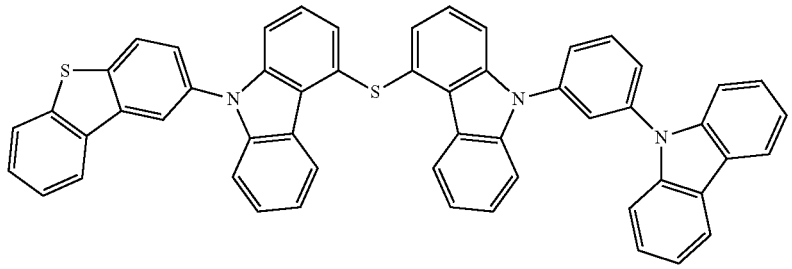
(65)
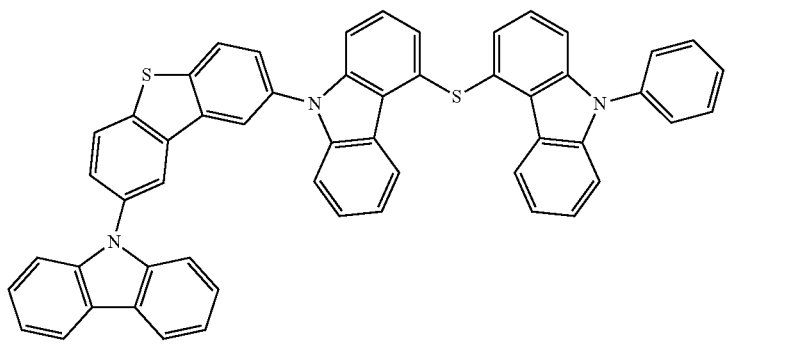
(66)
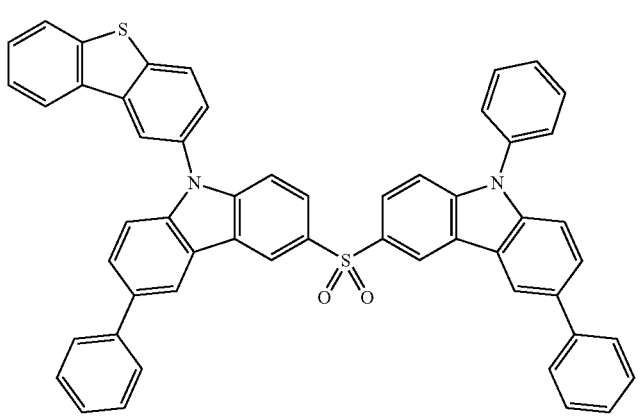
(67)

(68)
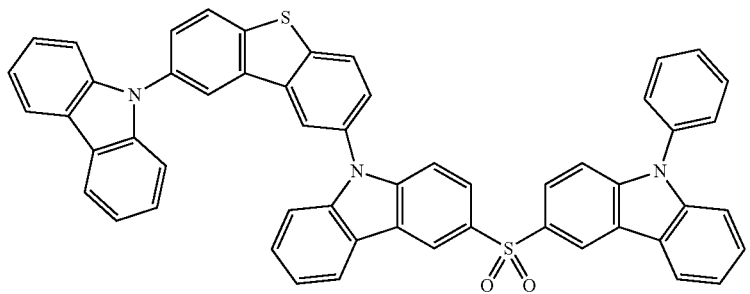
(69)
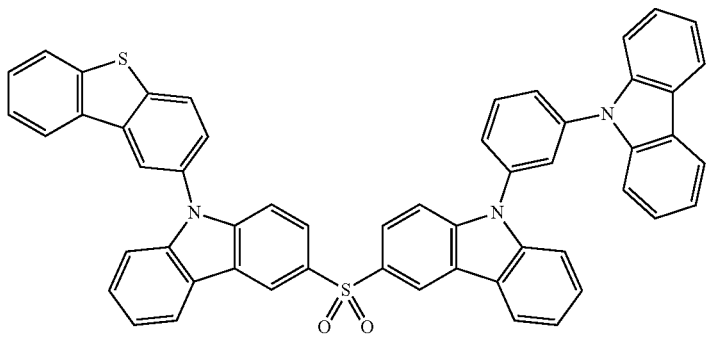
[Chem. 11]
(70)
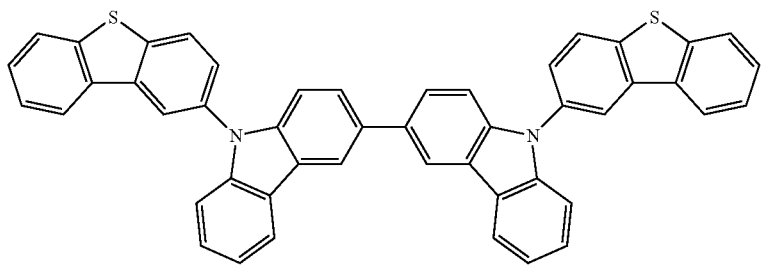
(71)
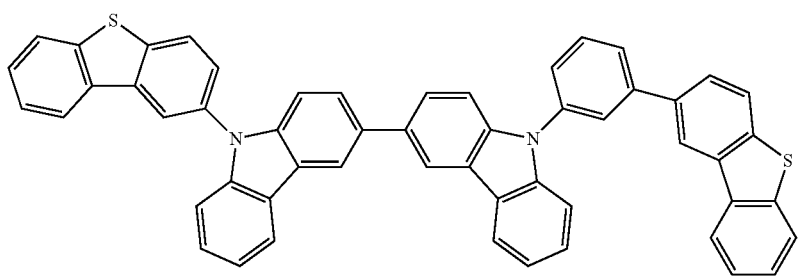
(72)
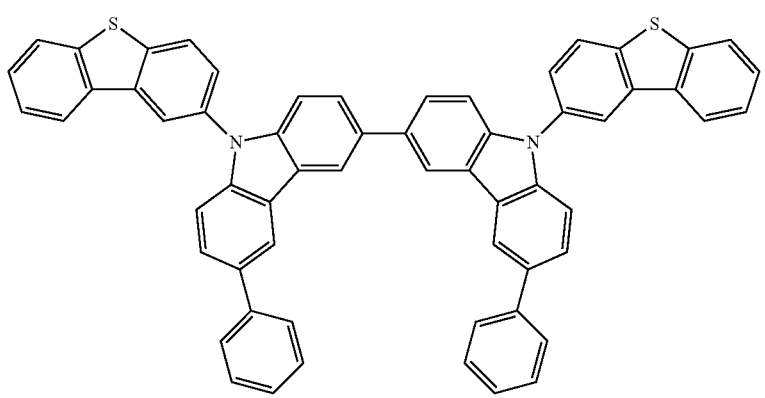

-continued
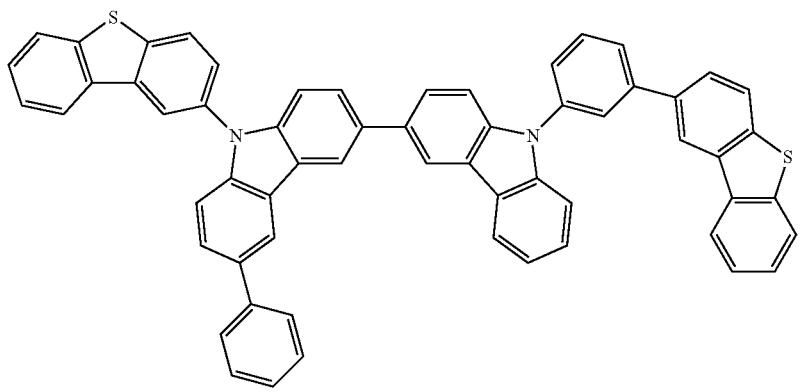
(73)
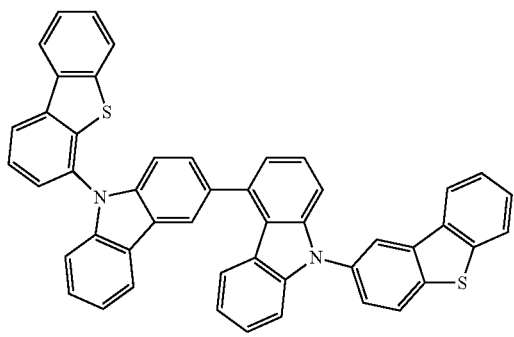
(74)
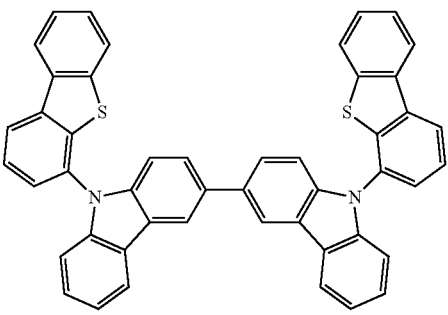
(75)
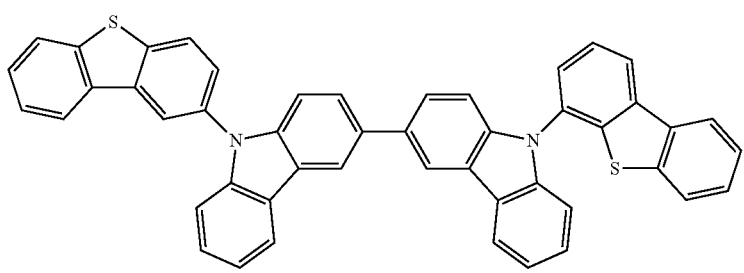
(76)
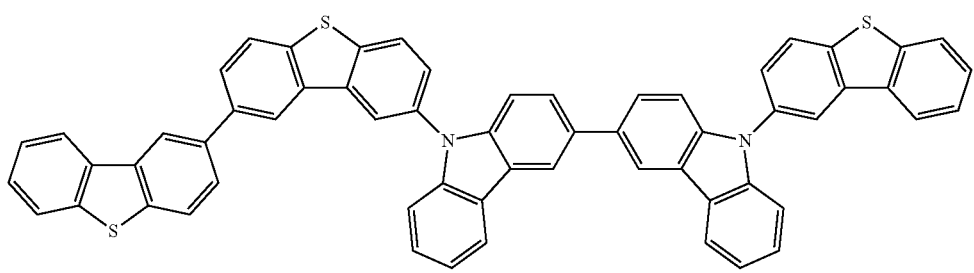
(77)
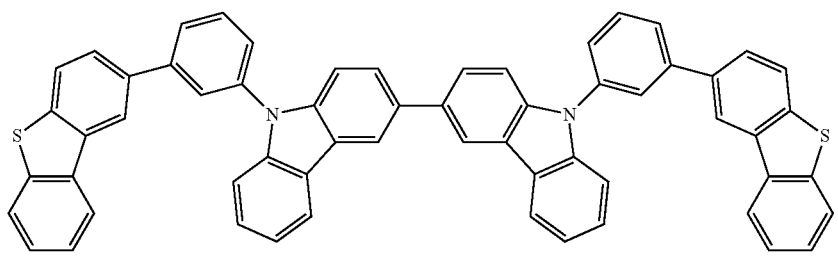
(78)

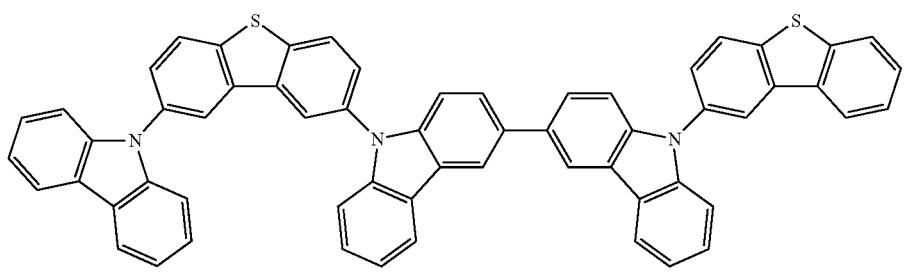
(79)
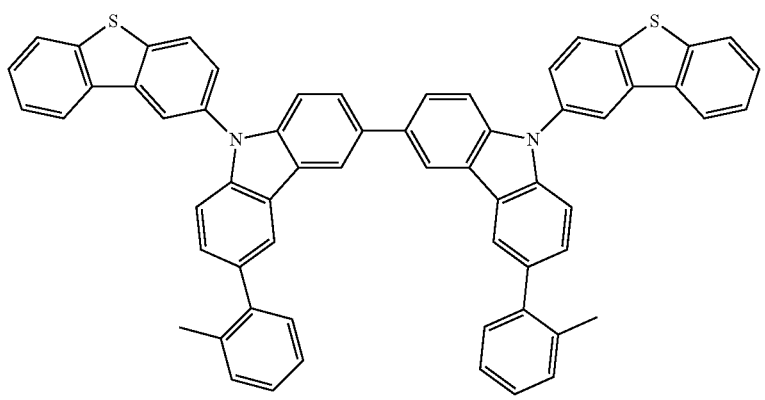
(80)
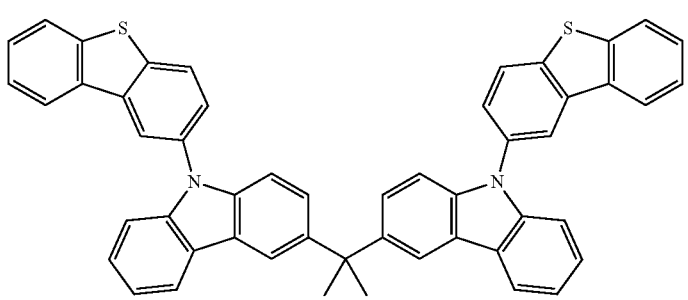
(81)
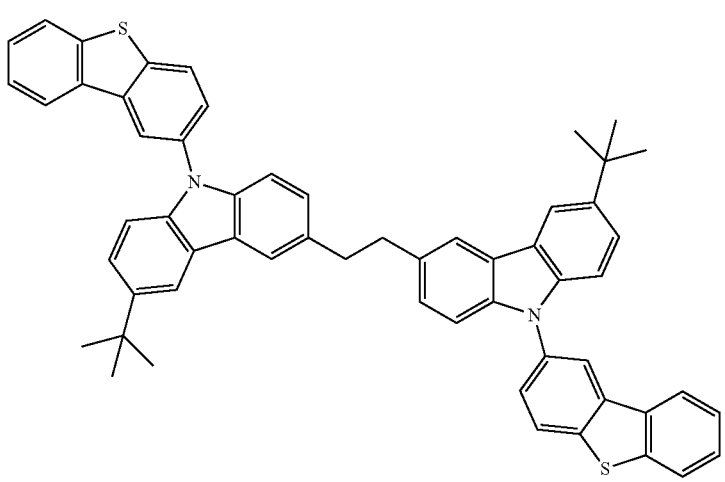
(82)

-continued
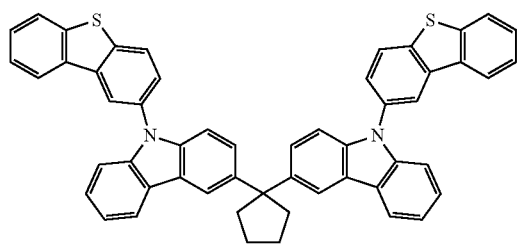
(83)
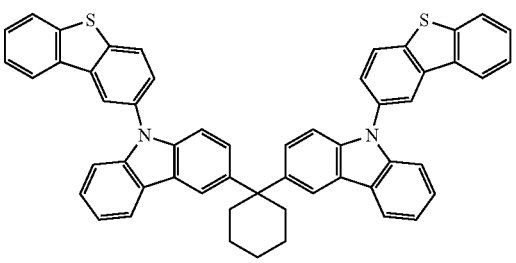
(84)
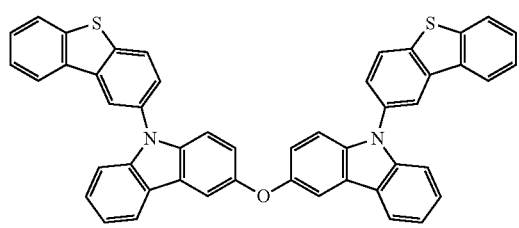
(85)
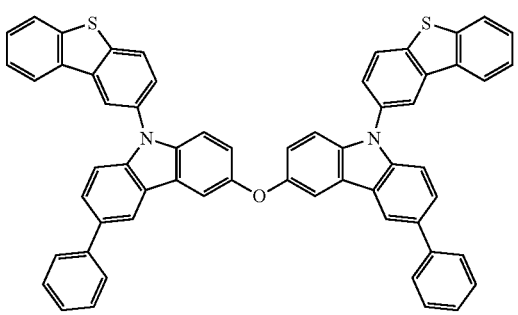
(86)
[Chem. 12]
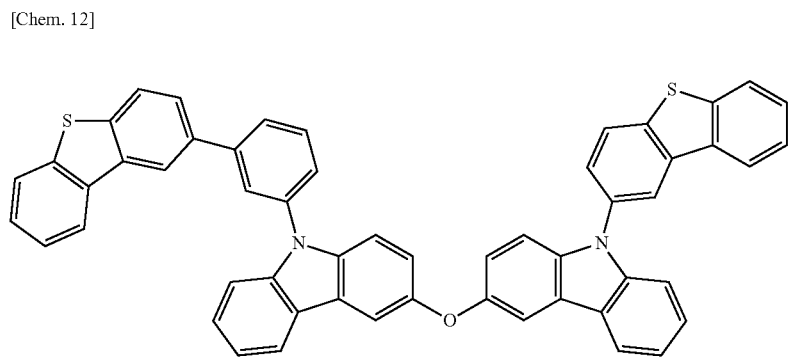
(87)
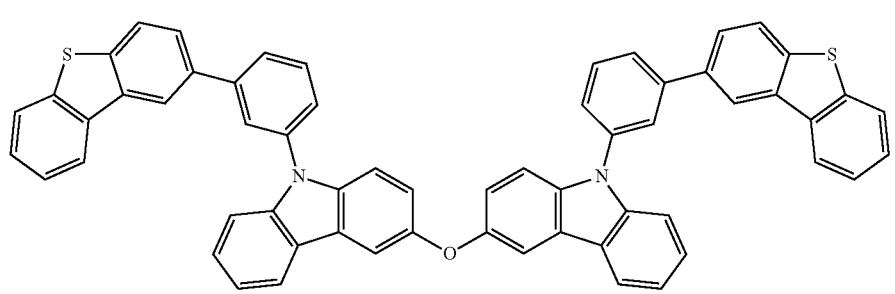
(88)
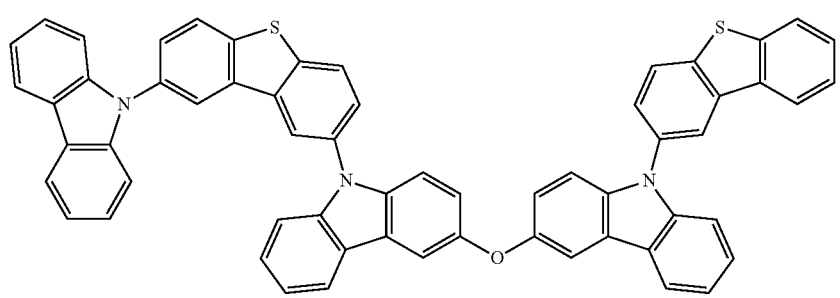
(89)

-continued
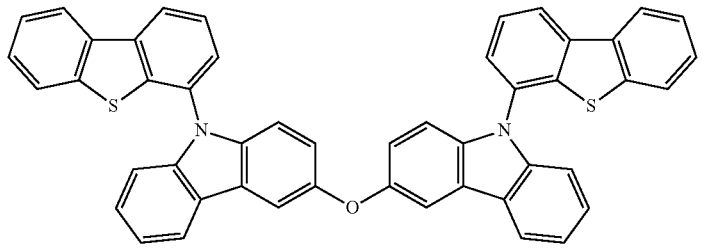
(90)
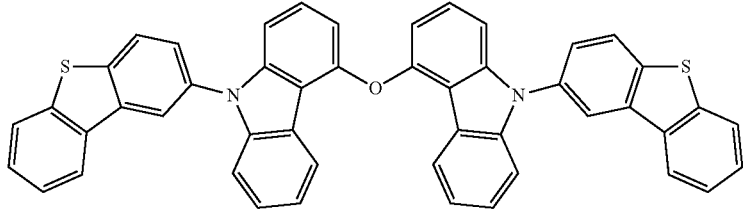
(91)
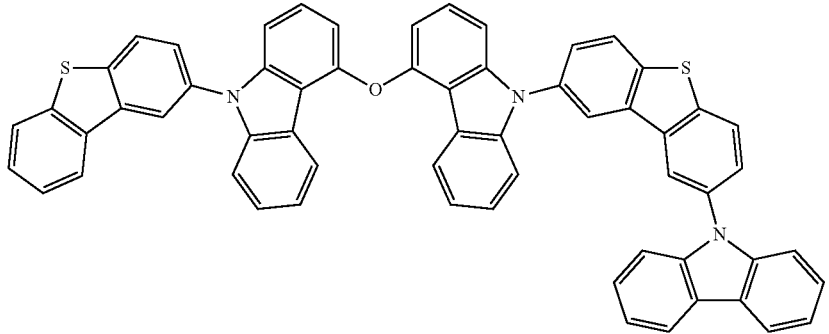
(92)
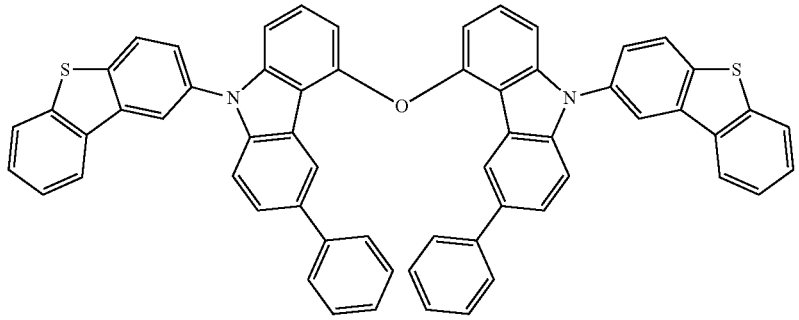
(93)
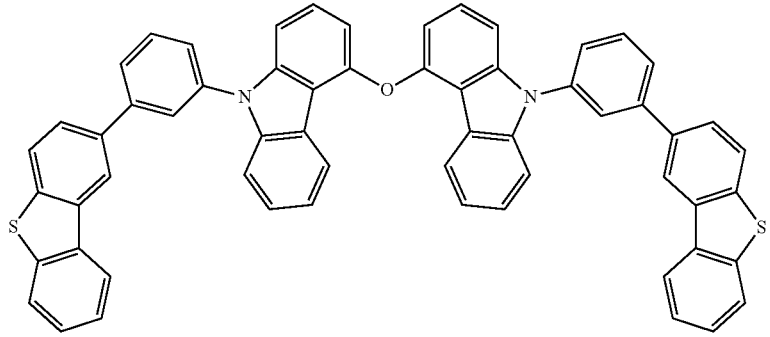
(94)

-continued
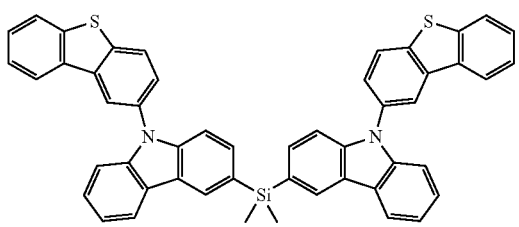
(95)
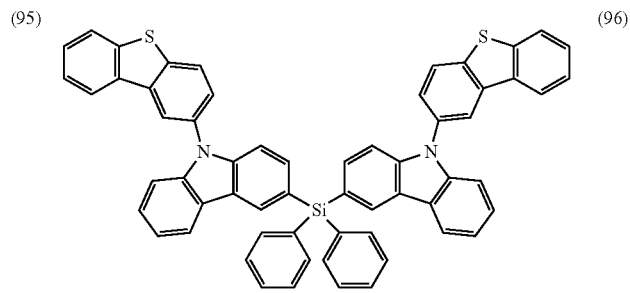
(96)
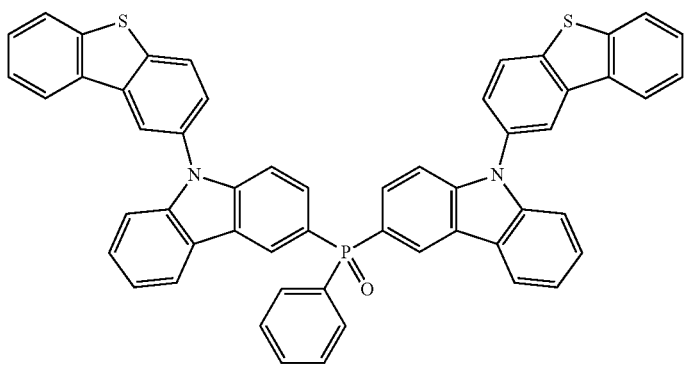
(97)
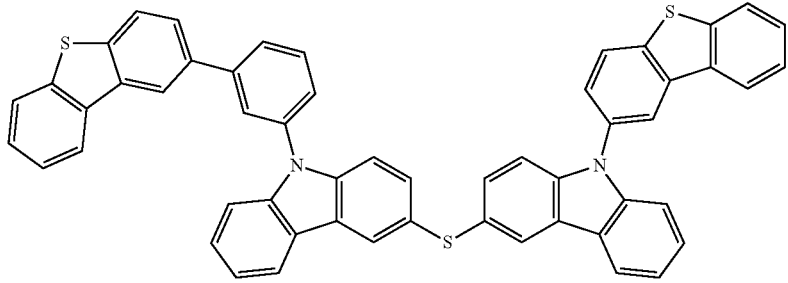
(98)
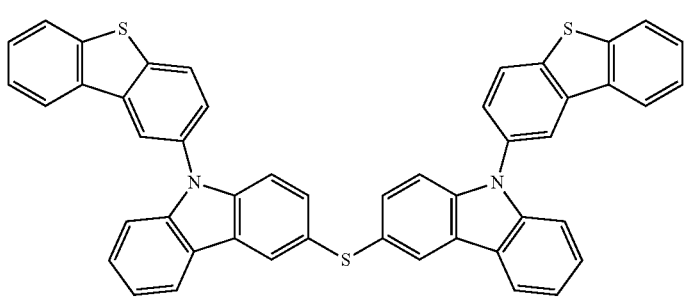
(99)
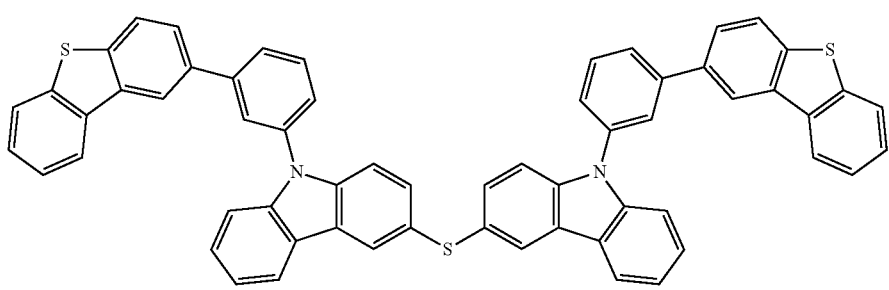
(100)

-continued
(101)
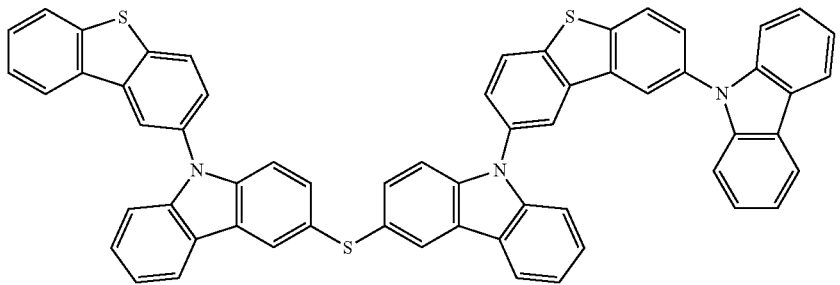
(102)
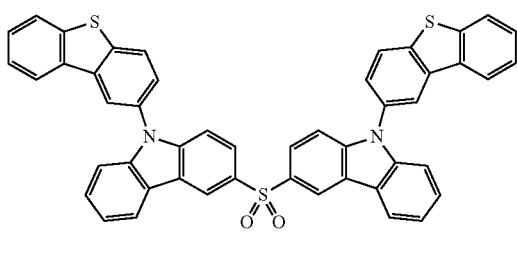
(103)
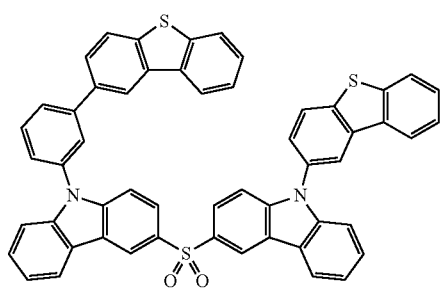
[Chem. 13]
(104)
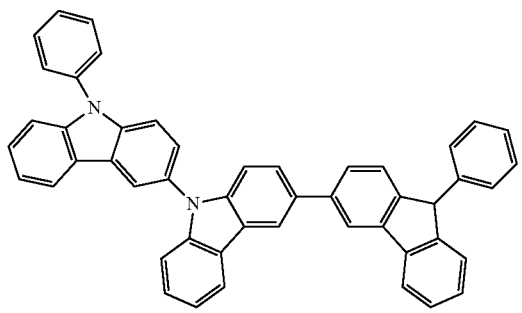
(105)
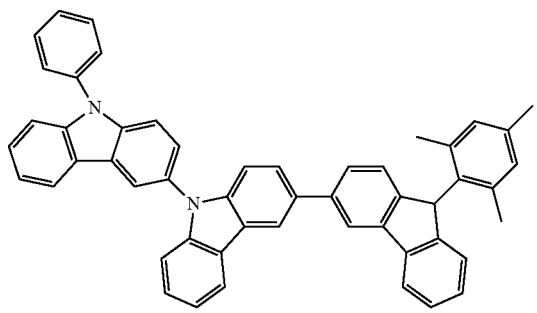
(106)
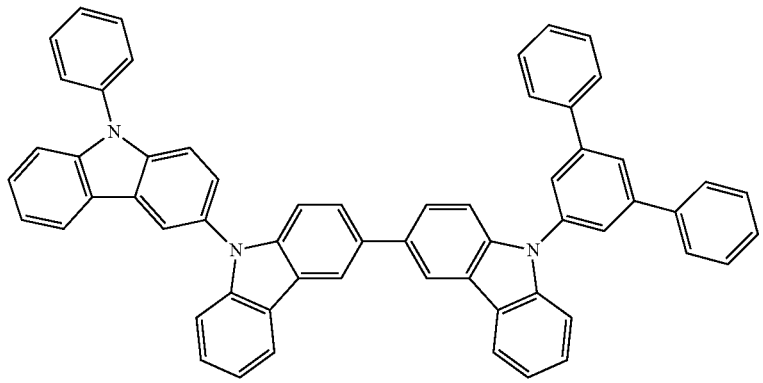

(107)
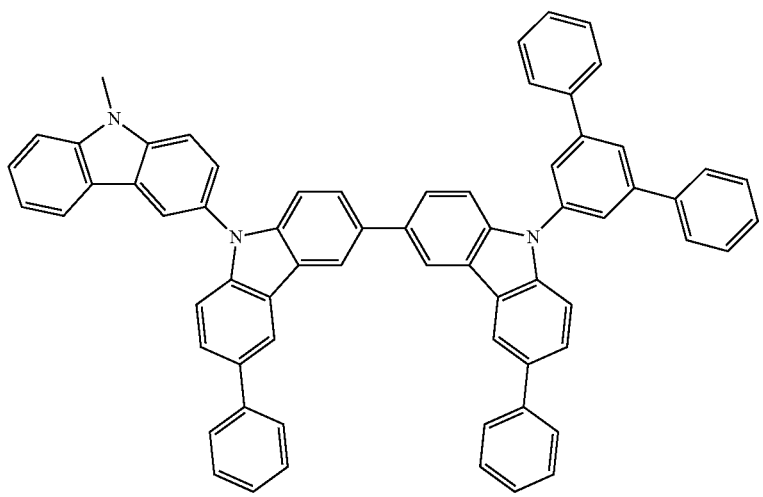
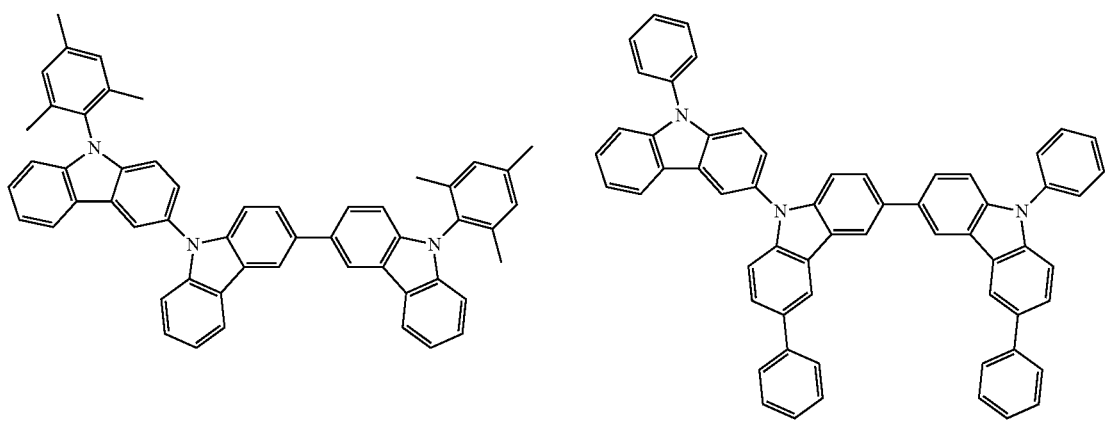
(108)             (109)
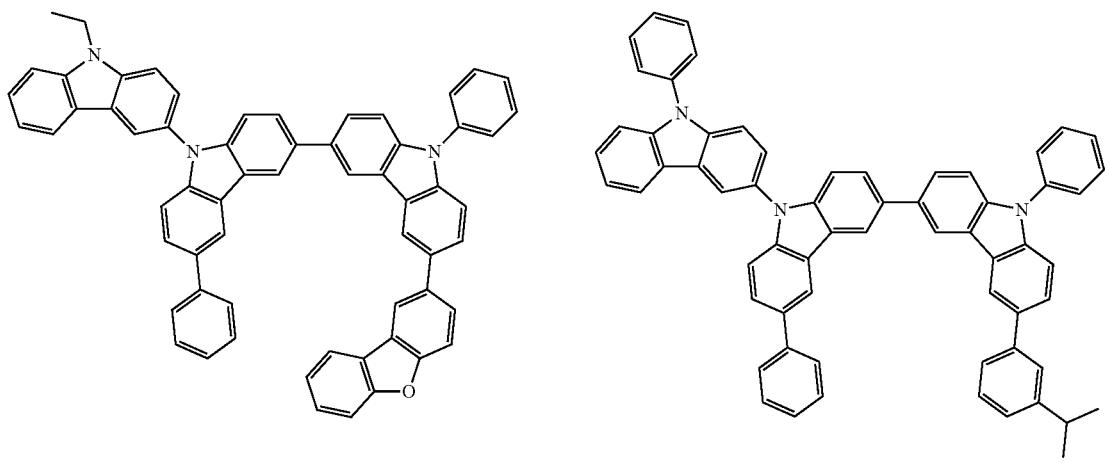
(110)             (111)

-continued
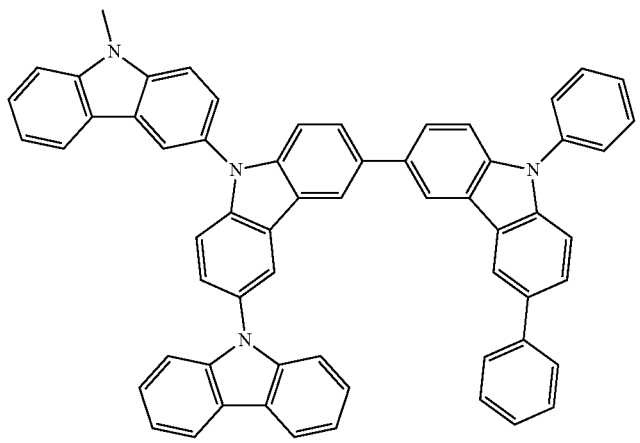
(112)
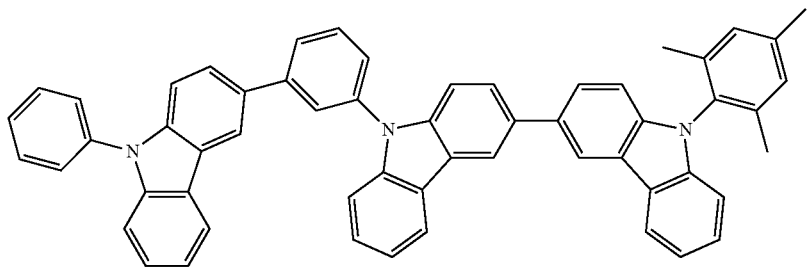
(113)
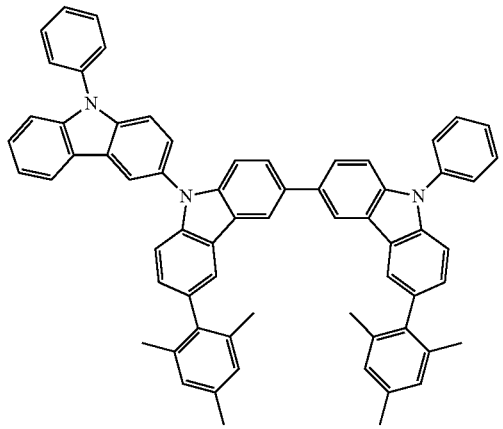
(114)
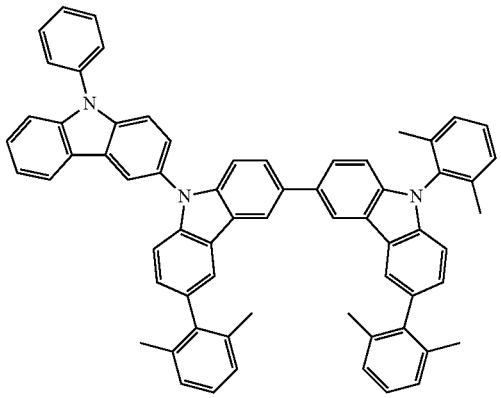
(115)
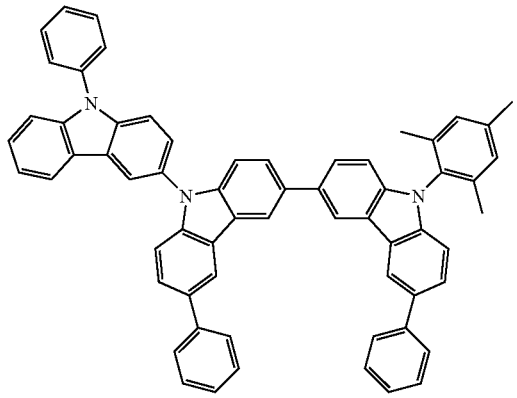
(116)
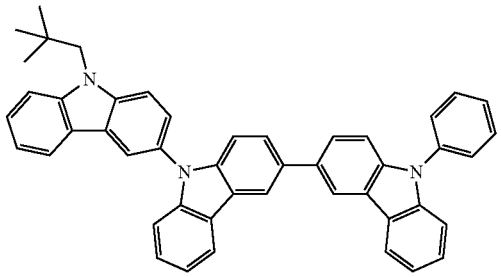
(117)

(118)
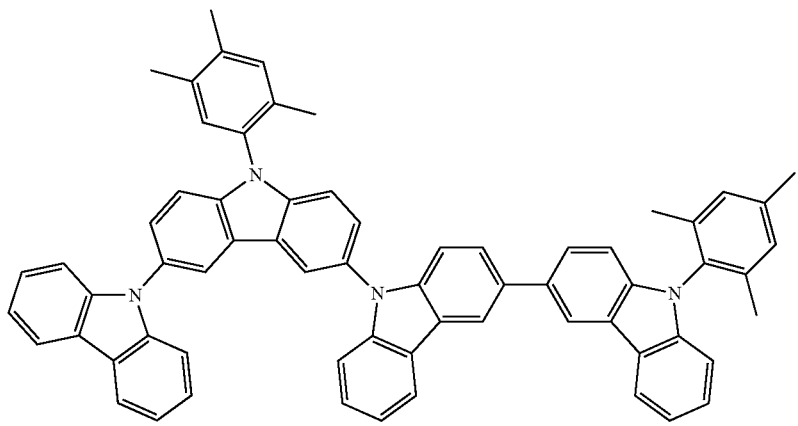
(119)
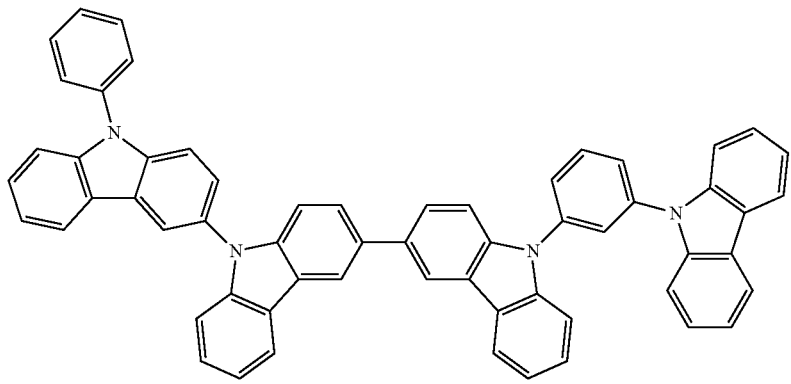
(120)
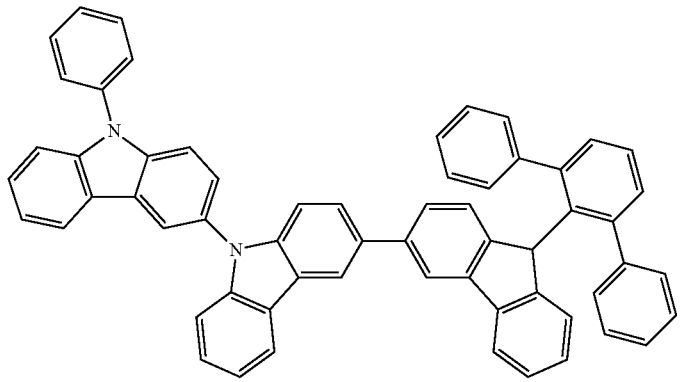
(121)
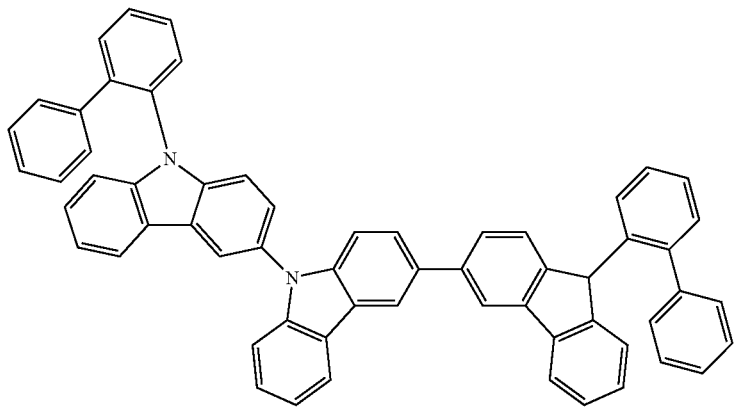

(122)
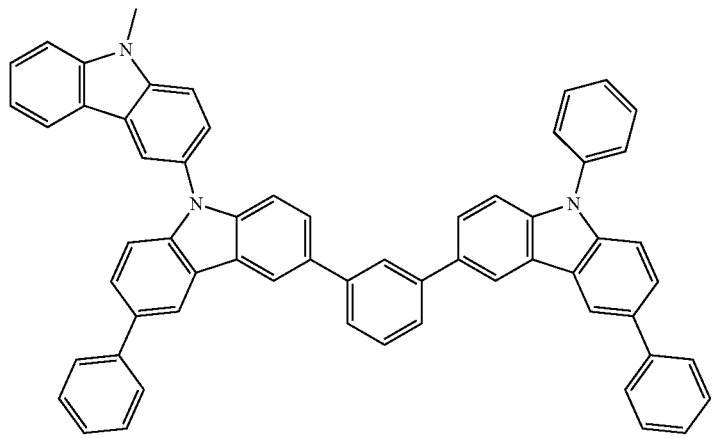
(123)
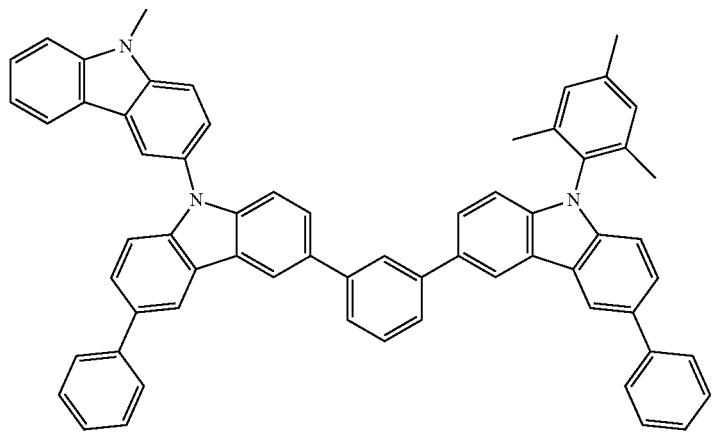
(124)
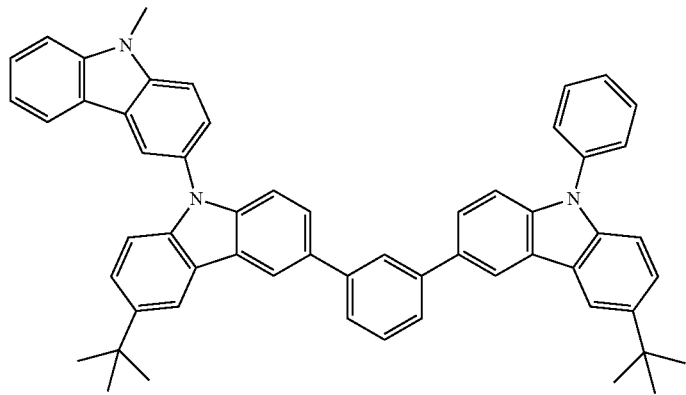

-continued
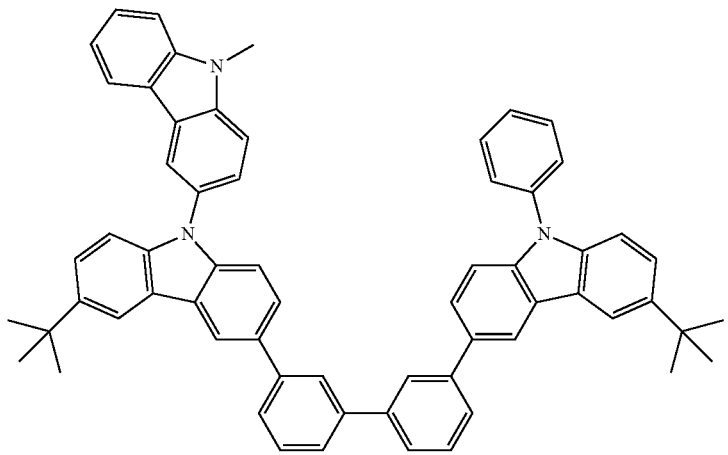
(125)
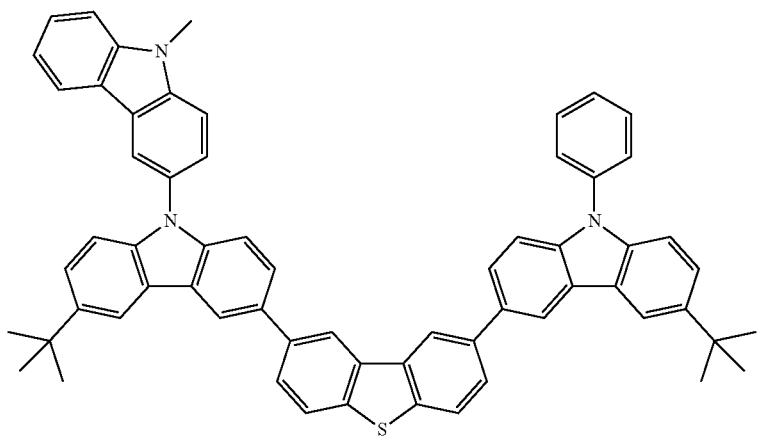
(126)
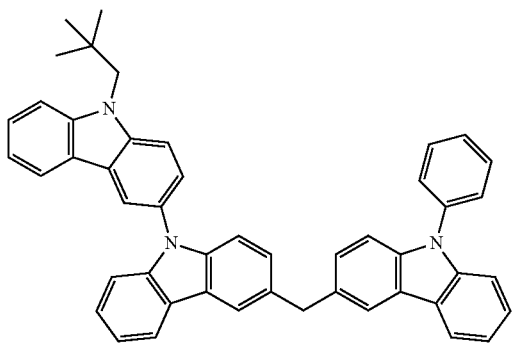
(127)
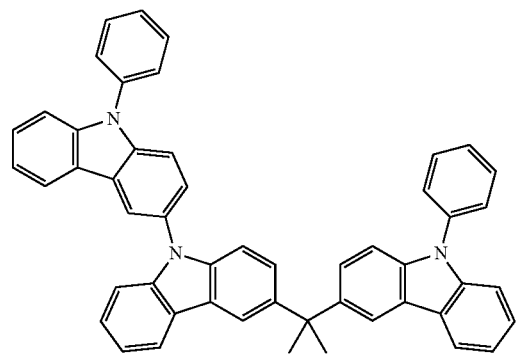
(128)
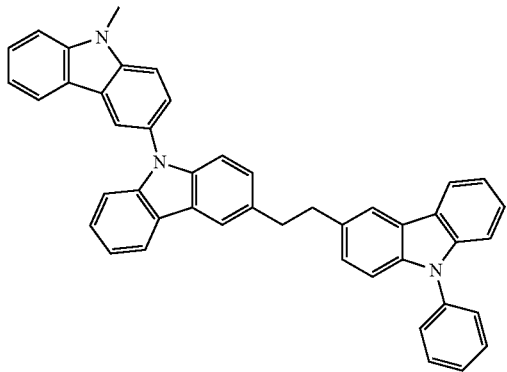
(129)
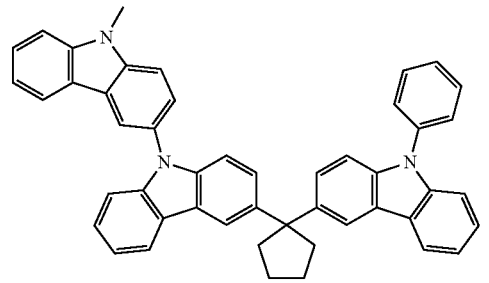
(130)

-continued
(131)
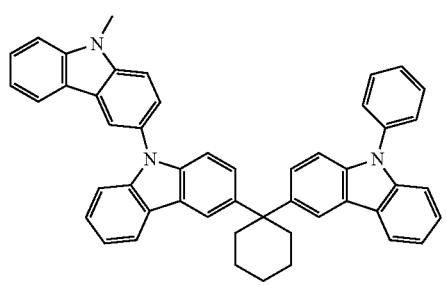
(132)
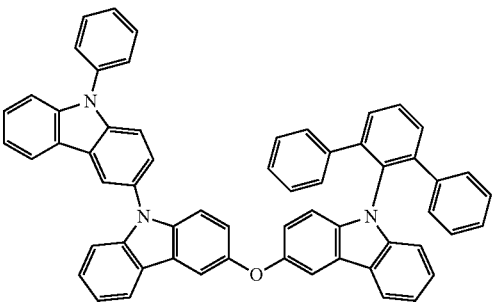
(133)
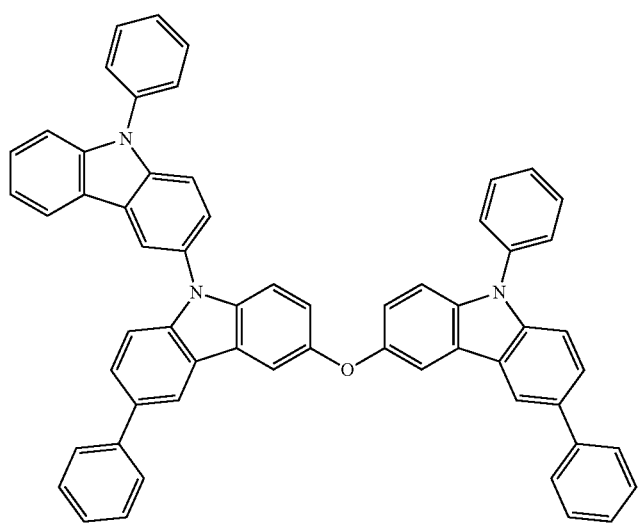
(134)
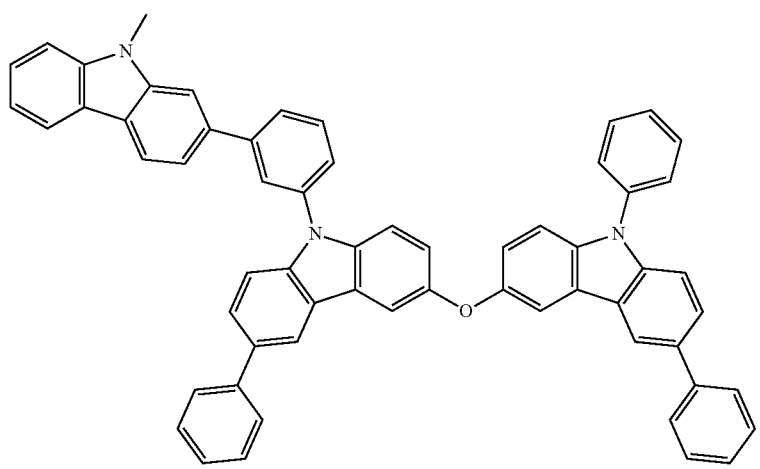

(135)
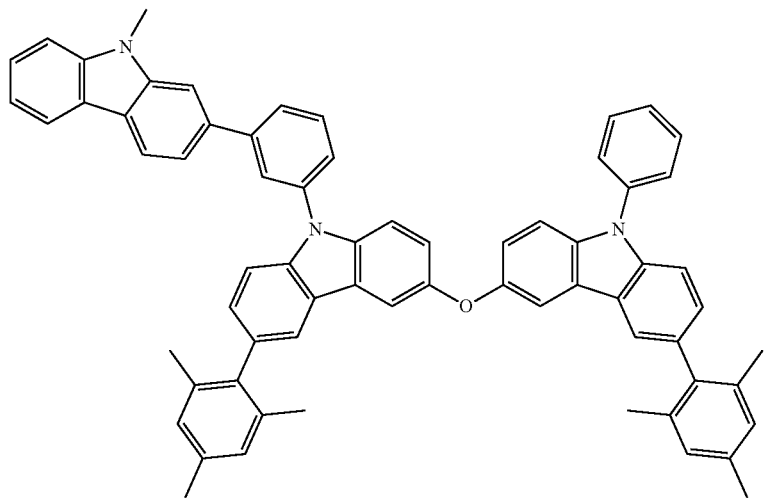
(136)
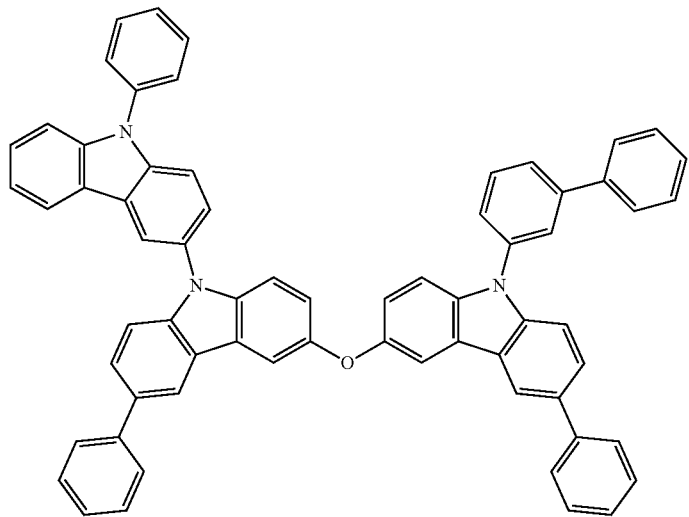
(137)
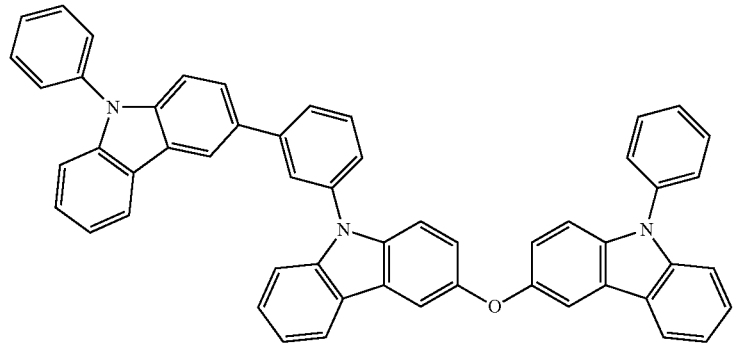

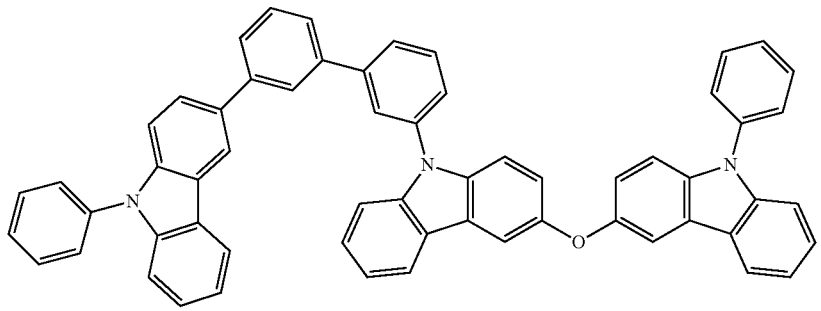
(138)
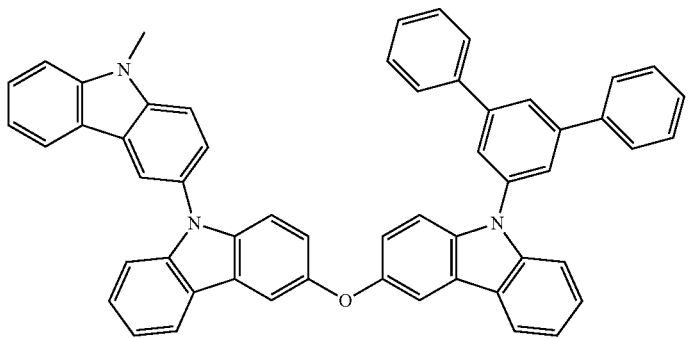
(139)
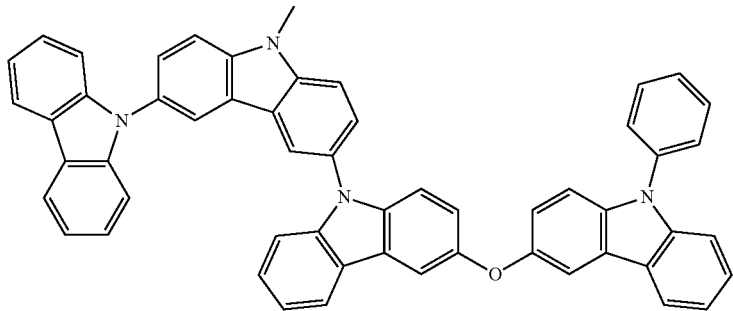
(140)
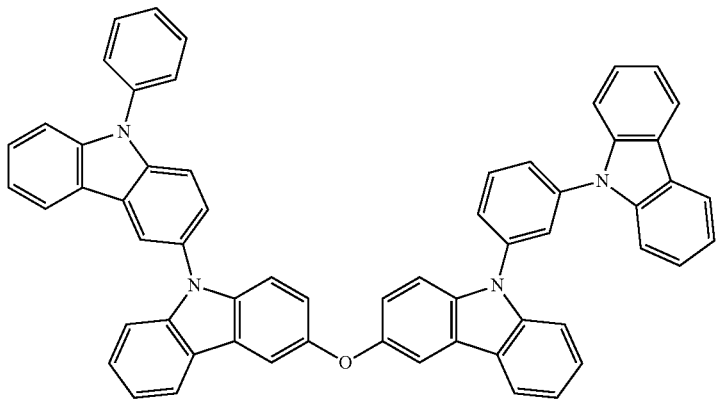
(141)

(142)
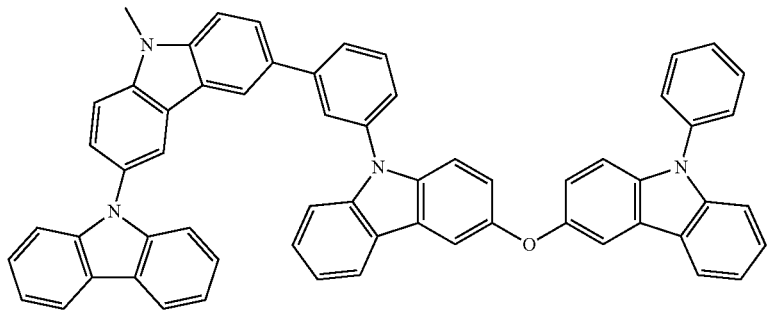
[Chem. 15]
(143)
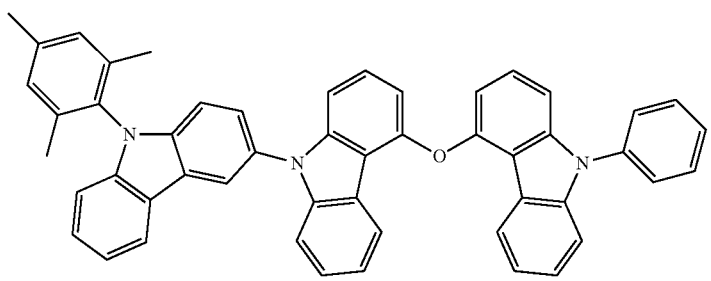
(144)
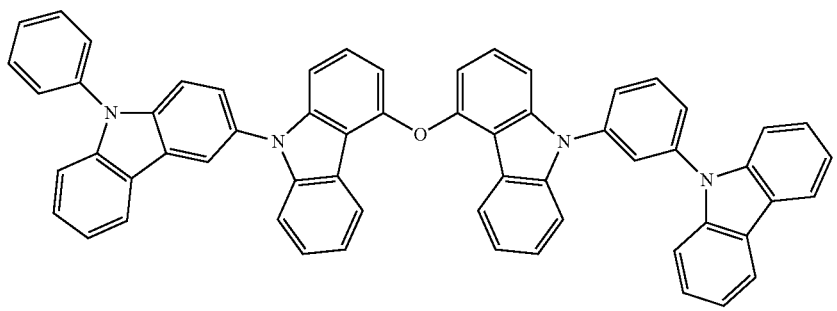
(145)
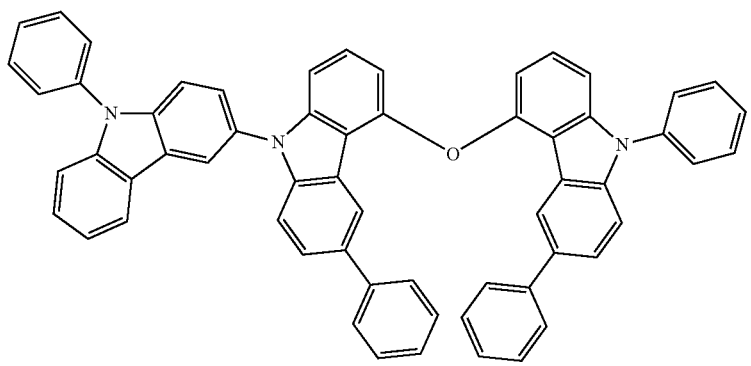

-continued
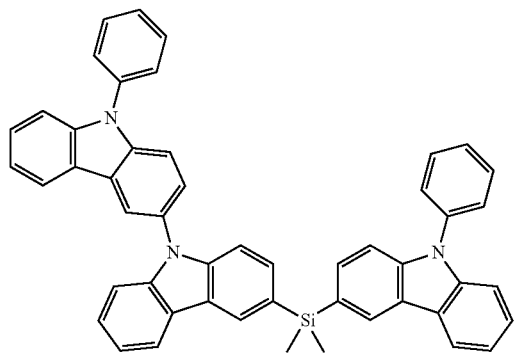
(146)
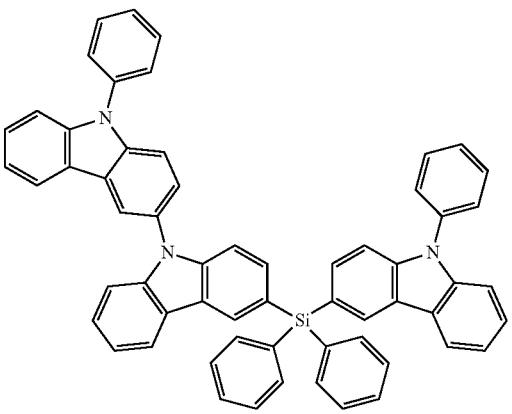
(147)
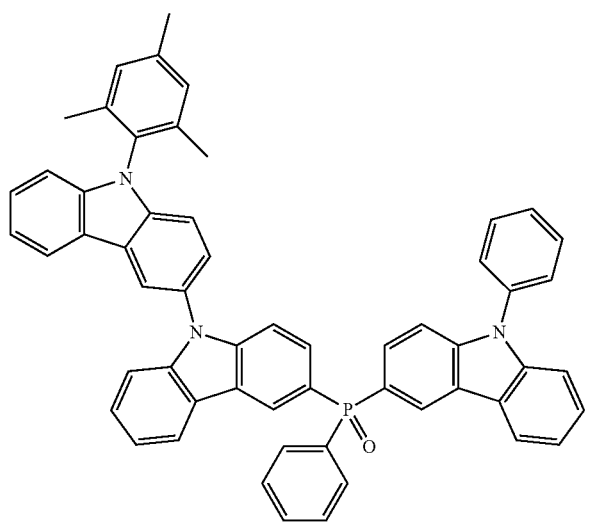
(148)
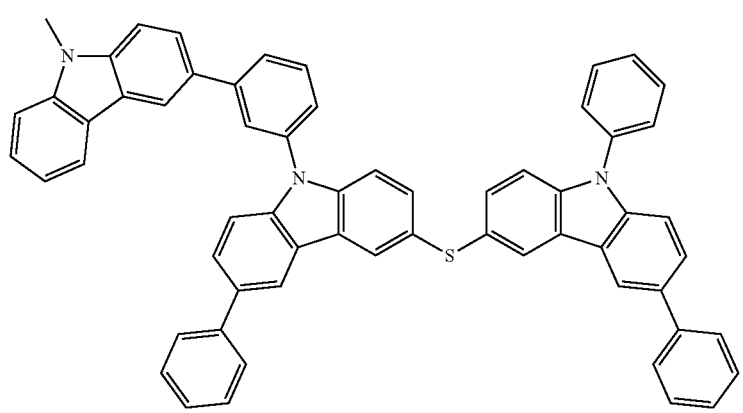
(149)

-continued
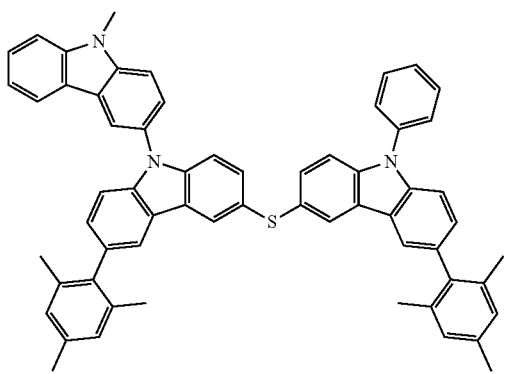
(150)
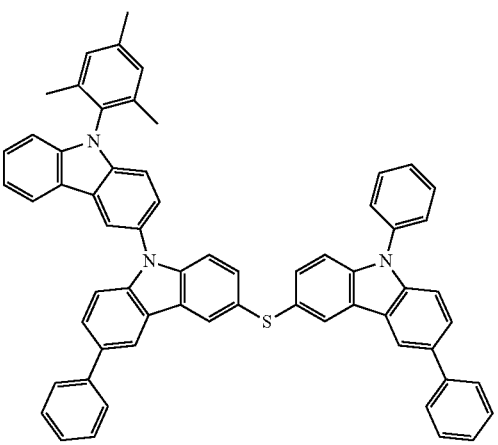
(151)
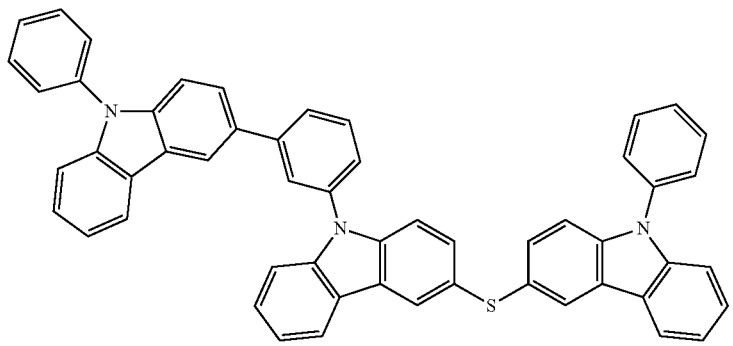
(152)
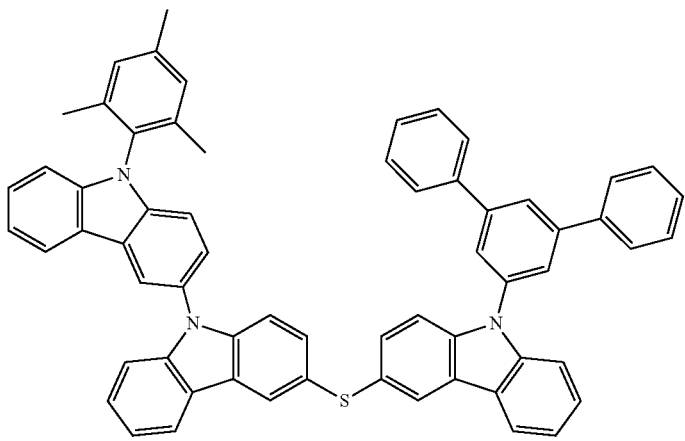
(153)
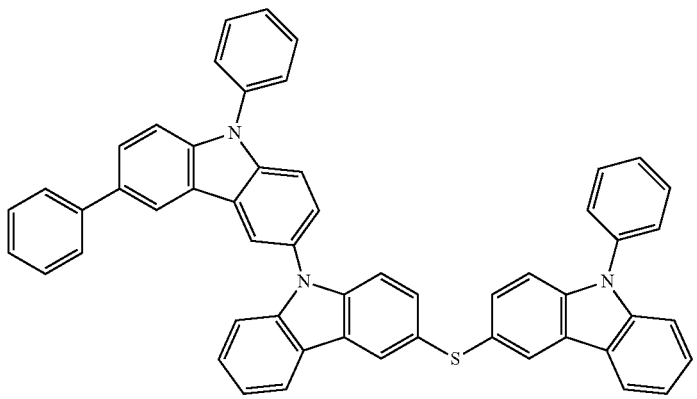
(154)

(155)
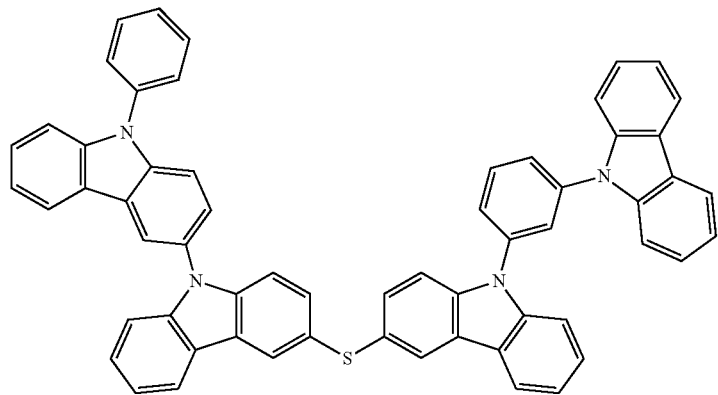
(156)
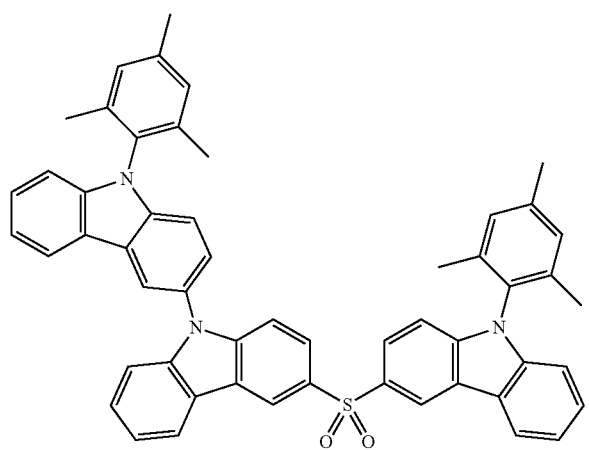
(157)
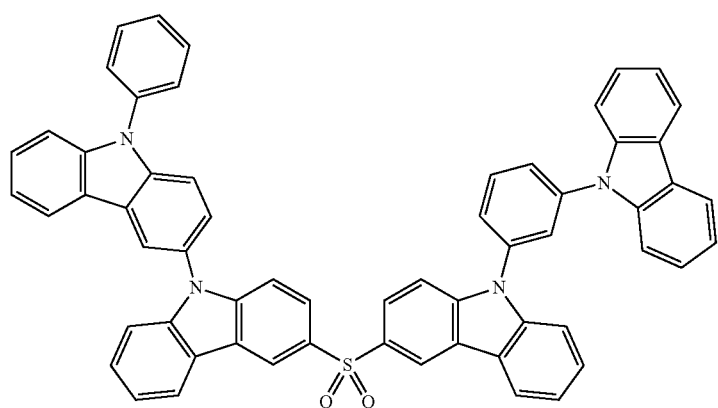

-continued
[Chem.16]
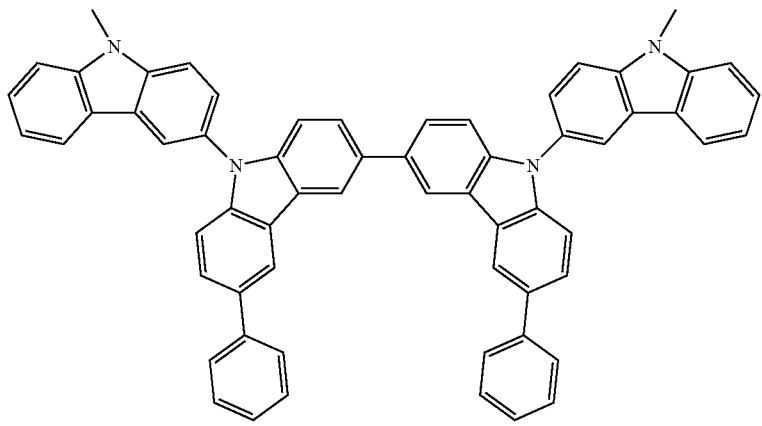
(158)
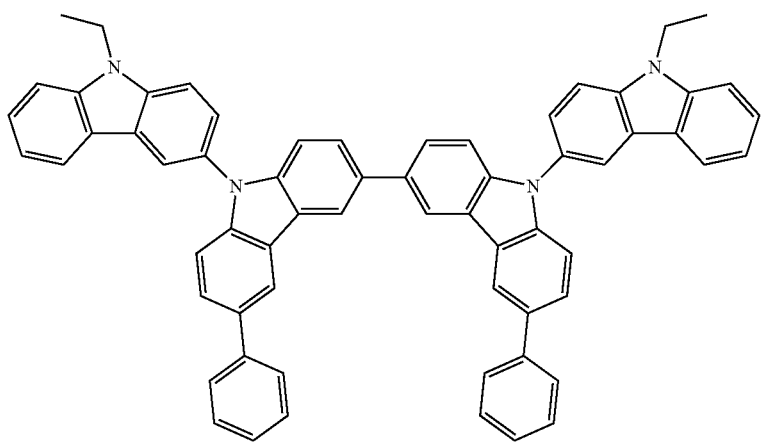
(159)
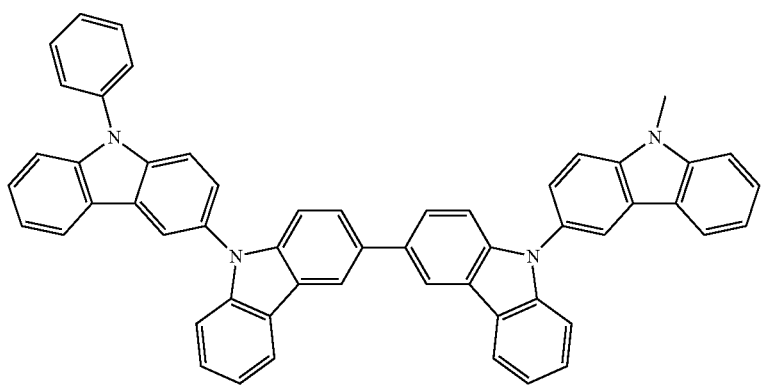
(160)
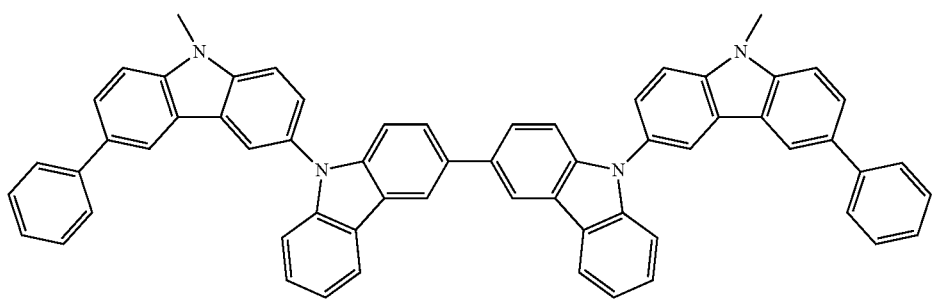
(161)

-continued
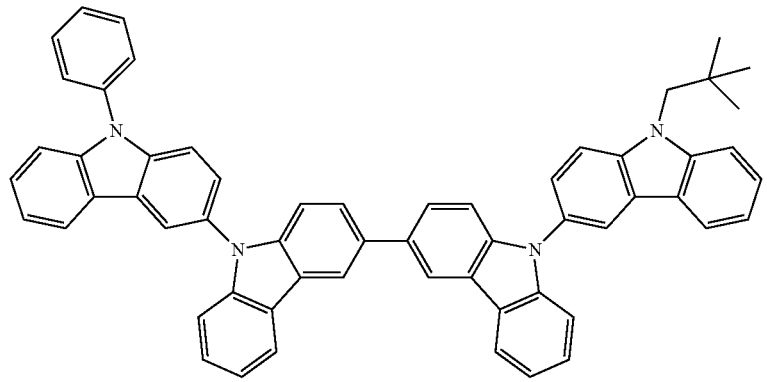
(162)
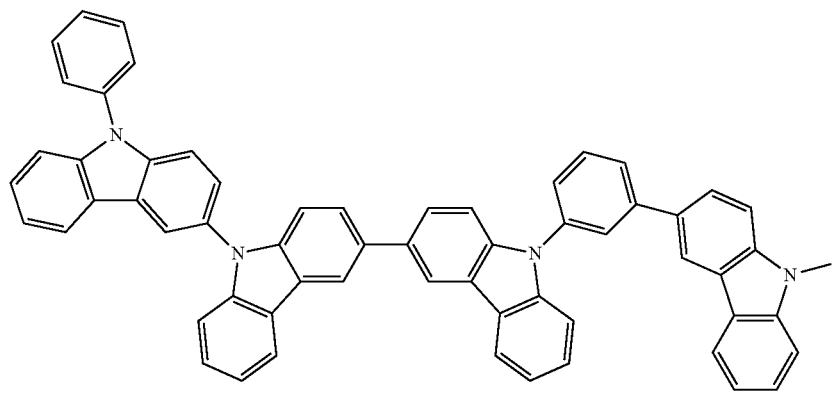
(163)
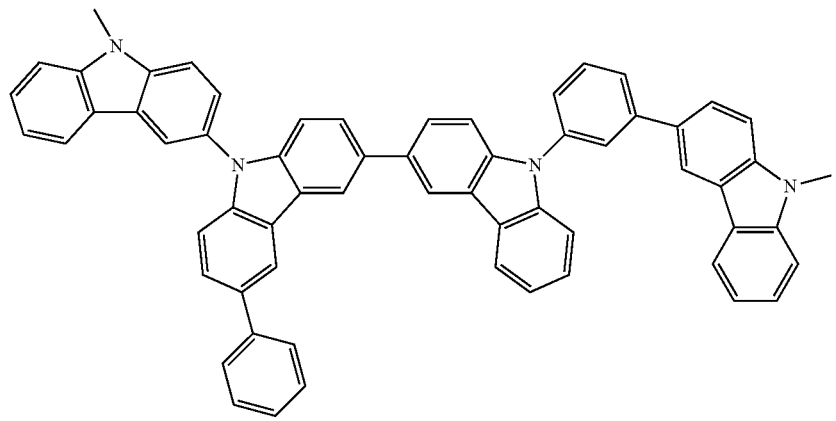
(164)
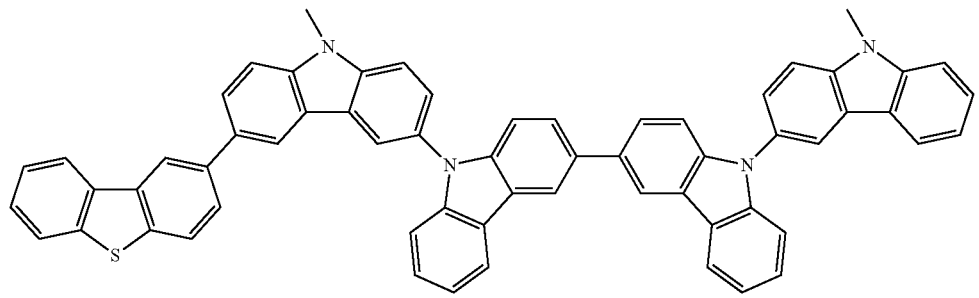
(165)

-continued
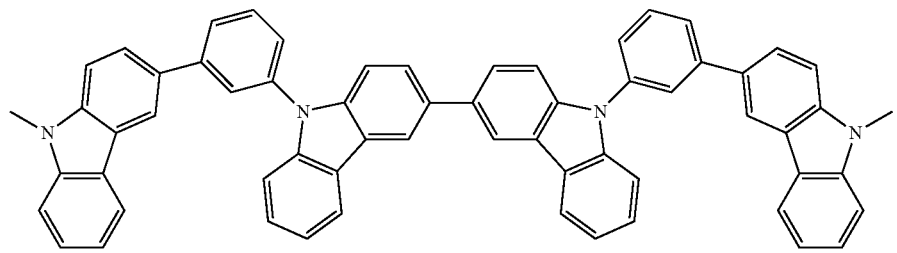
(166)
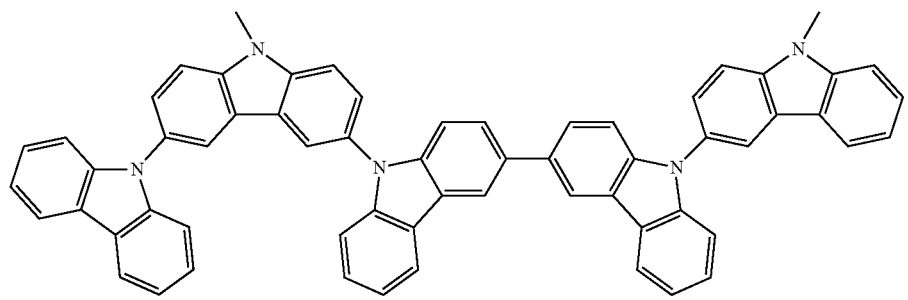
(167)
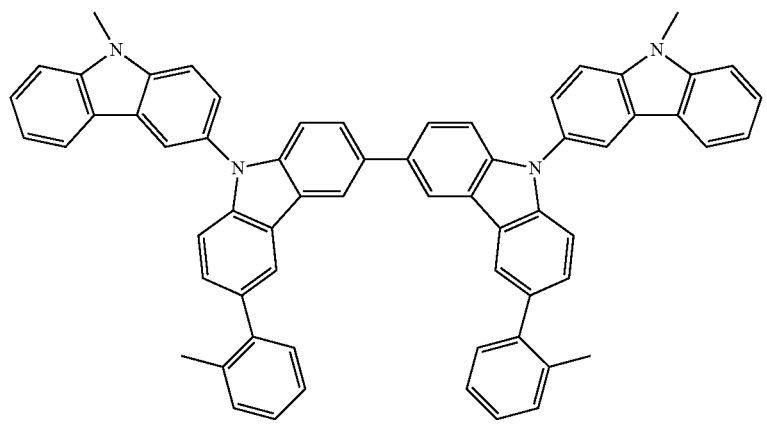
(168)
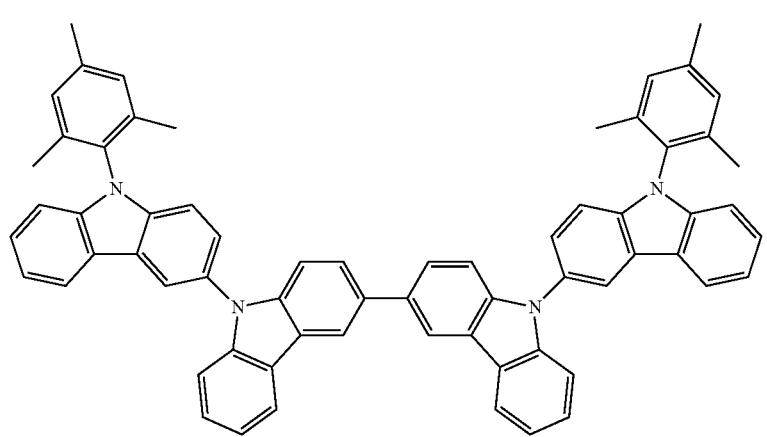
(169)

-continued
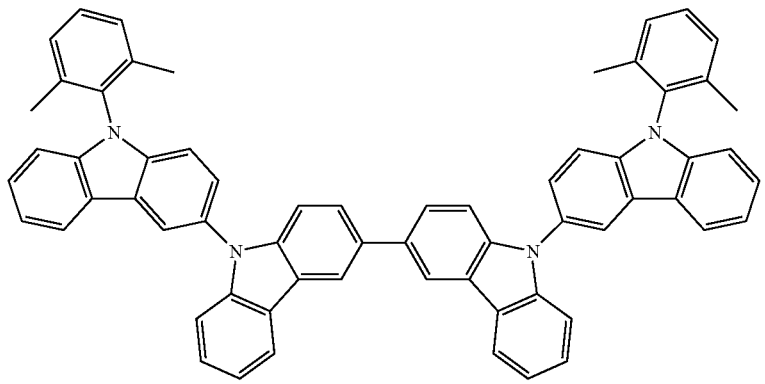
(170)
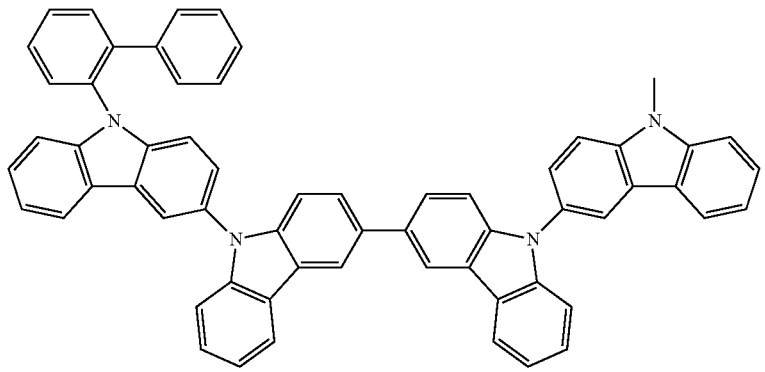
(171)
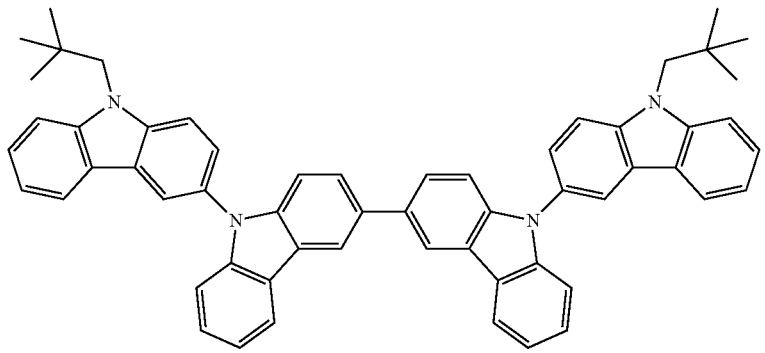
(172)
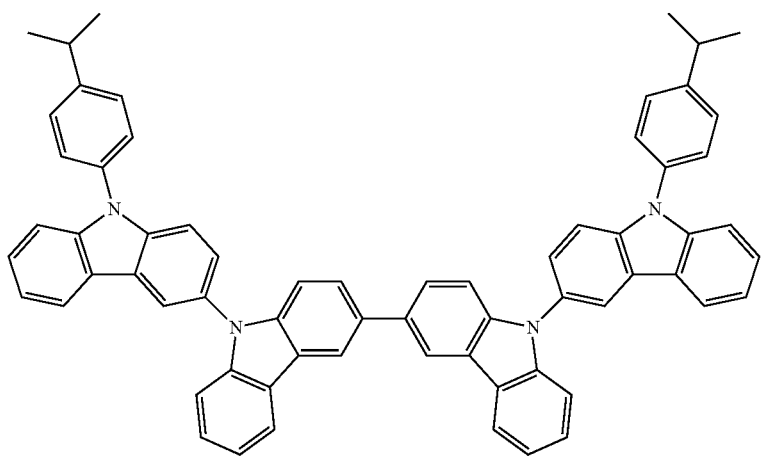
(173)

(174)
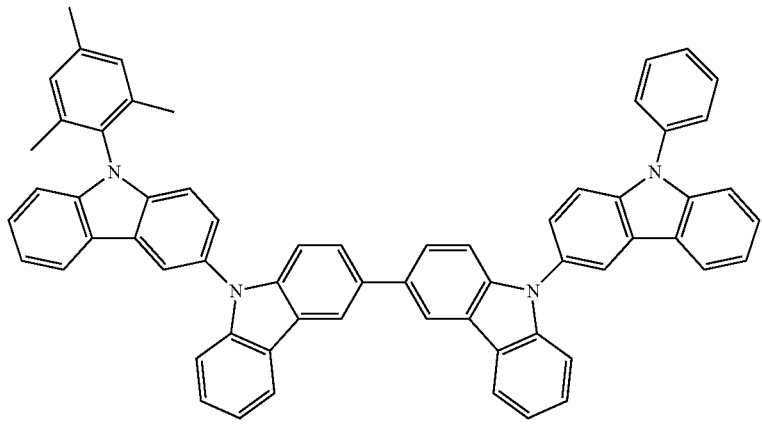
[Chem.17]
(175)
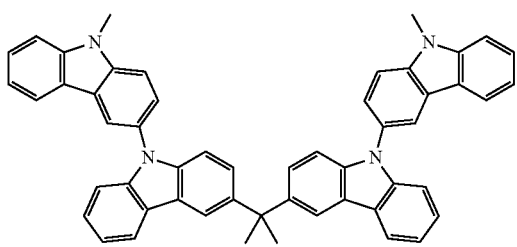
(176)
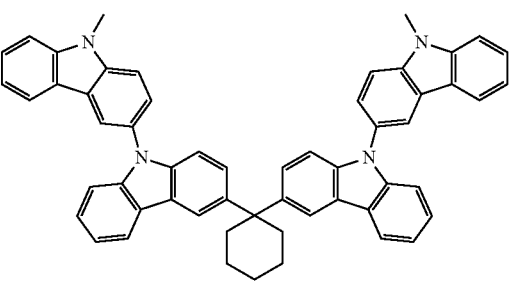
(177)
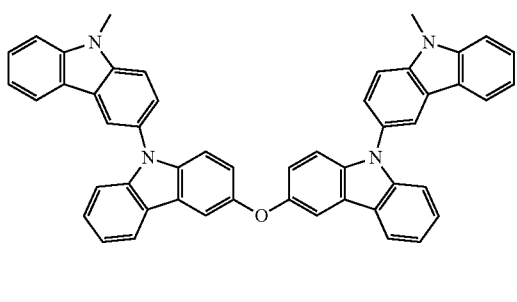
(178)
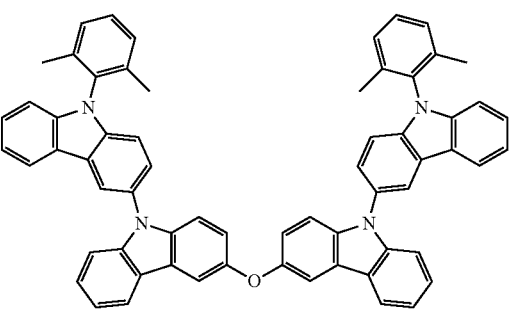
(179)
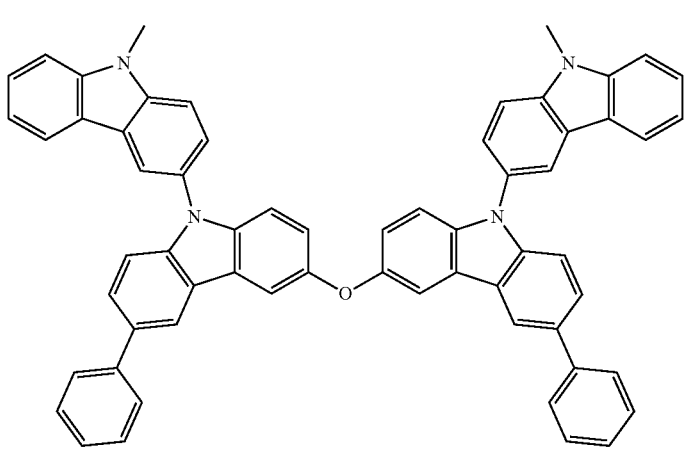

(180)
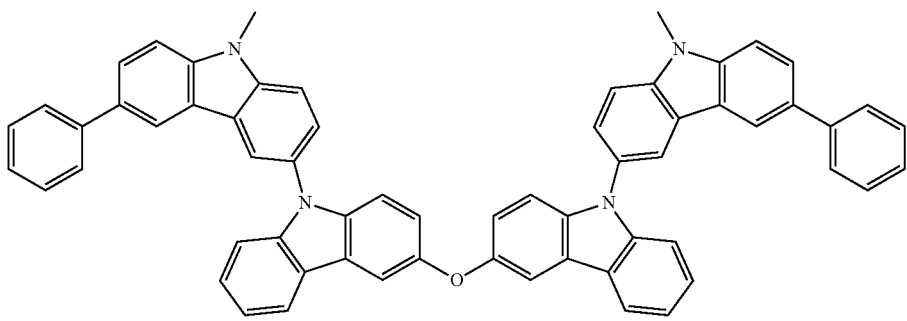
(181)
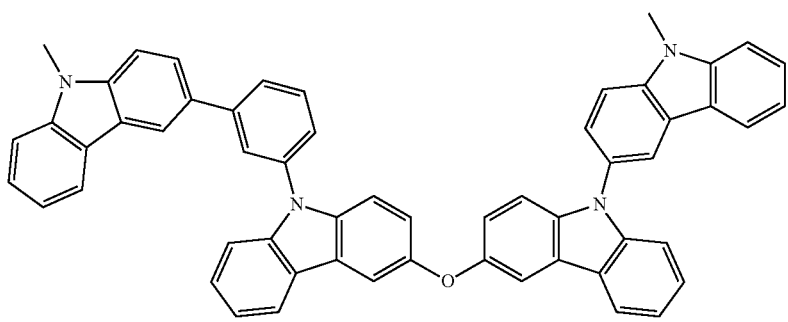
(182)
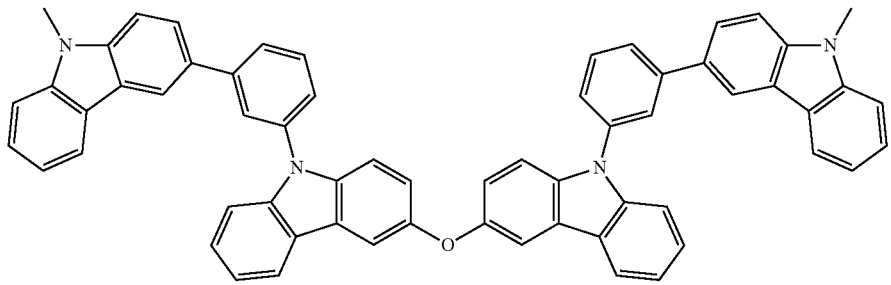
(183)
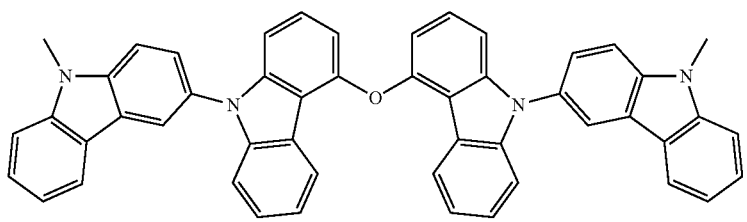
(184)
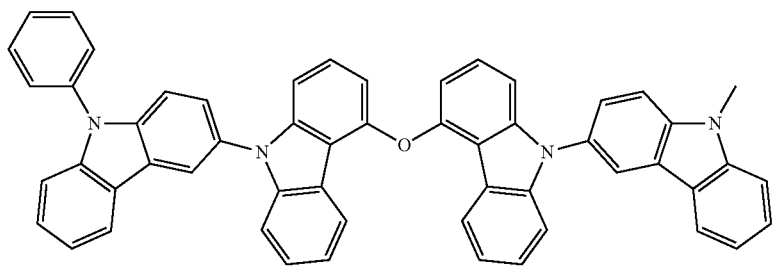

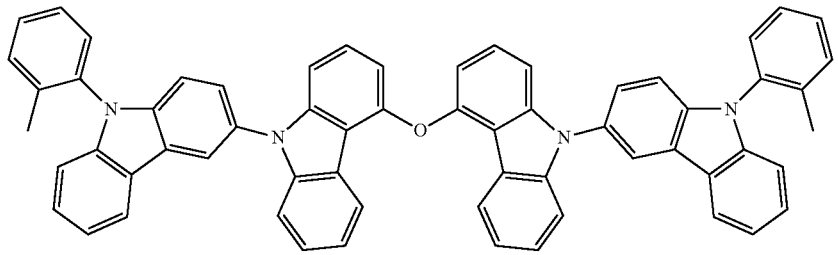
(185)
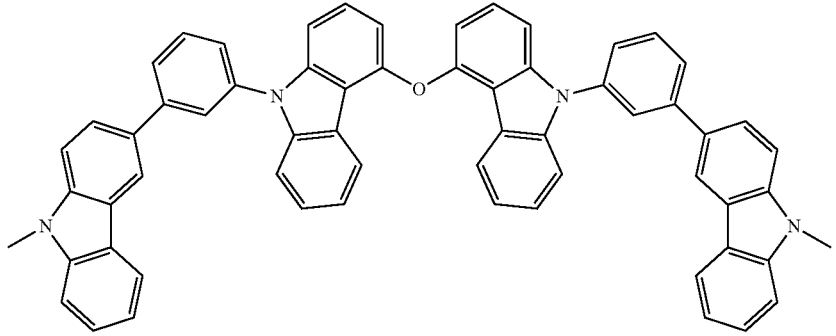
(186)
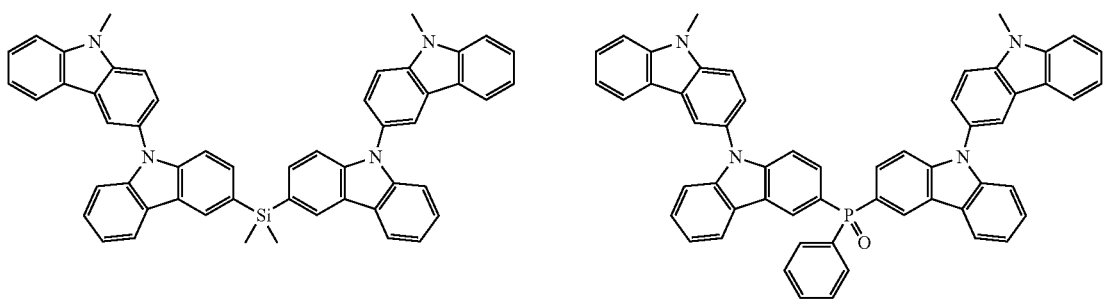
(187) (188)
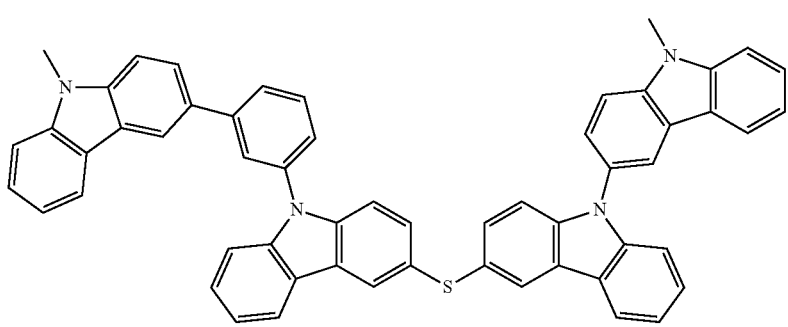
(189)
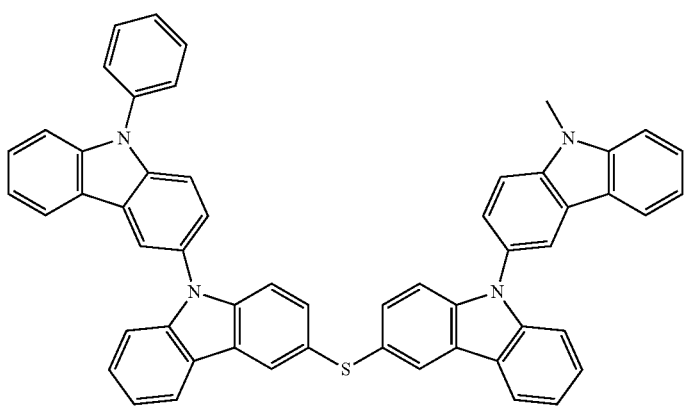
(190)

-continued
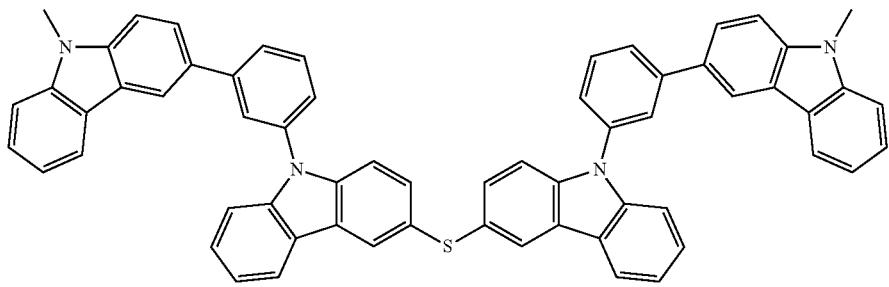
(191)
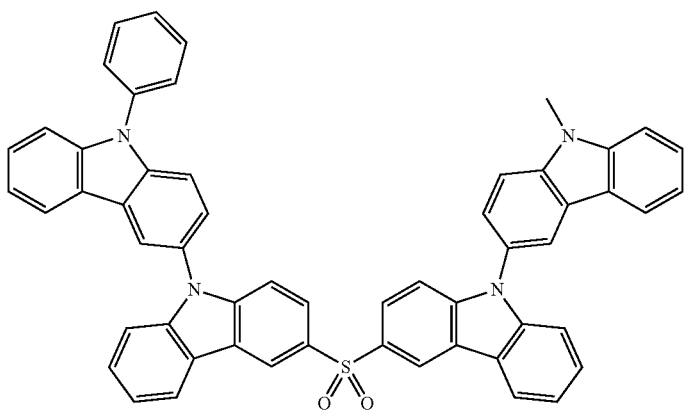
(192)
[Chem. 18]
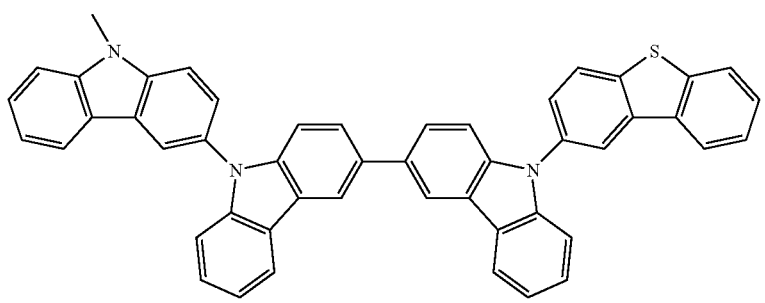
(193)
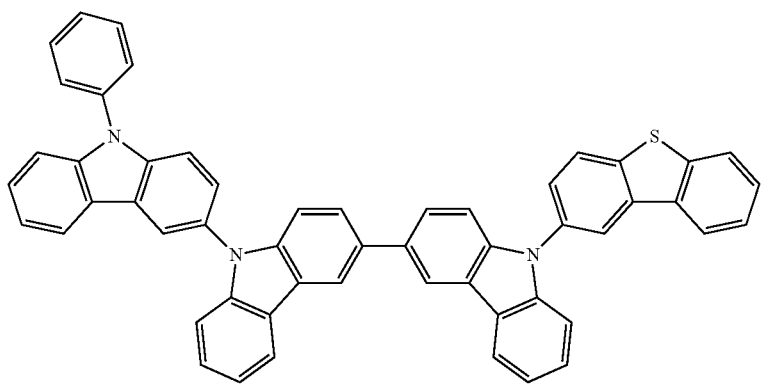
(194)

(195)
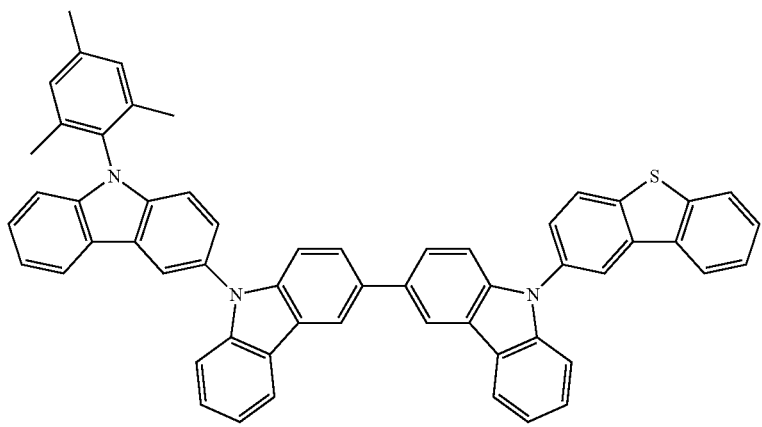
(196)
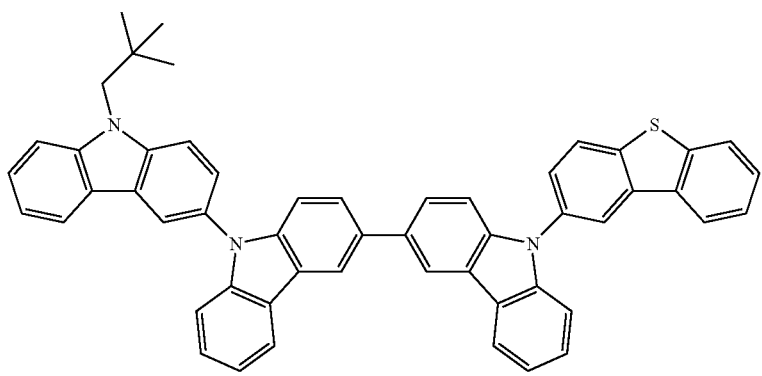
(197)
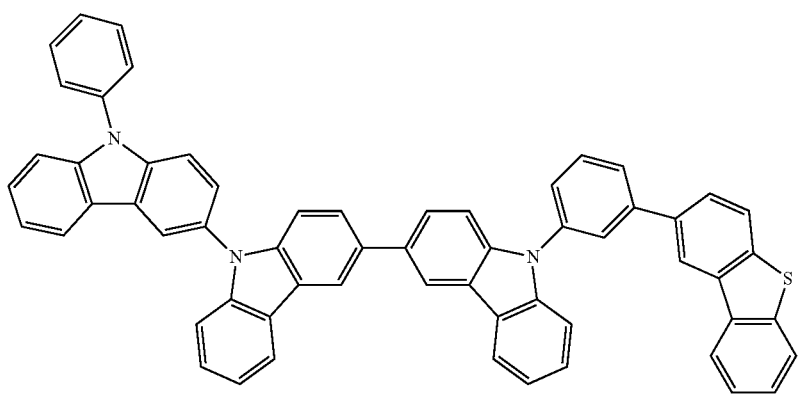
(198)
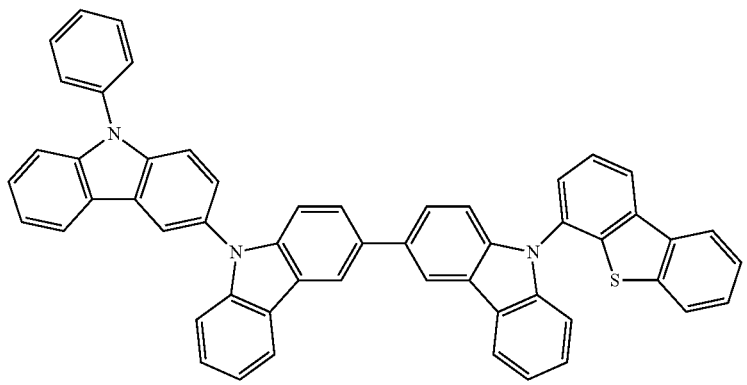

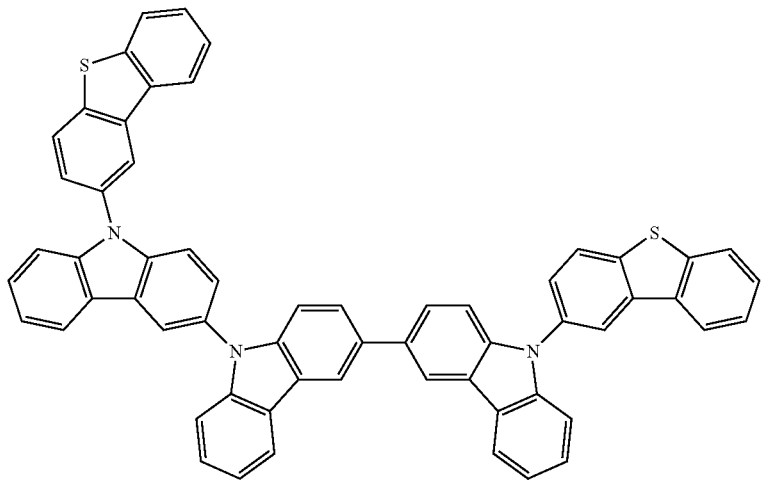
(199)
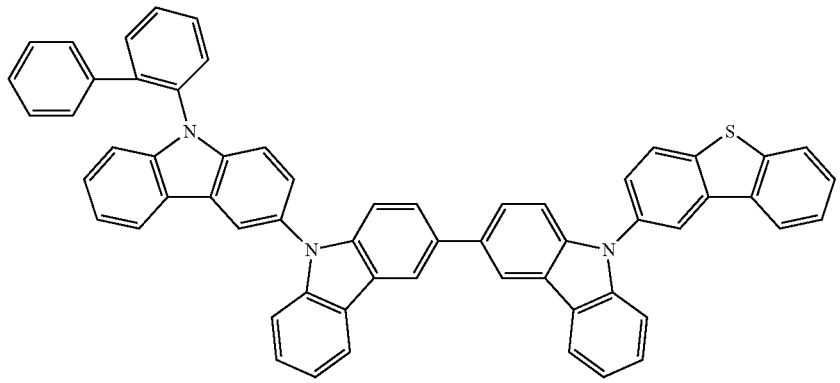
(200)
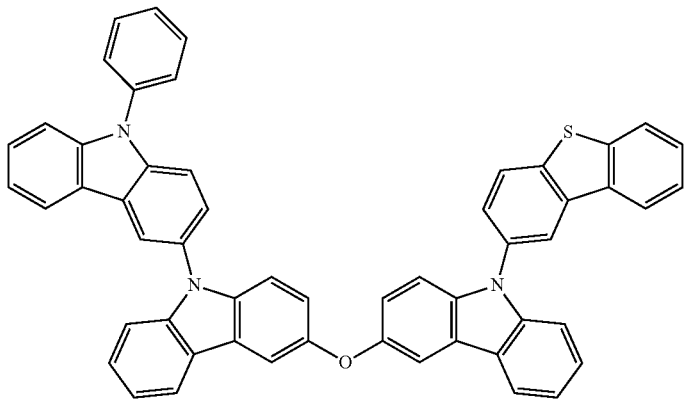
(201)
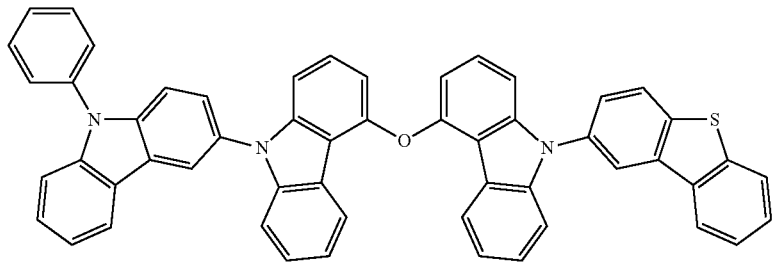
(202)

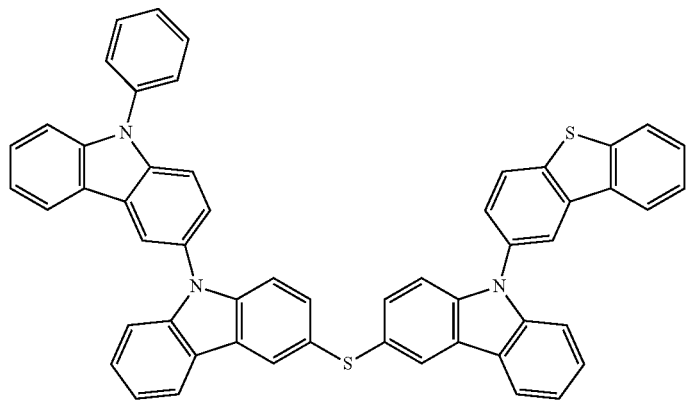

(203)

The material for an organic electroluminescence device of the present invention is preferably a host material to be incorporated into the light emitting layer of an organic EL device.

Next, the organic EL device of the present invention is described.

The organic EL device of the present invention includes one or more organic thin film layers including a light emitting layer between a cathode and an anode, in which at least one layer of the organic thin film layers contains the material for the organic electroluminescence device of the present invention.

A multi-layer type organic EL device is obtained by laminating a plurality of layers; for example, the device is formed of an anode, a hole transporting layer (a hole injecting layer), a light emitting layer, and a cathode, of an anode, a light emitting layer, an electron transporting layer (an electron injecting layer), and a cathode, of an anode, a hole transporting layer (a hole injecting layer), a light emitting layer, an electron transporting layer (an electron injecting layer), and a cathode, or of an anode, a hole transporting layer (a hole injecting layer), a light emitting layer, a hole barrier layer, an electron transporting layer (an electron injecting layer), and a cathode. It should be noted that in the present invention, "a hole injecting/transporting layer" is included in an aspect of a hole transporting layer.

In the organic EL device of the present invention, the light emitting layer preferably contains the material for an organic electroluminescence device represented by the general formula (1) as a host material, and more preferably further contains a phosphorescent light emitting material. In addition, when the organic EL device of the present invention has a hole transporting layer (hole injecting layer), the material for an organic electroluminescence device of the present invention can be preferably incorporated into the hole transporting layer (hole injecting layer).

The phosphorescent light emitting material is preferably a compound containing a metal selected from iridium (Ir), osmium (Os), and platinum (Pt) because the compound has a high phosphorescent quantum yield, and can additionally improve the external quantum efficiency of the light emitting device. The material is more preferably a metal complex such as an iridium complex, an osmium complex, or a platinum complex. Of those, the iridium complex and the platinum complex are still more preferred. The metal complex is preferably an orthometalated metal complex in which a central metal atom and a carbon atom in a ligand are orthometalbonded, and is more preferably an orthometalated iridium complex. More preferred forms of the orthometalated metal complex include the following iridium complexes.

[Chem. 19]

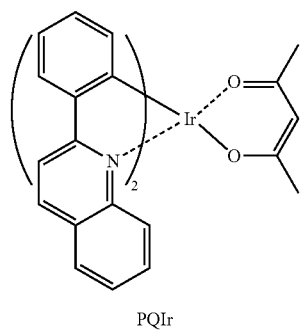

PQIr

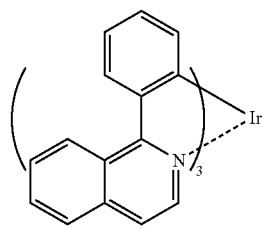

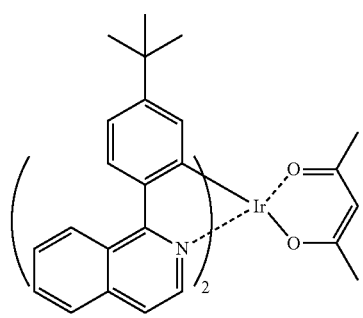

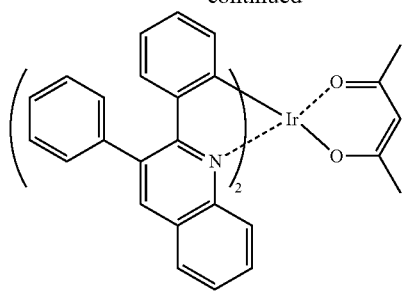
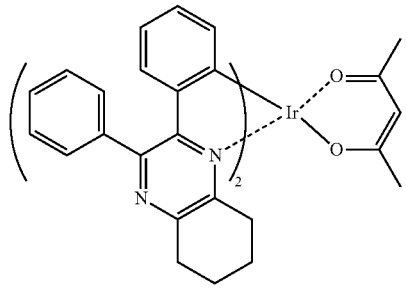
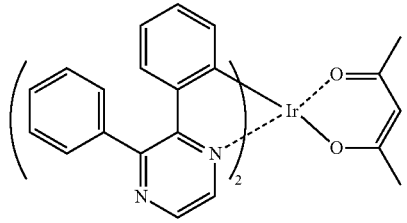
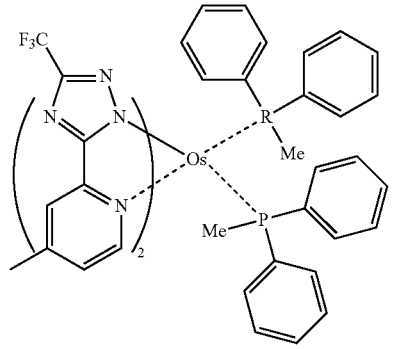
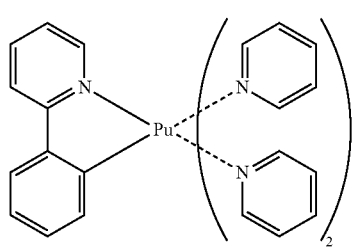
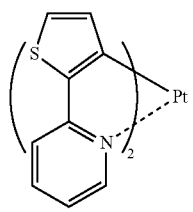
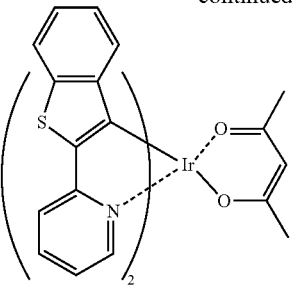
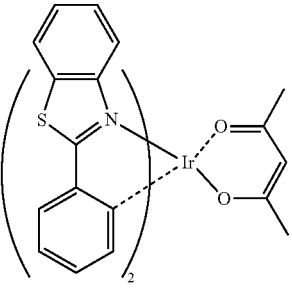
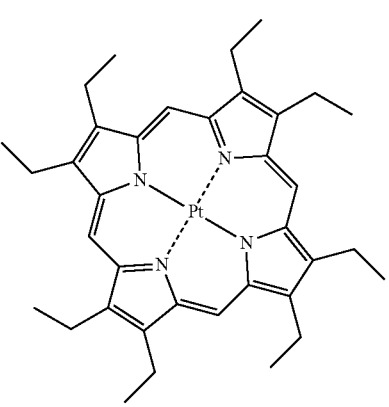
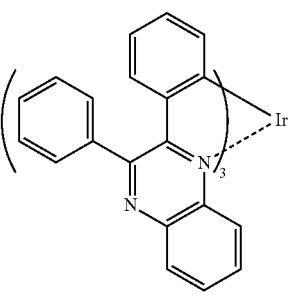
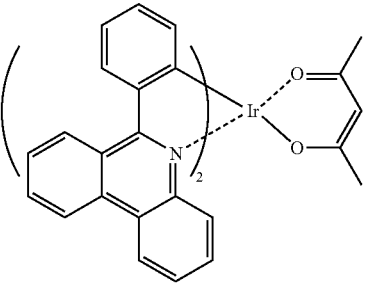

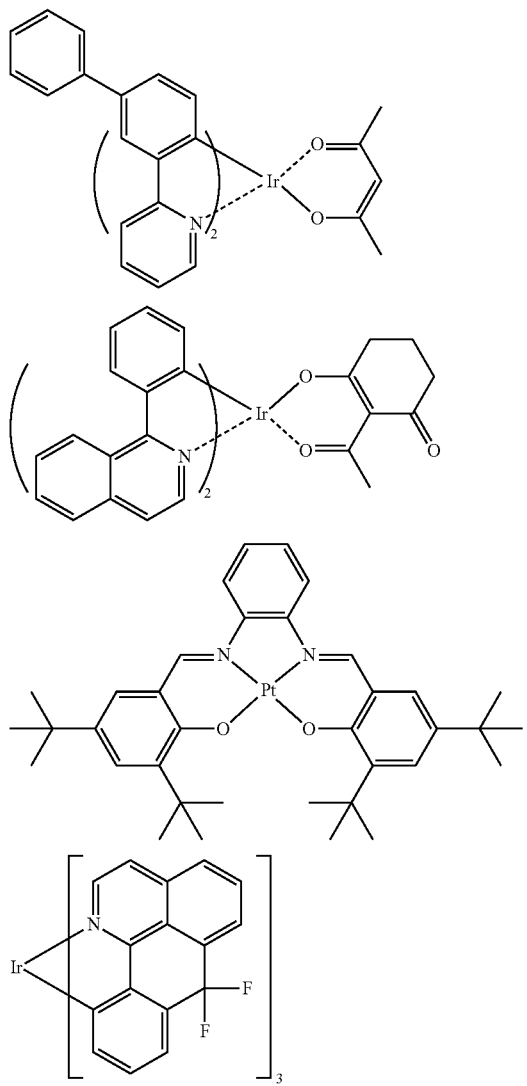
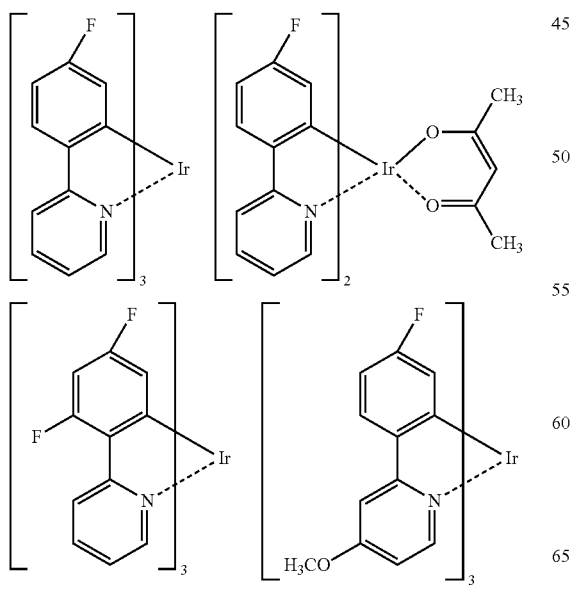
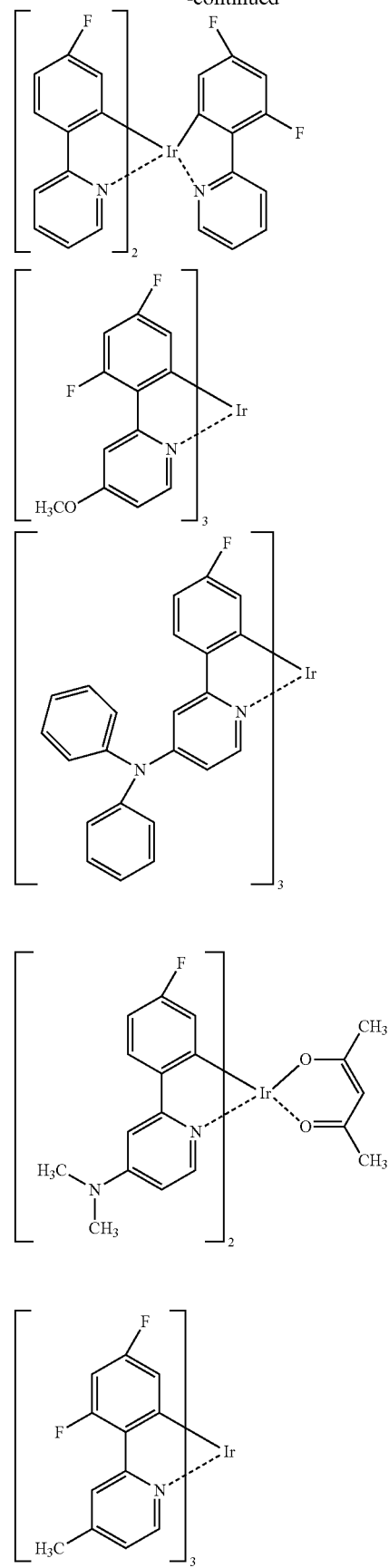

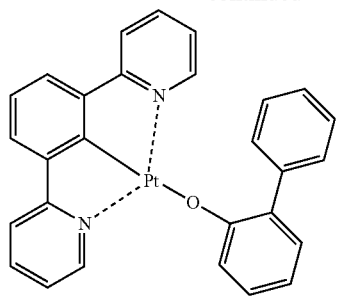
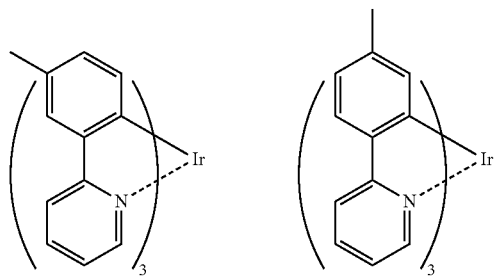
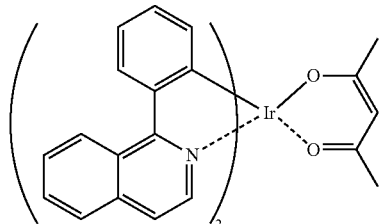
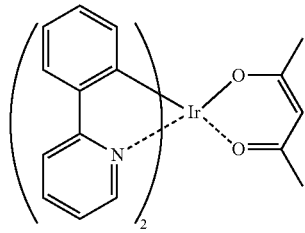
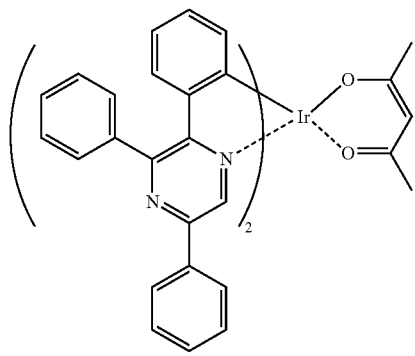
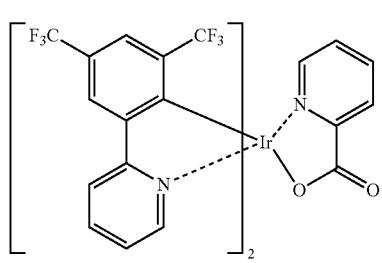
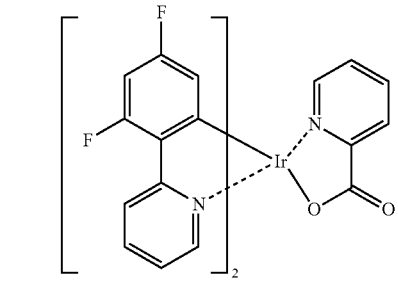
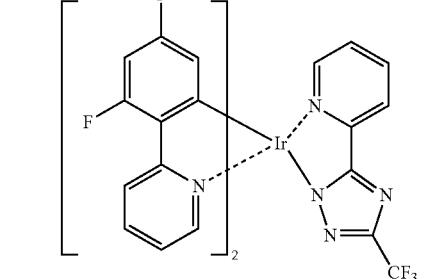
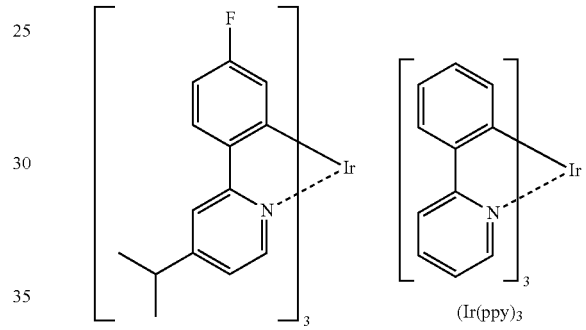
(Ir(ppy)₃)
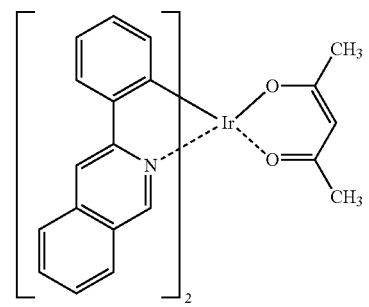
[Chem. 21]
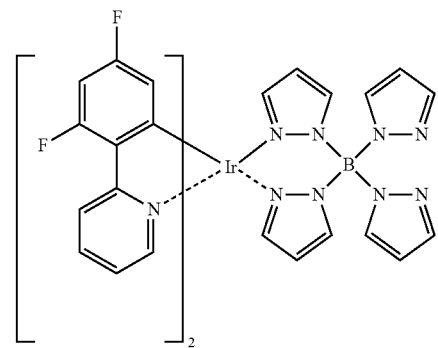

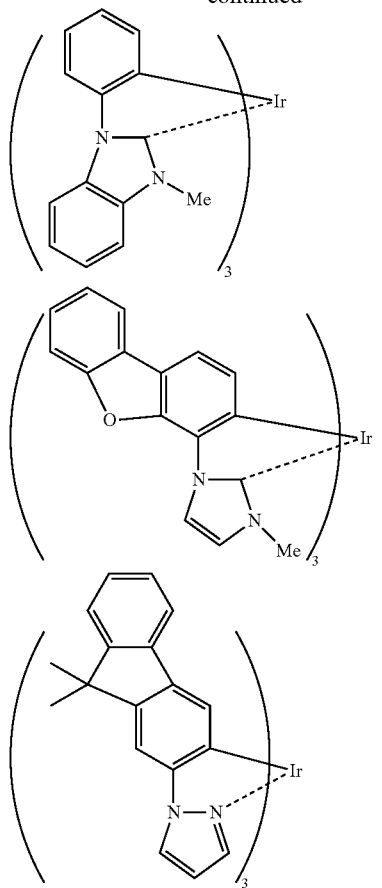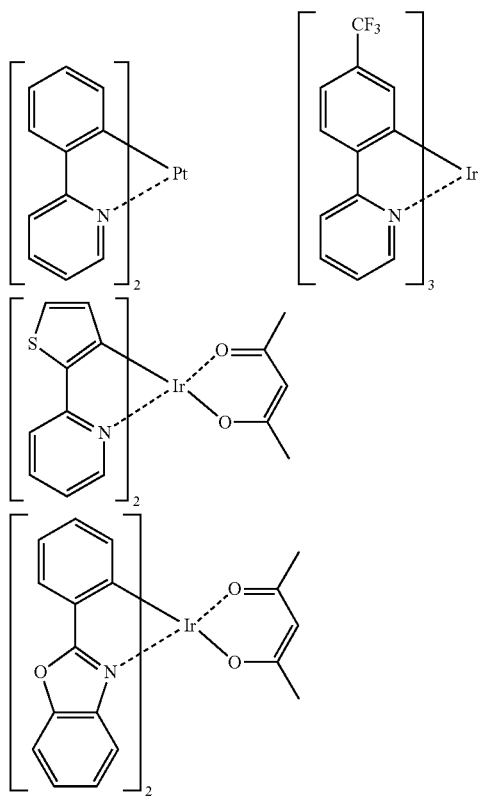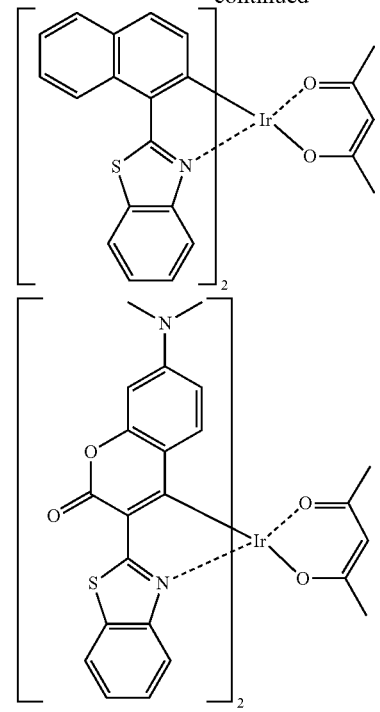

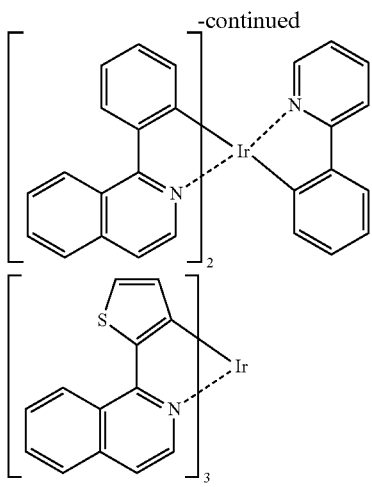

In addition, the organic EL device of the present invention is preferably such that the light emitting layer contains a host material containing the material for an organic EL device of the present invention and a phosphorescent light emitting material, and contains, as the phosphorescent light emitting material, such a blue metal complex that a local maximum value for its emission wavelength is 500 nm or less.

That is, the material for an organic EL device of the present invention is preferably used in a device containing a phosphorescent light emitting material having an emission maximum wavelength of 420 nm or more and 500 nm or less for obtaining light emission in a blue to green region in a visible light region, and the emission maximum wavelength is more preferably 430 nm or more and 480 nm or less.

In another embodiment, the organic EL device of the present invention is also suitably such that the light emitting layer contains a host material containing the material for an organic EL device of the present invention and a phosphorescent light emitting material, and contains, as the phosphorescent light emitting material, such a green metal complex that a local maximum value for its emission wavelength is 505 nm or more and 560 nm or less.

In still another embodiment, the organic EL device of the present invention is also suitably such that the light emitting layer contains a host material containing the material for an organic EL device of the present invention and a phosphorescent light emitting material, and contains, as the phosphorescent light emitting material, such a red metal complex that a local maximum value for its emission wavelength is 580 nm or more and 680 nm or less.

As described above, the organic EL device of the present invention may have a hole transporting zone between the anode and the light emitting layer, and the light emitting layer or the hole transporting zone may contain the material for an organic electroluminescence device of the present invention. Alternatively, the device may have an electron transporting zone between the light emitting layer and the cathode, and the electron transporting zone may contain the material for an organic electroluminescence device of the present invention.

The organic EL device of the present invention preferably contains the material for an organic electroluminescence device represented by the general formula (1) in one or more of the light emitting layer, the hole transporting zone (the hole transporting layer or the hole injecting layer), and the electron transporting zone (the electron transporting layer or the electron injecting layer), and in particular, more preferably contains the material in at least the light emitting layer or the hole transporting zone.

The hole transporting zone preferably has a barrier layer at a portion adjacent to the light emitting layer. As described later, the barrier layer has the following function. The layer prevents a triplet exciton produced in the light emitting layer from diffusing into the hole transporting zone to confine the triplet exciton in the light emitting layer, thereby suppressing the energy deactivation of the triplet exciton on a molecule in the hole transporting zone except the light emitting dopant.

The following description is given for an easier understanding of the present invention. The use of the compound of the present invention in the barrier layer of the hole transporting zone is assumed to be capable of preventing the energy deactivation of the triplet exciton in the hole transporting zone while enabling efficient injection of a hole into the light emitting layer. That is, the use of the compound of the present invention in the barrier layer is assumed to facilitate the control of: a region where an electron and a hole recombine with each other; and a triplet exciton distribution. In addition, the compound of the present invention is also equipped with high electrochemical stability against electron injection and electron transportation. Accordingly, the use of the compound of the present invention in the barrier layer is assumed to be capable of preventing the electrochemical deterioration of the hole transporting layer having low electrochemical stability against electron injection and electron transportation, and hence an organic electroluminescence device excellent in durability can probably be obtained.

In the case where the compound of the present invention is used in the barrier layer, when the triplet energy of the phosphorescent light emitting dopant in the light emitting layer is represented by $E^T_d$ and the triplet energy of the compound to be used in the barrier layer is represented by $E^T_{TB}$, as long as the energy magnitude correlation of $E^T_d < E^T_{TB}$ is established, a triplet exciton of the phosphorescent light emitting dopant is confined (can no longer move toward any other molecule) in terms of the energy relationship, and hence an energy deactivation path except light emission on the dopant is cut off. Accordingly, it is assumed that the device can emit light with high efficiency.

It should be noted that even in the case where the relationship of $E^T_d < E^T_{TB}$ is established, when the energy difference $\Delta E^T = E^T_{TB} - E^T_d$ is small, under an environment having a temperature of about room temperature as an actual environment where the device is driven, the triplet exciton may be able to endothermically surmount the energy difference $\Delta E^T$ by virtue of its surrounding thermal energy to move toward the other molecule. Particularly in the case of phosphorescent light emission, the lifetime of an exciton is longer than that in the case of fluorescent light emission. Accordingly, an influence of the endothermic exciton movement process appears with relative ease, and hence the use of the compound of the present invention in the barrier layer is assumed to be effective for an improvement in efficiency of a phosphorescent device. The energy difference $\Delta E^T$ is preferably as large as possible with respect to the thermal energy at room temperature, and is more preferably 0.1 eV or more, particularly preferably 0.2 eV or more.

The organic EL device of the present invention preferably has a reductive dopant in an interfacial region between the cathode and an organic thin film layer. Examples of the reductive dopant include at least one kind selected from alkali metals, alkali metal complexes, alkali metal compounds, alkaline earth metals, alkaline earth metal complexes, alkaline earth metal compounds, rare earth metals, rare earth metal complexes, and rare earth metal compounds.

Examples of the alkali metal include an alkali metal such as $L^1$ having a work function of 2.9 eV, Na having a work function of 2.36 eV, K having a work function of 2.28 eV, Rb having a work function of 2.16 eV, or Cs having a work function of 1.95 eV. An alkali metal having a work function of 2.9 eV or less is particularly preferred. Of those, K, Rb, and Cs are preferred, Rb or Cs is more preferred, and Cs is most preferred.

Examples of the alkali earth metal include an alkali earth metal such as Ca having a work function of 2.9 eV, Sr having a work function of 2.0 to 2.5 eV, or Ba having a work function of 2.52 eV. An alkali earth metal having a work function of 2.9 eV or less is particularly preferred.

Examples of the rare earth metal include Sc, Y, Ce, Tb, and Yb. A rare earth metal having a work function of 2.9 eV or less is particularly preferred.

Of those metals, a preferred metal has a particularly high reductive ability, so improvement of light emission luminance and long life of organic EL device can be attained by adding a relatively small amount of the metal to an electron injecting region.

Examples of the alkali metal compound include an alkali oxide such as $Li_2O$, $Cs_2O$, or $K_2O$, and an alkali halide such as LiF, NaF, CsF, or KF. Of those, LiF, $Li_2O$, and NaF are preferred.

Examples of the alkali earth metal compound include BaO, SrO, CaO, and mixtures thereof such as $Ba_xSr_{1-x}O$ (0<x<1) and $Ba_xCa_{1-x}O$ (0<x<1). Of those, BaO, SrO, and CaO are preferred.

Examples of the rare earth metal compound include $YbF_3$, $ScF_3$, $ScO_3$, $Y_2O_3$, $Ce_2O_3$, $GdF_3$, and $TbF_3$. Of those, $YbF_3$, $ScF_3$, and $TbF_3$ are preferred.

The alkali metal complex, alkali earth metal complex, and rare earth metal complex are not particularly limited as long as they each contain, as a metal ion, at least one of alkali metal ions, alkali earth metal ions, and rare earth metal ions. Further, preferred examples of a ligand include, but not limited to, quinolinol.

For the addition form of the reductive dopant, it is preferred that the reductive dopant be formed in a shape of a layer or an island in the interfacial region. A preferred example of the forming method is a method in which an organic substance which is a light emitting material or an electron injecting material for forming the interfacial region is deposited at the same time as the reductive dopant is deposited by a resistant heating deposition method, thereby dispersing the reductive dopant in the organic substance. The disperse concentration by molar ratio of the organic substance to the reductive dopant is 100:1 to 1:100, and is preferably 5:1 to 1:5. In a case where the reductive dopant is formed into the shape of a layer, the light emitting material or electron injecting material which serves as an organic layer in the interface is formed into the shape of a layer. After that, the reductive dopant is solely deposited by the resistant heating deposition method to form a layer preferably having a thickness of 0.1 to 15 nm. In a case where the reductive dopant is formed into the shape of an island, the light emitting material or electron injecting material which serves as an organic layer in the interface is formed into the shape of an island. After that, the reductive dopant is solely deposited by the resistant heating deposition method to form an island preferably having a thickness of 0.05 to 1 nm.

It is preferred that the organic EL device of the present invention has an electron injecting layer between the light emitting layer and the cathode, and the electron injecting layer contains a nitrogen-containing heterocyclic derivative as a main component. An electron transporting material to be used in the electron injecting layer is preferably an aromatic heterocyclic compound containing one or more hetero atoms in its molecules, or particularly preferably a nitrogen-containing heterocyclic derivative.

The nitrogen-containing heterocyclic derivative is preferably, for example, a nitrogen-containing heterocyclic metal chelate complex represented by the formula (A).

The nitrogen-containing heterocyclic derivative is preferably, for example, a nitrogen-containing heterocyclic metal chelate complex represented by the formula (A).

[Chem. 23]

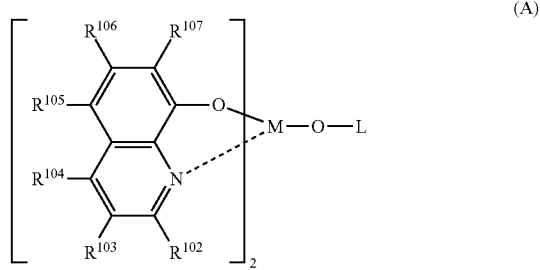

(A)

$R^{102}$ to $R^{107}$ each independently represent a hydrogen atom, a halogen atom, an amino group, a hydrocarbon group having 1 to 40 carbon atoms, an alkoxy group, an aryloxy group, an alkoxycarbonyl group, or a heterocyclic group, each of which may be substituted.

Examples of the halogen atom include a fluorine atom, a chlorine atom, a bromine atom, and an iodine atom. Further, examples of the amino group which may be substituted include the same examples as those described for the alkylamino group and arylamino group. In addition, the amino group which may be substituted may be an aralkylamino group.

Examples of the hydrocarbon group having 1 to 40 carbon atoms include a substituted or unsubstituted alkyl group, alkenyl group, cycloalkyl group, aryl group, and aralkyl group. Examples of the alkyl group, the cycloalkyl group, the alkoxy group, the aryl group, the heterocyclic group, and the aryloxy group include the same examples as those described above. Examples of the alkenyl group include groups corresponding to the above-mentioned alkyl groups. Examples of the aralkyl group include the above-mentioned alkyl group substituted with the above-mentioned aryl group. Alkoxycarbonyl group is represented as —COOY', and examples of Y' include the same examples as those described for the alkyl group.

M represents aluminum (Al), gallium (Ga), or indium (In), and preferably In.

L in the formula (A) is a group represented by the following formula (A') or (A").

[Chem. 24]

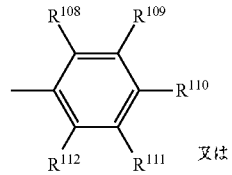

-continued

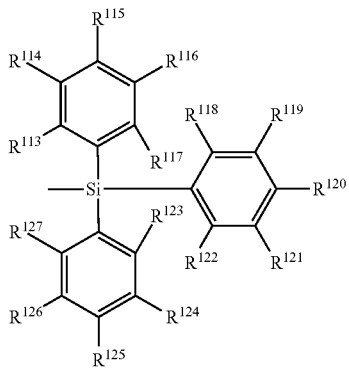
(A'')

In the formula, $R^{108}$ to $R^{112}$ each independently represent a hydrogen atom or a substituted or unsubstituted hydrocarbon group having 1 to 40 carbon atoms, and groups adjacent to each other may form a cyclic structure. In addition, $R^{113}$ to $R^{127}$ each independently represent a hydrogen atom or a substituted or unsubstituted hydrocarbon group having 1 to 40 carbon atoms, and groups adjacent to each other may form a cyclic structure.

Examples of the hydrocarbon group having 1 to 40 carbon atoms represented by any one of $R^{108}$ to $R^{112}$ and $R^{113}$ to $R^{127}$ in the formula (A') and the formula (A'') include the same examples as the specific examples of $R^2$ to $R^7$.

In addition, a divalent group in the case where groups adjacent to each other out of $R^8$ to $R^{12}$ and $R^{13}$ to $R^{27}$ form a cyclic structure is, for example, a tetramethylene group, a pentamethylene group, a hexamethylene group, a diphenylmethane-2,2'-diyl group, a diphenylethane-3,3'-diyl group, or a diphenylpropane-4,4'-diyl group.

Specific examples of the nitrogen-containing heterocyclic metal chelate complex represented by the formula (A) are shown below, but the present invention is not limited to these exemplified compounds.

[Chem. 25]

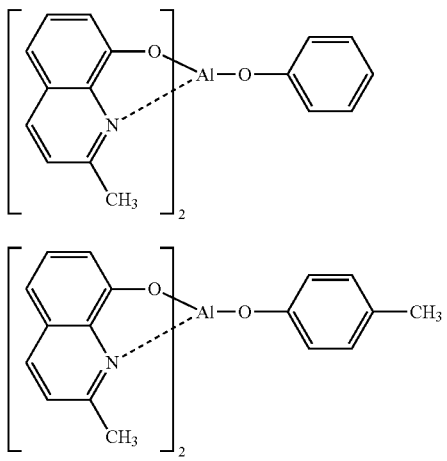

The nitrogen-containing heterocyclic derivative is a nitrogen-containing heterocyclic derivative formed of an organic compound having any one of the following general formulae, and a nitrogen-containing compound which is not a metal complex is also an example of the derivative. The derivative is, for example, a derivative which have a five- or six-membered ring containing a skeleton represented by the following formula (a) or a derivative whose structure is represented by the following formula (b).

[Chem. 26]

(a)

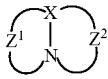
(b)

In the formula (b), X represents a carbon atom or a nitrogen atom, and $Z^1$ and $Z^2$ each independently represent an atomic group capable of forming a nitrogen-containing heterocycle.

An organic compound having a nitrogen-containing aromatic polycycle formed of a five- or six-membered ring is preferred. In the case of such nitrogen-containing aromatic polycycle having a plurality of nitrogen atoms, a nitrogen-containing aromatic polycyclic organic compound having a skeleton obtained by combining the above-mentioned formulae (a) and (b) is more preferred.

The nitrogen-containing group of the nitrogen-containing organic compound is selected from, for example, nitrogen-containing heterocyclic groups represented by the following general formulae.

[Chem. 27]

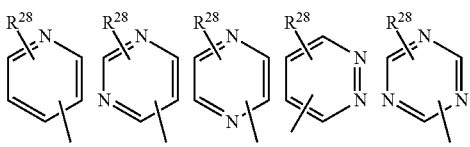

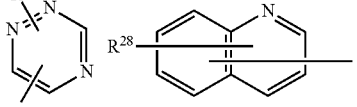

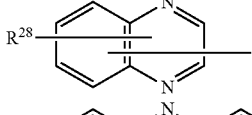

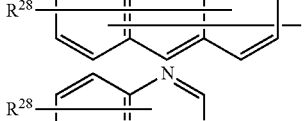

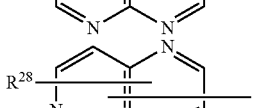

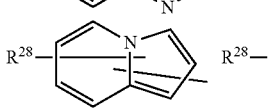

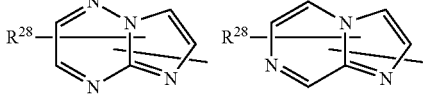

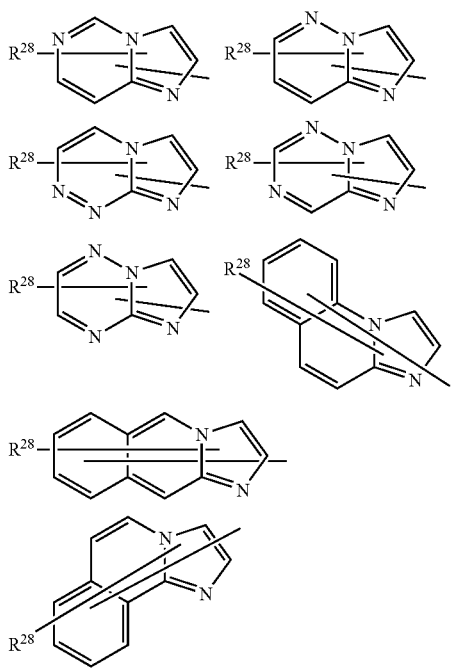

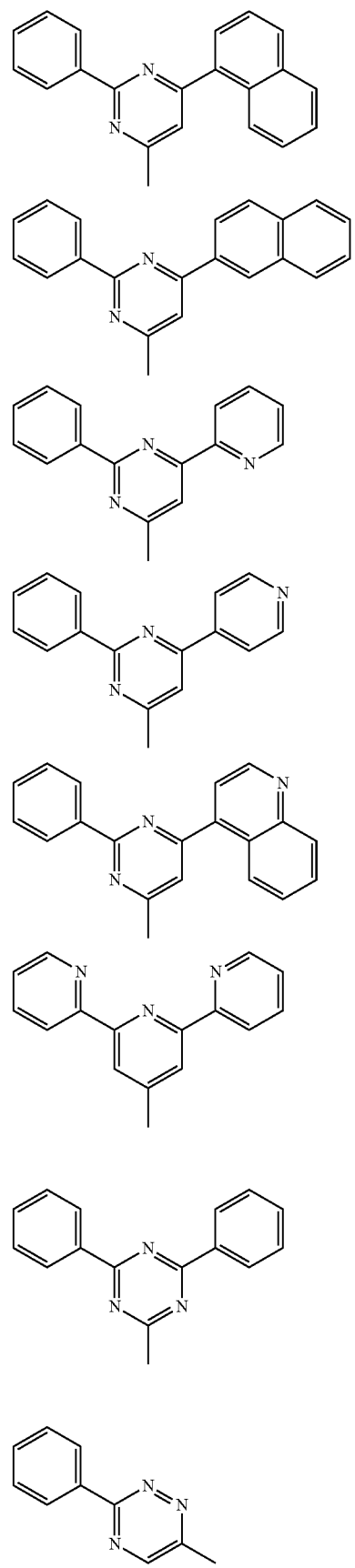

In each of the formulae, $R^{28}$ represents an aryl group having 6 to 40 carbon atoms, a heteroaryl group having 3 to 40 carbon atoms, an alkyl group having 1 to 20 carbon atoms, or an alkoxy group having 1 to 20 carbon atoms, n represents an integer of 0 to 5, and when the n represents an integer of two or more, a plurality of $R^{28}$s may be identical to or different from each other.

Further, a preferred specific compound is, for example, a nitrogen-containing heterocyclic derivative represented by the following formula.

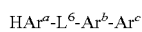

[Chem. 28]

In the formula, $HAr^a$ represents a nitrogen-containing heterocycle which has 3 to 40 carbon atoms and which may have a substituent, $L^b$ represents a single bond, an arylene group which has 6 to 40 carbon atoms and which may have a substituent, or a heteroarylene group which has 3 to 40 carbon atoms and which may have a substituent, $Ar^b$ represents a divalent aromatic hydrocarbon group which has 6 to 40 carbon atoms and which may have a substituent, and $Ar^c$ represents an aryl group which has 6 to 40 carbon atoms and which may have a substituent, or a heteroaryl group which has 3 to 40 carbon atoms and which may have a substituent.)

$HAr^a$ is, for example, selected from the following group.

[Chem. 29]

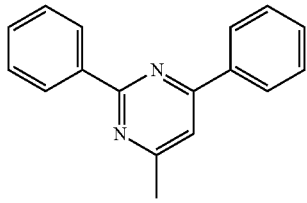

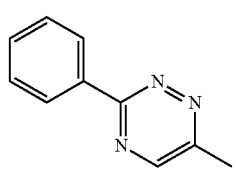

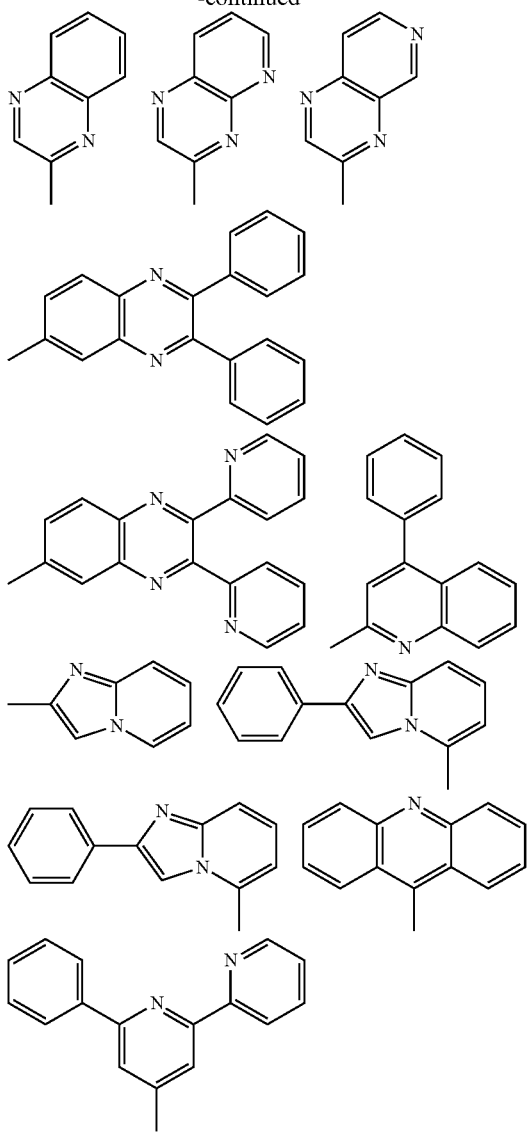

L⁶ is, for example, selected from the following group.

[Chem. 30]

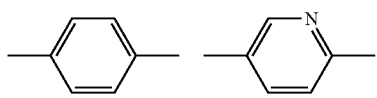

Arᶜ is, for example, selected from the following group.

[Chem. 31]

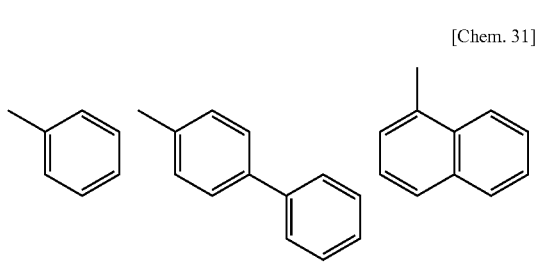

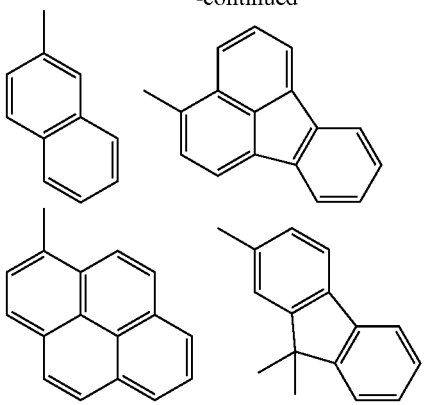

Arᵇ is, for example, selected from the following arylanthranil groups.

[Chem. 32]

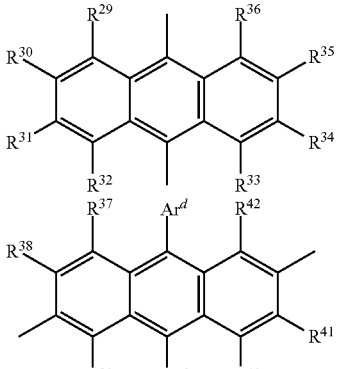

In the formulae, $R^{29}$ to $R^{42}$ each independently represent a hydrogen atom, a halogen atom, an alkyl group having 1 to 20 carbon atoms, an alkoxy group having 1 to 20 carbon atoms, an aryloxy group having 6 to 40 carbon atoms, an aryl group which has 6 to 40 carbon atoms and which may have a substituent, or a heteroaryl group having 3 to 40 carbon atoms, and $Ar^d$ represents an aryl group which has 6 to 40 carbon atoms and which may have a substituent, or a heteroaryl group having 3 to 40 carbon atoms.

In addition, a nitrogen-containing heterocyclic derivative in which $R^{29}$ to $R^{36}$ in $Ar^b$ represented by the above-mentioned formula each represent a hydrogen atom is preferred.

In addition to the foregoing, the following compound (see JP 09-3448 A) is also suitably used.

[Chem. 33]

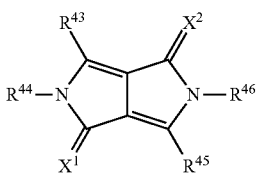

In the formula, $R^{43}$ to $R^{46}$ each independently represent a hydrogen atom, a substituted or unsubstituted aliphatic group, a substituted or unsubstituted alicyclic group, a substituted or unsubstituted carbocyclic aromatic ring group, or a substituted or unsubstituted heterocyclic group, and $X^1$ and $X^2$ each independently represent an oxygen atom, a sulfur atom, or a dicyanomethylene group.

In addition, the following compound (see JP 2000-173774 A) is also suitably used.

[Chem. 34]

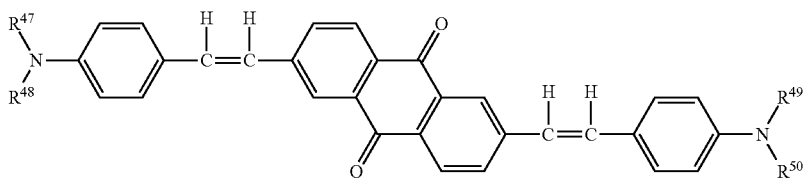

In the formula, $R^{47}$, $R^{48}$, $R^{49}$, and $R^{50}$ represent groups identical to or different from one another, and each represent an aryl group represented by the following formula.

[Chem. 35]

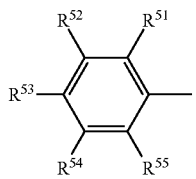

In the formula, $R^{51}$, $R^{52}$, $R^{53}$, $R^{54}$, and $R^{55}$ represent groups identical to or different from one another, and each represent a hydrogen atom, or at least one of them may represent a saturated or unsaturated alkoxyl, alkyl, amino, or alkylamino group.

Further, a polymer compound containing the nitrogen-containing heterocyclic group or nitrogen-containing heterocyclic derivative is also permitted.

In addition, the electron transporting layer preferably contains at least one of the nitrogen-containing heterocyclic derivatives represented by the following formulae (201) to (203).

[Chem. 36]

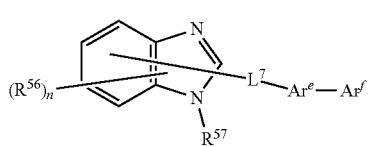 (201)

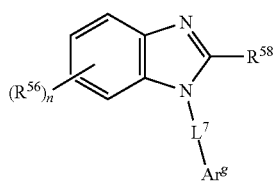 (202)

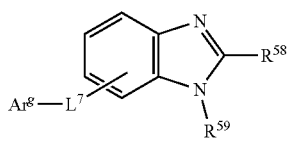 (203)

In the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, n represents an integer of 0 to 4, $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms, $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, $L^7$ represents a single bond, an arylene group which has 6 to 60 carbon atoms and which may have a substituent, a pyridinylene group which may have a substituent, a quinolinylene group which may have a substituent, or a fluorenylene group which may have a substituent, $Ar^e$ represents an arylene group which has 6 to 60 carbon atoms and which may have a substituent, a pyridinylene group which may have a substituent, or a quinolinylene group which may have a substituent, and $Ar^f$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

$Ar^g$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, an alkoxy group which has 1 to 20 carbon atoms and which may have a substituent, or a group represented by —$Ar^e$-$Ar^f$ ($Ar^e$ and $Ar^f$ each have the same meaning as that described above).

It should be noted that, in the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

As the aryl group having 6 to 60 carbon atoms, an aryl group having 6 to 40 carbon atoms is preferred, an aryl group having 6 to 20 carbon atoms is more preferred, specifically, a phenyl group, a naphthyl group, an anthryl group, a phenanthryl group, a naphthacenyl group, a chrysenyl group, a pyrenyl group, and a biphenyl group are preferred.

As the alkyl group having 1 to 20 carbon atoms, an alkyl group having 1 to 6 carbon atoms is preferred, specifically, for example, a methyl group and an ethyl group are given. The alkyl group having three or more carbon atoms may be linear, cyclic, or branched.

As the alkoxy group having 1 to 20 carbon atoms, an alkoxy group having 1 to 6 carbon atoms are preferred, specifically, for example, a methoxy group and an ethoxy group are given. As the alkoxy group having three or more carbon atoms may be linear, cyclic, or branched.

A substituent for each group represented by $R^{56}$ include a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, and a heteroaryl group which has 3 to 40 carbon atoms and which may have a substituent.

Examples of the halogen atom include a fluorine, a chlorine, a bromine, and a iodine.

Examples of the alkyl group having 1 to 20 carbon atoms, the alkoxy group having 1 to 20 carbon atoms, and the aryl group having 6 to 40 carbon atoms include the same groups as described above.

Examples of the aryloxy group having 6 to 40 carbon atoms include a phenoxy group and a biphenyloxy group.

Examples of the heteroaryl group having 3 to 40 carbon atoms include a pyrrolyl group, a furyl group, a thienyl group, a silolyl group, a pyridyl group, a quinolyl group, an isoquinolyl group, a benzofuryl group, an imidazofuryl group, a pyrimidyl group, and a carbazolyl group.

n represents an integer of 0 to 4, preferably 0 to 2.

In the formula (201), $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms.

Specific examples of each of those groups, preferred number of carbon atoms and substituents are the same as described for the R.

In the formula (202) and (203), $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of each of those groups, preferred number of carbon atoms and substituents are the same as described for the $R^{56}$.

In the formulae (201) to (203), $L^7$ represents a single bond, an arylene group which has 6 to 60 carbon atoms and which may have a substituent, a pyridinylene group which may have a substituent, a quinolinylene group which may have a substituent, or a fluorenylene group which may have a substituent.

As the arylene group having 6 to 60 carbon atoms, an arylene group having 6 to 40 carbon atoms is preferred, an arylene group having 6 to 20 carbon atoms is more preferred, and specifically, for example, a divalent group produced by removing a hydrogen atom from the aryl group described for the R is given. The substituent for each of those groups represented by $L^7$ are the same as described for the $R^{56}$.

In addition, $L^7$ is preferably a group selected from the group consisting of the following groups.

[Chem. 37]

In the formula (201), $Ar^e$ represents an arylene group which has 6 to 60 carbon atoms and which may have a substituent, a pyridinylene group which may have a substituent, or a quinolinylene group which may have a substituent. Examples of the substituent for each group represented by $Ar^e$ and $Ar^g$ are the same as described for the R.

In addition, $Ar^e$ preferably represents a group selected from fused ring groups represented by the formulae (101) to (110) below.

[Chem. 38]

(101)

(102)

(103)

(104)

-continued

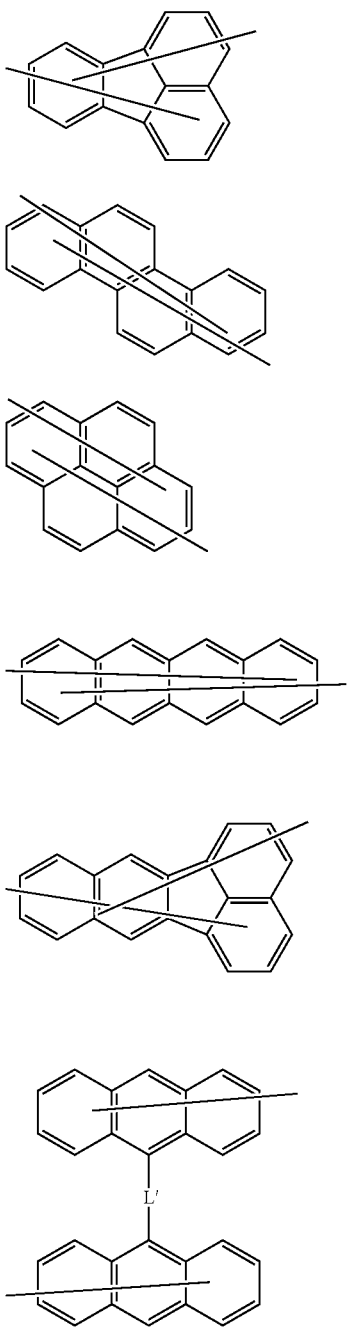

(105)

(106)

(107)

(108)

(109)

(110)

In the formulae (101) to (110), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, or an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from each other. Specific examples of each of those groups are the same as described above.

In the formula (110), L' represents a single bond, or a group selected from the group consisting of the following groups.

[Chem. 39]

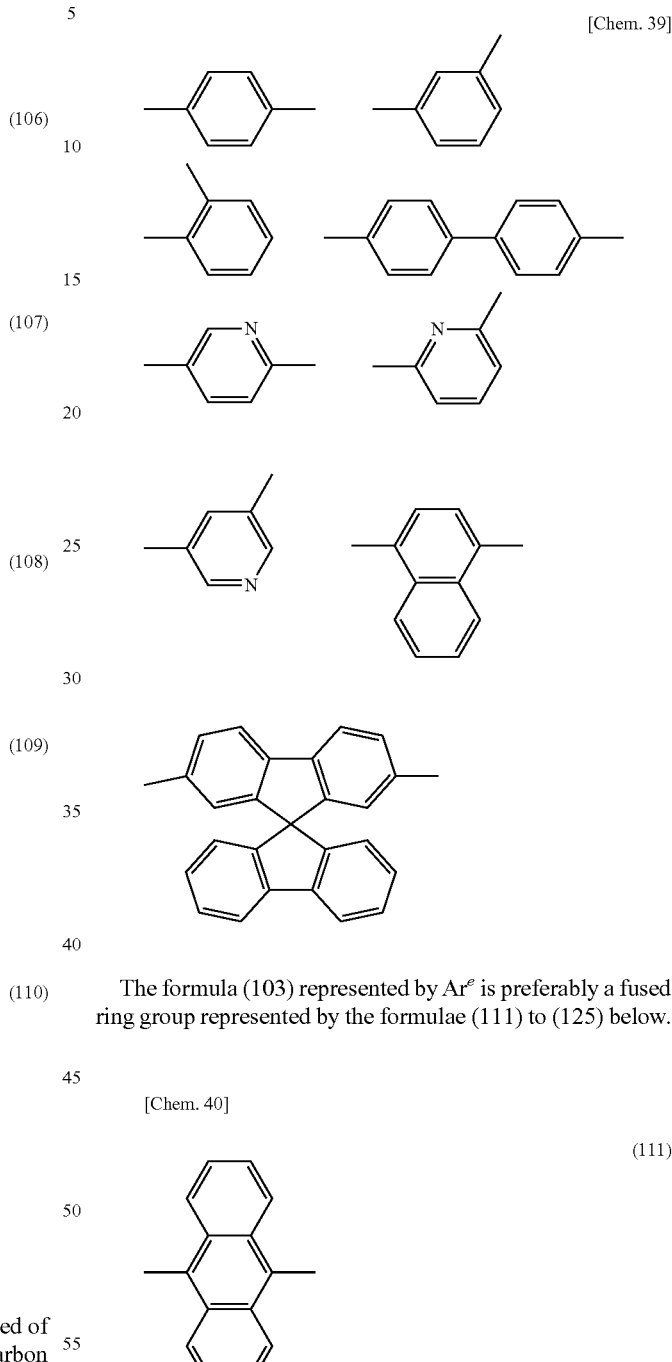

The formula (103) represented by $Ar^e$ is preferably a fused ring group represented by the formulae (111) to (125) below.

[Chem. 40]

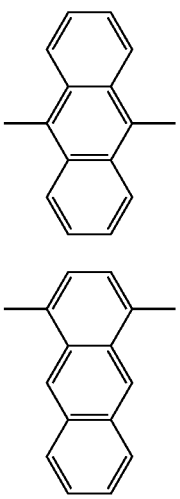

(111)

(112)

-continued
(113)
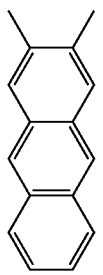
(114)
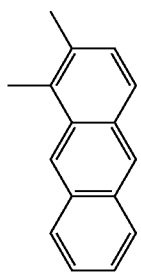
(115)
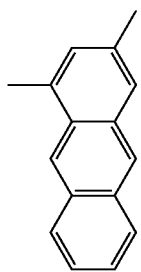
(116)
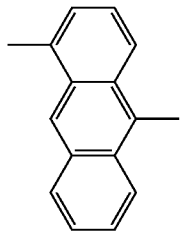
(117)
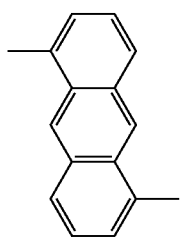
(118)
-continued
(119)
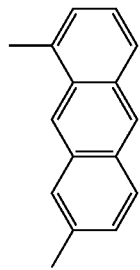
(120)
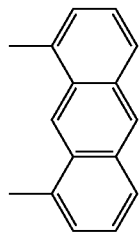
(121)
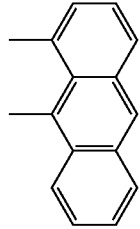
(122)
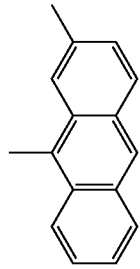
(123)
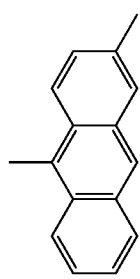
(124)
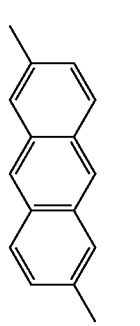

-continued (125)

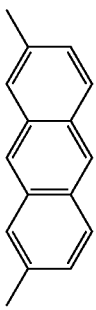

In the formulae (111) to (125), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from each other. Specific examples of each of those groups are the same as described above.

In the formula (201), Ar$^f$ represents, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of each of those groups, preferred number of carbon atoms and substituents are the same as described for the R$^{56}$.

In the formulae (202) and (203), Ar$^g$ represents, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, an alkoxy group which has 1 to 20 carbon atoms and which may have a substituent, or a group represented by —Ar$^e$-Ar$^f$ (each of Ar$^e$ and Ar$^f$ is the same as described above.)

Specific examples of each of those groups, preferred number of carbon atoms and substituents are the same as described for the R$^{56}$.

In addition, Ar$^g$ is preferably a group selected from fused ring groups represented by formulae (126) to (135) below.

[Chem. 41]

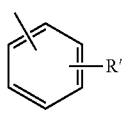

(126)

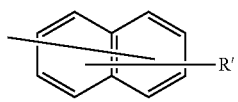

(127)

(128)

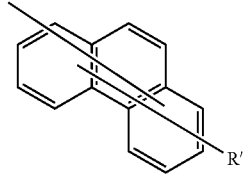

(129)

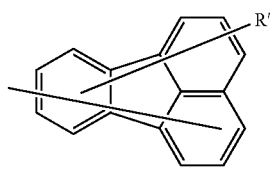

(130)

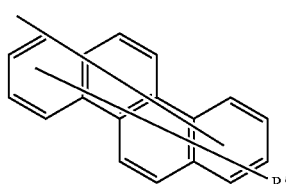

(131)

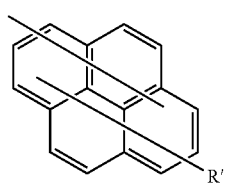

(132)

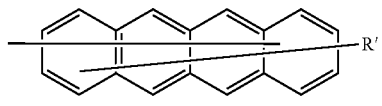

(133)

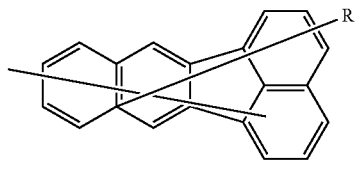

(134)

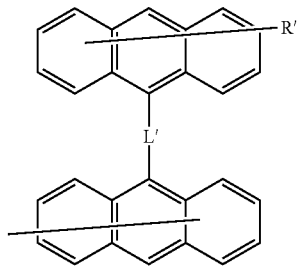

(135)

In the formulae (126) to (135), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from each other. Specific examples of each of those groups are the same as described above.

In the formula (135), L' is the same as described above.

In the formulae (126) to (135), R' represents a hydrogen atom, an alkyl group which has 1 to 20 carbon atoms and which may have a substituent, an aryl group which has 6 to 40 carbon atoms and which may have a substituent, or a heteroaryl group which has 3 to 40 carbon atoms and which may have a substituent. Specific examples of each of those groups are the same as described above.

The general formula (128) represented by $Ar^g$ is preferably a fused ring group represented by formulae (136) to (158) below.

[Chem. 42]

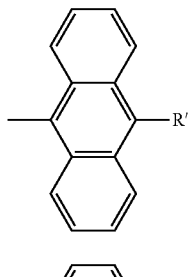
(136)

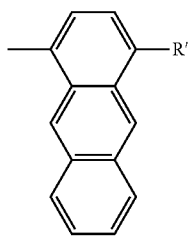
(137)

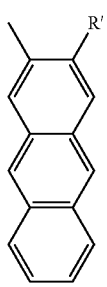
(138)

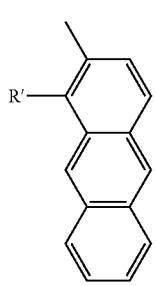
(139)

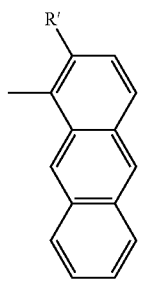
(140)

(141)

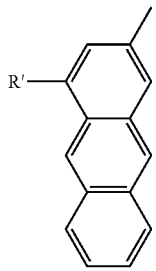
(142)

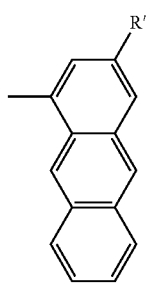
(143)

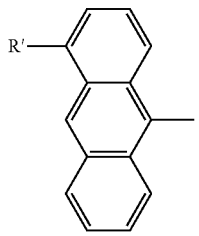
(144)

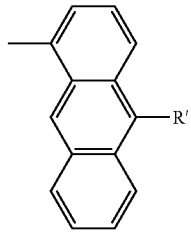
(145)

(146) 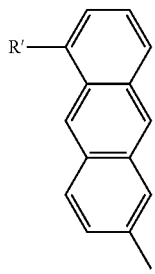
(147) 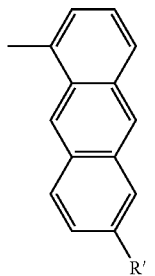
(148) 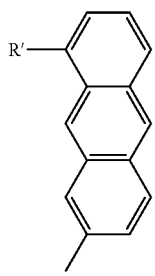
(149) 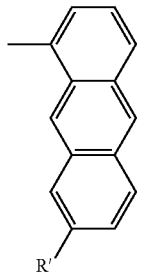
(150) 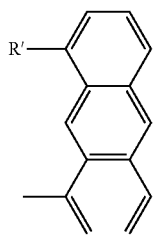
(151) 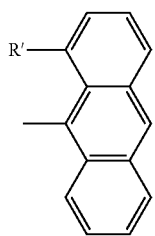
(152) 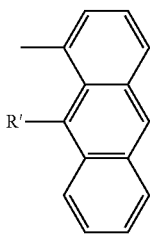
(153) 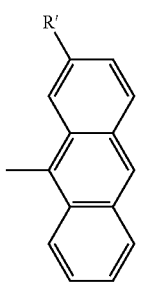
(154) 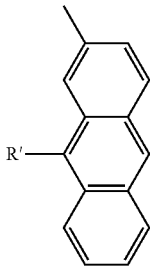
(155) 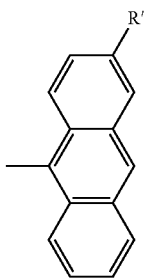
(156) 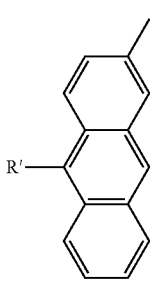

(157)

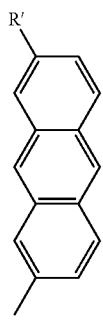

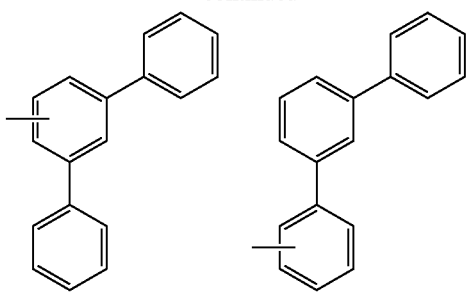

(158)

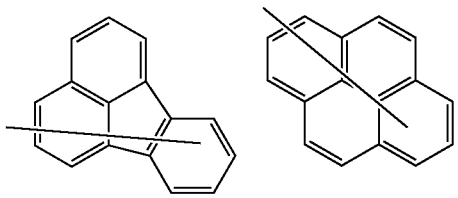

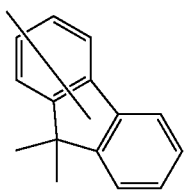

In the formulae (136) to (158), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from one another. Specific examples of each of those groups are the same as described above. R' is the same as described above.

Further, Ar$^f$ and Ar$^g$ each independently represent a group selected from the group consisting of the following groups.

[Chem. 43]

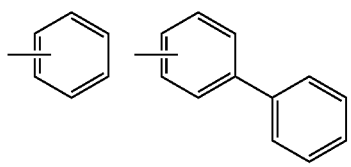

Specific examples of the nitrogen-containing heterocyclic derivatives represented by the formulae (201) to (203) of the present invention are shown below, but the present invention is not limited to these exemplified compounds.

It should be noted that HAr in the following table represents any one of the following parts in the formulae (201) to (203).

[Chem. 44]

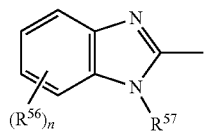

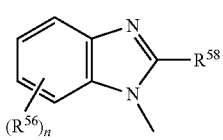

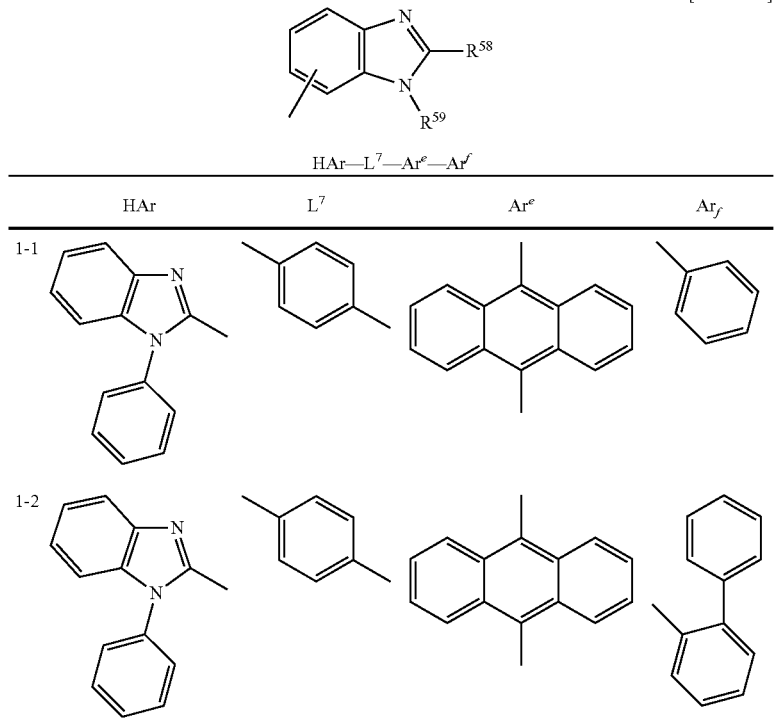

Of those specific examples, (1-1) is particularly preferable.

In addition, as the nitrogen-containing heterocyclic derivative, a nitrogen-containing five-membered ring derivative is preferably exemplified. Examples of the nitrogen-containing five-membered ring include an imidazole ring, a triazole ring, a tetrazole ring, an oxadiazole ring, a thiadiazole ring, an oxatriazole ring, and a thiatriazole ring. Examples of the nitrogen-containing five-membered ring derivative include a benzoimidazole ring, a benzotriazole ring, a pyridinoimidazole ring, a pyrimidinoimidazole ring, and a pyridazinoimidazole ring. Particularly preferred is the compound represented by the following general formula (B).

[Chem. 46]

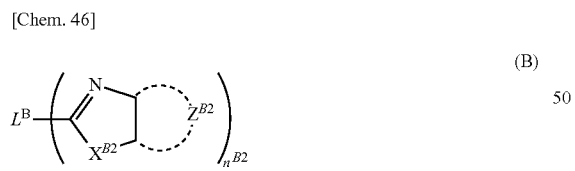

(B)

In the general formula (B), $L^B$ represents a divalent or more linking group. Examples thereof include a carbon atom, a silicon atom, a nitrogen atom, a boron atom, an oxygen atom, a sulfur atom, metal atoms (for example, a barium atom and a beryllium atom), an aromatic hydrocarbon ring, and an aromatic heterocycle. Of those, a carbon atom, a nitrogen atom, a silicon atom, a boron atom, an oxygen atom, a sulfur atom, an aromatic hydrocarbon ring, and an aromatic heterocycle are preferred, and a carbon atom, a silicon atom, an aromatic hydrocarbon ring, and an aromatic heterocycle are still more preferred.

An aromatic hydrocarbon ring group and an aromatic heterocyclic group represented by $L^B$ may have a substituent. Examples of such substituent preferably include an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, and an aromatic heterocyclic group.

Specific Examples of $L^B$ are as shown below.

[Chem. 47]

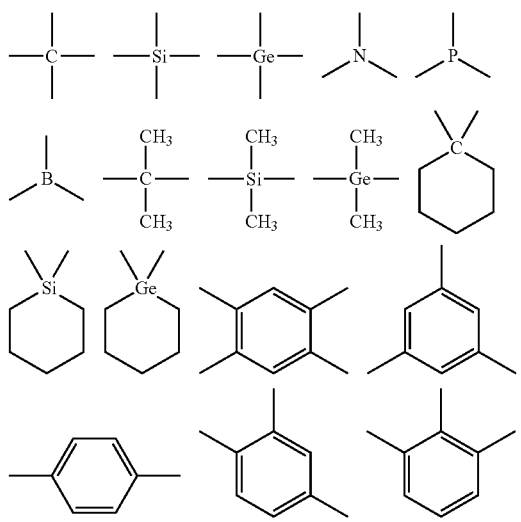

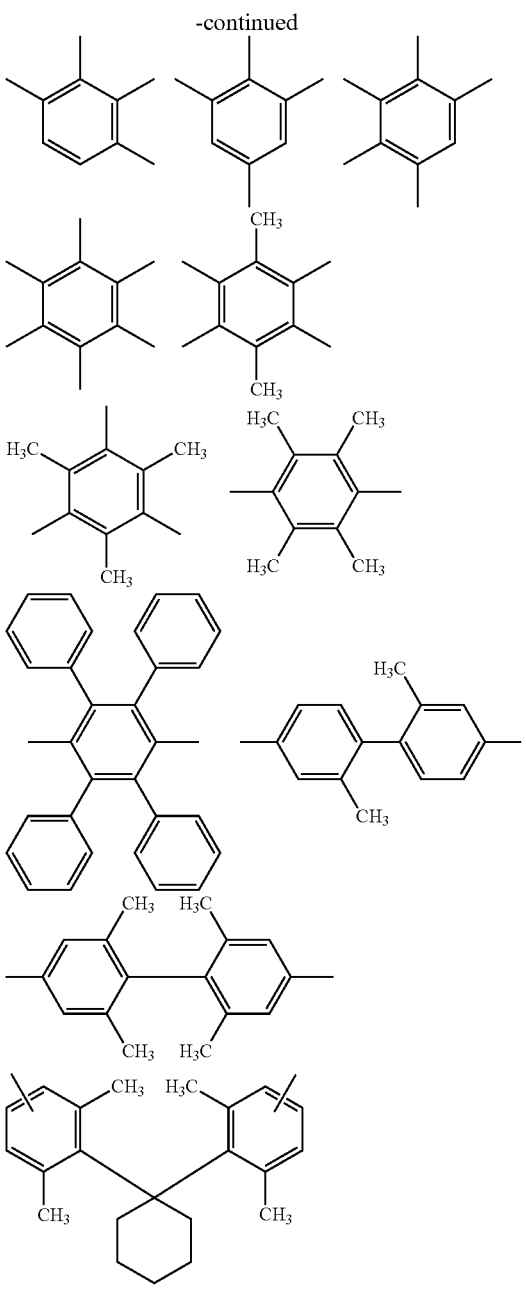

$X^{B2}$ in the general formula (B) represents —O—, —S—, or —N($R^{B2}$)—. $R^{B2}$ represents a hydrogen atom, an aliphatic hydrocarbon group, an aryl group, or a heterocyclic group.

The aliphatic hydrocarbon group represented by $R^{B2}$ is a linear or branched alkyl group (an alkyl group having preferably 1 to 20 carbon atoms, more preferably 1 to 12 carbon atoms, particularly preferably 1 to 8 carbon atoms such as a methyl group or an ethyl group), a cycloalkyl group (a cycloalkyl group having preferably 3 to 10 ring carbon atoms such as a cyclopropyl group, a cyclopentyl group, or a cyclohexyl group), an alkenyl group (an alkenyl group having preferably 2 to 20 carbon atoms, more preferably 2 to 12 carbon atoms, particularly preferably 2 to 8 carbon atoms such as a vinyl group, an allyl group, a 2-butenyl group, or a 3-pentenyl group), or an alkynyl group (an alkynyl group having preferably 2 to 20 carbon atoms, more preferably 2 to 12 carbon atoms, particularly preferably 2 to 8 carbon atoms such as a propargyl group or a 3-pentynyl group). Of those, an alkyl group is preferred.

The aryl group represented by $R^{B2}$ is a monocycle or a fused ring, and is an aryl group having preferably 6 to 30 ring carbon atoms, more preferably 6 to 20 ring carbon atoms, still more preferably 6 to 12 ring carbon atoms. Examples thereof include a phenyl group, a 1-naphthyl group, and a 2-naphthyl group. Of those, a phenyl group is preferred.

The heterocyclic group represented by $R^{B2}$ is a monocycle or a fused ring, and is a heterocyclic group having preferably 1 to 20 ring carbon atoms, more preferably 1 to 12 ring carbon atoms, still more preferably 2 to 10 ring carbon atoms. The heterocyclic group is an aromatic heterocyclic group containing at least one heteroatom out of a nitrogen atom, an oxygen atom, a sulfur atom, and a selenium atom. Examples of the heterocyclic group include groups derived from pyrrolidine, piperidine, carbazole, and azepine.

The aliphatic hydrocarbon group, the aryl group, and the heterocyclic group each represented by $R^{B2}$ may have a substituent, and the substituent is preferably an alkyl group, an alkenyl group, an alkynyl group, or an aryl group.

$R^{B2}$ represents preferably an aliphatic hydrocarbon group, an aryl group, or a heterocyclic group, more preferably an aliphatic hydrocarbon group (a group having preferably 6 to 30 carbon atoms, more preferably 6 to 20 carbon atoms, still more preferably 6 to 12 carbon atoms), or an aryl group, still more preferably an aliphatic hydrocarbon group (a group having preferably 1 to 20 carbon atoms, more preferably 1 to 12 carbon atoms, still more preferably 2 to 10 carbon atoms).

$X^{B2}$ represents preferably —O— or —N($R^{B2}$)—, more preferably —N($R^{B2}$)—.

$Z^{B2}$ represents an atomic group needed for forming an aromatic ring, and the aromatic ring formed of $Z^{B2}$ may be each of an aromatic hydrocarbon ring and an aromatic heterocycle. Specific examples thereof include a benzene ring, a pyridine ring, a pyrazine ring, a pyrimidine ring, a pyridazine ring, and a triazine ring.

The aromatic ring formed of $Z^{B2}$ may further form a fused ring with any other ring, or may have a substituent. Examples of the substituent include the same examples as those listed for the substituent for a group represented by the $L^B$.

Of the nitrogen-containing five-membered ring derivatives each represented by the general formula (B), a derivative represented by the following general formula (B') is more preferred.

[Chem. 48]

(B')

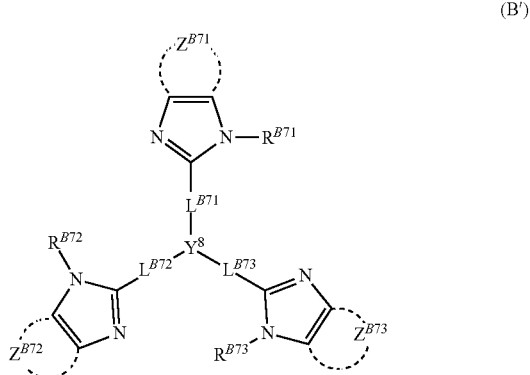

In the general formula (B'), $R^{B71}$, $R^{B72}$, and $R^{B73}$ each have the same meaning and preferred range as those of $R^{B2}$ in the general formula (B).

$Z^{B71}$, $Z^{B72}$, and $Z^{B73}$ each have the same meaning and preferred range as those of $Z^{B2}$ in the general formula (B).

$L^{B71}$, $L^{B72}$, and $Z^{B73}$ each represent a linking group, and examples of the linking group include examples obtained by making the examples of $L^B$ in the general formula (B) divalent. The linking group is preferably a single bond, a divalent aromatic hydrocarbon ring group, a divalent aromatic heterocyclic group, or a linking group formed of a combination of two or more of them, or is more preferably a single bond. $L^{B71}$, $L^{B72}$, and $Z^{B73}$ may each have a substituent. Examples of the substituent include the same examples as those described for the substituent of the group represented by $L^B$ in the general formula (B). In addition, preferred substituents are as same as those described for the substituent of the group represented by $L^B$.

$Y^B$ represents a nitrogen atom, a 1,3,5-benzenetriyl group, or a 2,4,6-triazinetriyl group. The 1,3,5-benzenetriyl group may have a substituent at its 2-, 4-, 6-position, and examples of the substituent include an alkyl group, an aromatic hydrocarbon ring group, and a halogen atom.

Specific examples of the nitrogen-containing five-membered ring derivative represented by the general formula (B) or the general formula (B') are shown below, but not limited to these exemplified compounds.

[Chem. 49]

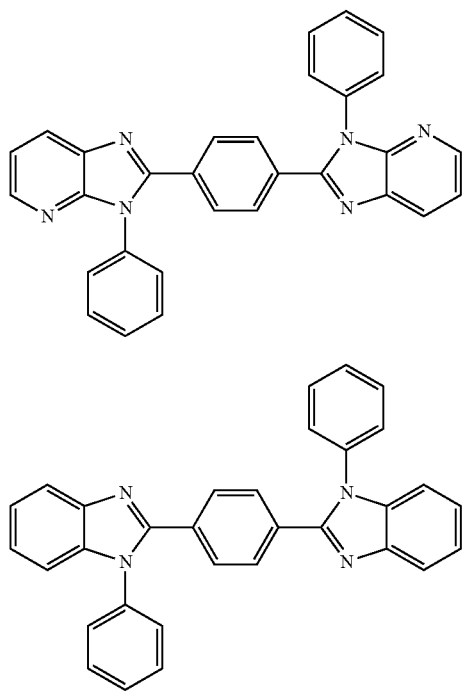

(B-1)

(B-2)

A compound forming each of the electron injecting layer and the electron transporting layer is also, for example, a compound having a structure obtained by combining an electron-deficient, nitrogen-containing five-membered ring skeleton or electron-deficient, nitrogen-containing six-membered ring skeleton and a substituted or unsubstituted indole skeleton, substituted or unsubstituted carbazole skeleton, or substituted or unsubstituted azacarbazole skeleton. In addition, a suitable electron-deficient, nitrogen-containing five-membered ring skeleton or electron-deficient, nitrogen-containing six-membered ring skeleton is a molecular skeleton such as a pyridine, pyrimidine, pyrazine, or triazine skeleton, or benzimidazole or imidazopyridine obtained when two or more of them fuse with each other.

Specific examples of the electron transporting compounds are shown below, but not limited thereto.

[Chem. 50]

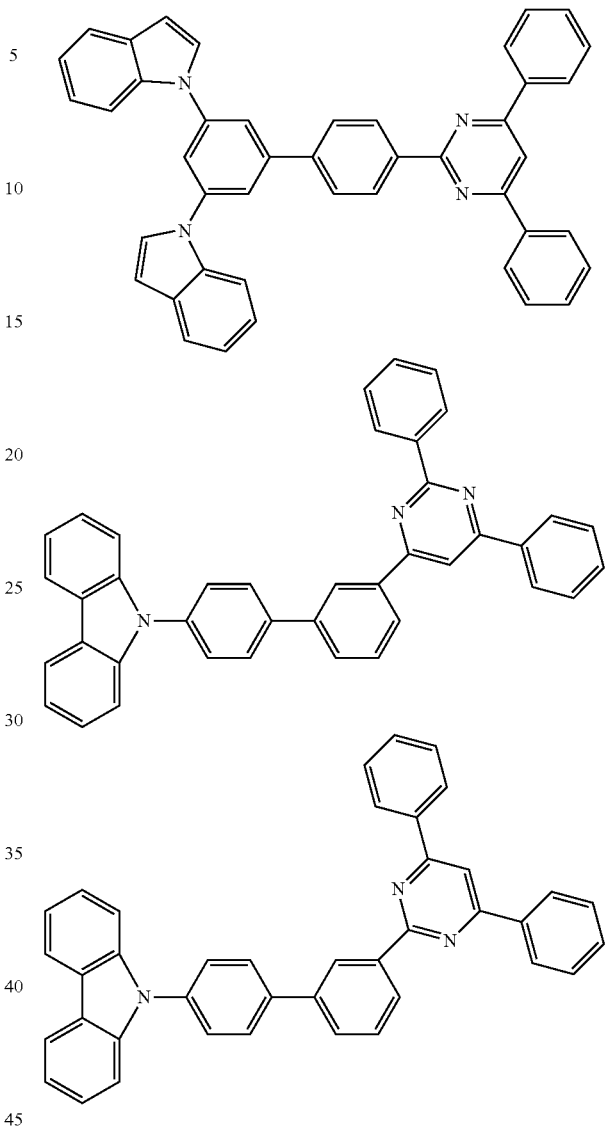

Each of the electron injecting layer and the electron transporting layer may be of a monolayer structure formed of one or two or more kinds of the materials, or may be of a multilayered structure formed of the plurality of layers identical to or different from each other in composition. Materials for those layers each preferably have a n-electron-deficient, nitrogen-containing heterocyclic group.

In addition, an insulator or semiconductor serving as an inorganic compound as well as the nitrogen-containing heterocyclic derivative is preferably used as a component of the electron injecting layer. When the electron injecting layer is formed of an insulator or semiconductor, current leakage can be effectively prevented, and the electron injecting property of the layer can be improved.

As the insulator, at least one metal compound selected from the group consisting of alkali metal chalcogenides, alkaline earth metal chalcogenides, alkali metal halides, and alkaline earth metal halides is preferably used. It is preferred that the electron injecting layer be formed of the alkali metal chalcogenide or the like since the electron injecting property can be further improved. To be specific, preferred examples of the alkali metal chalcogenide include $Li_2O$, $K_2O$, $Na_2S$, $Na_2Se$, and Na$_2$O, and preferred examples of the alkaline earth metal chalcogenide include CaO, BaO, SrO, BeO, BaS, and CaSe. In addition, preferred examples of the alkali metal halide include LiF, NaF, KF, LiCl, KCl, and NaCl. Further, preferred examples of the alkaline earth metal halide include fluorides such as CaF$_2$, BaF$_2$, SrF$_2$, MgF$_2$, and BeF$_2$ and halides other than the fluorides.

In addition, examples of the semiconductor include oxides, nitrides, and oxynitrides containing at least one element selected from the group consisting of Ba, Ca, Sr, Yb, Al, Ga, In, Li, Na, Cd, Mg, Si, Ta, Sb, and Zn. One kind of them may be used alone, or two or more kinds of them may be used in combination. In addition, it is preferred that the inorganic compound forming the electron injecting layer form a microcrystalline or amorphous insulating thin film. When the electron injecting layer is formed of the insulating thin film, a more uniform thin film can be formed, and defects of pixels such as dark spots can be decreased. It should be noted that examples of the inorganic compound include an alkali metal chalcogenide, an alkaline earth metal chalcogenide, an alkali metal halide, and an alkaline earth metal halide.

In addition, the reducing dopant can be preferably incorporated into the electron injecting layer in the present invention.

It should be noted that the thickness of each of the electron injecting layer and the electron transporting layer, which is not particularly limited, is preferably 1 to 100 nm.

An aromatic amine compound such as an aromatic amine derivative represented by the general formula (1) is suitably used in the hole injecting layer or hole transporting layer (a hole injecting/transporting layer is also included in this category).

[Chem. 51]

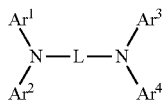
(I)

In the general formula (1), Ar$^1$ to Ar$^4$ each represent a substituted or unsubstituted aryl group having 6 to 50 ring carbon atoms, or a substituted or unsubstituted heterocyclic group having 5 to 50 ring atoms.

Examples of the substituted or unsubstituted aryl group having 6 to 50 ring carbon atoms include a phenyl group, a 1-naphthyl group, and a 2-naphthyl group.

Examples of the substituted or unsubstituted heterocyclic group having 5 to 50 ring atoms include a 1-pyrrolyl group, a 2-pyrrolyl group, and a 3-pyrrolyl group.

L represents a linking group. Specifically, L represents a substituted or unsubstituted arylene group having 6 to 50 ring carbon atoms, a substituted or unsubstituted heteroarylene group having 5 to 50 ring atoms, or a divalent group produced by binding two or more arylene groups or heteroarylene groups with a single bond, an ether bond, a thioether bond, an alkylene group having 1 to 20 carbon atoms, an alkenylene group having 2 to 20 carbon atoms, or an amino group. Examples of the arylene group having to 50 ring carbon atoms include a 1,4-phenylene group, a 1,2-phenylene group, a 1,3-phenylene group, a 1,4-naphthylene group, a 2,6-naphthylene group, a 1,5-naphthylene group, and a 9,10-anthranylene group.

When L represents a linking group formed of two or more arylene groups or heteroarylene groups, adjacent arylene groups or heteroarylene groups may form another ring by binding each other with a divalent group. Examples of the divalent group for forming the ring include a tetramethylene group, a pentamethylene group, a hexamethylene group, a diphenylmethane-2,2'-diyl group, a diphenylethane-3,3'-diyl group, and a diphenylpropane-4,4'-diyl group.

Examples of the substituent represented by Ar$^1$ to Ar$^4$ and L include a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted heteroaryloxy group having 5 to 50 ring atoms, a substituted or unsubstituted arylthio group having 6 to 50 ring carbon atoms, a substituted or unsubstituted heteroarylthio group having 5 to 50 ring atoms, a substituted or unsubstituted alkoxycarbonyl group having 2 to 50 carbon atoms, an amino group substituted with a substituted or unsubstituted aryl group having 6 to 50 ring carbon atoms or a substituted or unsubstituted heterocyclic group having 5 to 50 ring atoms, a halogen group, a cyano group, a nitro group, and a hydroxyl group.

Examples of the substituted or unsubstituted aryl group having 6 to 50 ring carbon atoms include a phenyl group, a 1-naphthyl group, and a 2-naphthyl group.

Examples of the substituted or unsubstituted heterocyclic group having 5 to 50 ring atoms, a 1-pyrrolyl group, a 2-pyrrolyl group, and a 3-pyrrolyl group.

Examples of the substituted or unsubstituted alkyl group having 1 to 50 carbon atoms include a methyl group and an ethyl group.

Examples of the substituted or unsubstituted cycloalkyl group having 3 to 50 carbon atoms include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms is a group represented by —OY. Examples of the group represented by Y include a methyl group and an ethyl group.

Examples of the substituted or unsubstituted aralkyl group having 7 to 50 carbon atoms include a benzyl group, a 1-phenylethyl group, and a 2-phenylethyl group.

The substituted or unsubstituted aryloxy group having 6 to 50 ring carbon atoms is represented as —OY', and examples of the group represented by Y' include a phenyl group, a 1-naphthyl group, and a 2-naphthyl group.

The substituted or unsubstituted heteroaryloxy group having 5 to 50 ring atoms is represented as —OZ', and examples of the group represented by Z' include a 2-pyrrolyl group, a 3-pyrrolyl group, a pyrazinyl group, a 2-pyridinyl group, a 3-pyridinyl group, and a 4-pyridinyl group.

The substituted or unsubstituted arylthio group having 6 to 50 ring carbon atoms is represented as —SY", and examples of the group represented by Y" include a phenyl group, a 1-naphthyl group, and a 2-naphthyl group.

The substituted or unsubstituted heteroarylthio group having 5 to 50 ring atoms is represented as —SZ", and examples of the group represented by Z" include a 2-pyrrolyl group, a 3-pyrrolyl group, a pyrazinyl group, a 2-pyridinyl group, a 3-pyridinyl group, and a 4-pyridinyl group.

The substituted or unsubstituted alkoxycarbonyl group having 2 to 50 carbon atoms is represented as —COOZ, and examples of the group represented by Z include a methyl group, an ethyl group, a propyl group, an isopropyl group, a n-butyl group, a s-butyl group, an isobutyl group, and a t-butyl group.

The amino group substituted with a substituted or unsubstituted aryl group having 6 to 50 ring carbon atoms or a substituted or unsubstituted heterocyclic group having 5 to 50 ring atoms is represented as —NPQ, and examples of the groups represented by P and Q include a phenyl group, a 1-naphthyl group, and a 2-naphthyl group.

Specific examples of the compound represented by the general formula (I) are shown below, however, the compound is not limited thereto.

[Chem. 52]

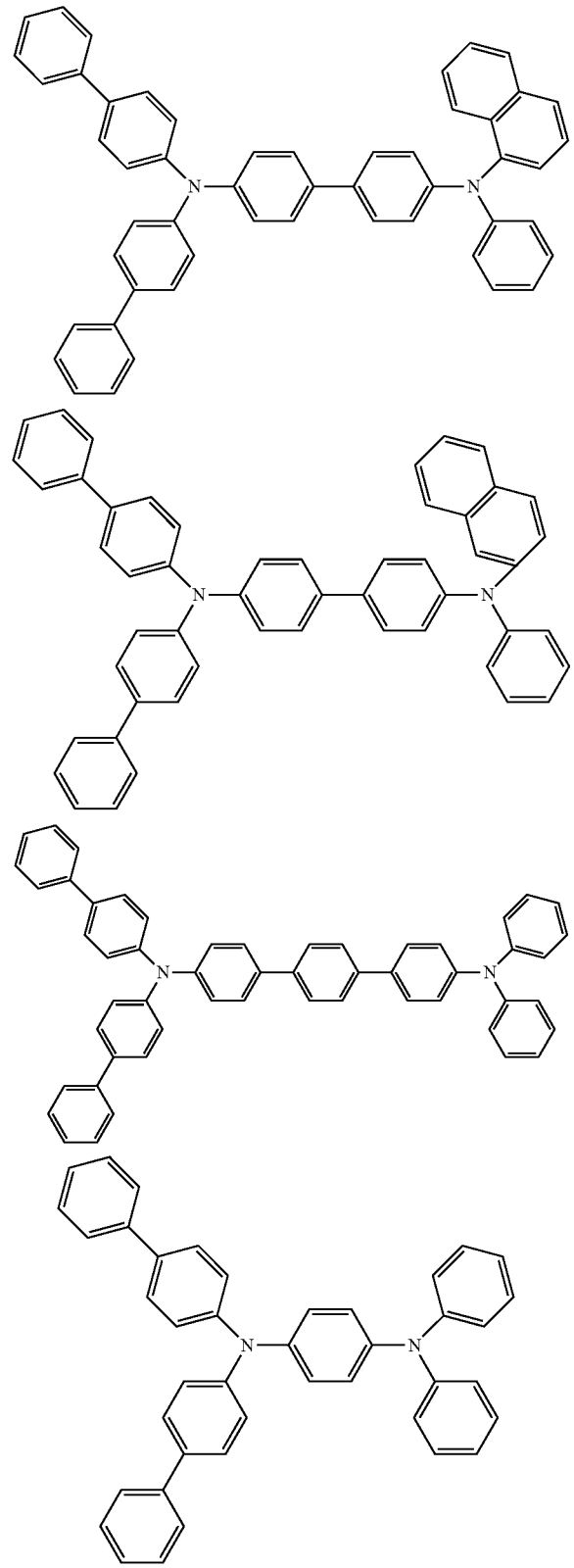

In addition, an aromatic amine represented by the following general formula (II) is also suitably used in the formation of the hole injecting layer or hole transporting layer.

[Chem. 53]

(II)

In the general formula (II), the definitions of $Ar_1$ to $Ar_3$ are the same as those of $Ar^1$ to $Ar^4$ in the general formula (1). Specific examples of the compound represented by the general formula (II) are shown below, but not limited thereto.

[Chem. 54]

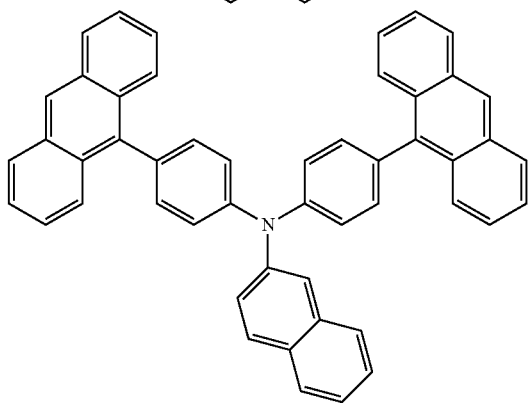

In the present invention, the anode in the organic EL device has the function of injecting holes into the hole transporting layer or the light emitting layer. It is effective that the anode has a work function of 4.5 eV or more. Specific examples of the material for the anode used in the present invention include indium tin oxide alloys (ITO), tin oxide (NESA), gold, silver, platinum, and copper. In addition, as the cathode, a material having a small work function is preferred in view to inject an electron into an electron injecting layer or a light emitting layer. Examples of the material for the cathode are not particularly limited, and specifically, indium, aluminum, magnesium, a magnesium-indium alloy, a magnesium-aluminum alloy, an aluminum-lithium alloy, an aluminum-scandium-lithium alloy, a magnesium-silver alloy, or the like may be used.

The method of forming each of the layers in the organic EL device of the present invention is not particularly limited. A conventionally known process such as a vacuum vapor deposition process or a spin coating process can be used for the formation method. The organic thin film layer which is used in the organic EL device of the present invention and which contain the compound represented by the formula (1) can be formed in accordance with a known process such as a vacuum vapor deposition process or a molecular beam epitaxy process (MBE process) or, using a solution prepared by dissolving the compounds into a solvent, in accordance with a coating process such as a dipping process, a spin coating process, a casting process, a bar coating process, or a roll coating process.

The thickness of each organic layer in the organic EL device of the present invention is not particularly limited. In general, an excessively thin layer tends to have defects such as pin holes, whereas an excessively thick layer requires a high applied voltage to decrease the efficiency. Therefore, a thickness in the range of several nanometers to 1 μm is typically preferred.

EXAMPLES

Next, the present invention is described in more detail by way of synthesis examples and examples. Note that the present invention is not limited to the following synthesis examples and examples.

Methods of evaluating an organic EL device are as described below.

(1) External Quantum Efficiency (%)

Its external quantum efficiency at a luminance of 1,000 cd/m² was measured with a luminance meter (spectral luminance radiometer CS-1000 manufactured by Minolta) at 23° C. under a dry nitrogen gas atmosphere.

(2) Half Lifetime (Hour(s))

A continuous energization test (direct current) was performed at an initial luminance of 1,000 cd/m² to measure a time period required for the initial luminance to reduce by half.

(3) Voltage (V)

A voltage was applied to the device, which had been subjected to electric wiring, with a KEITHLY 236 SOURCE MEASURE UNIT at 23° C. under a dry nitrogen gas atmosphere to cause the device to emit light, and then the voltage applied to the device was measured by subtracting a voltage applied to a wiring resistance except the device.

Synthesis Example 1

Synthesis of Compound (1)

(1) Synthesis of Compound (1-1)

[Chem. 55]

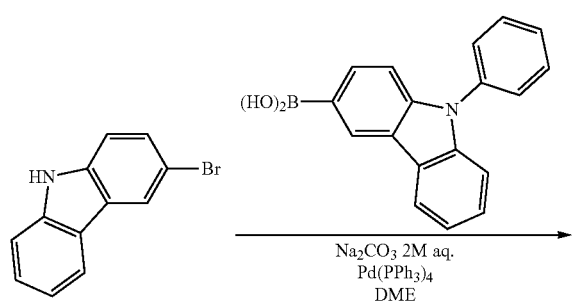

Na₂CO₃ 2M aq.
Pd(PPh₃)₄
DME

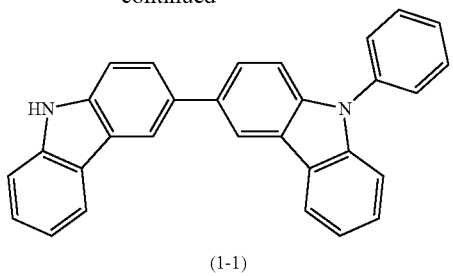

(1-1)

49.22 Grams (200 mmol) of 3-bromocarbazole, 63.17 g (220 mmol) of 9-phenylcarbazole-3-boronic acid, a 2-M aqueous solution of sodium carbonate (200 ml), and 400 ml of 1,2-dimethoxyethane were loaded into a three-necked flask. Next, 2.31 g (2 mmol) of Pd(PPh₃)₄ were added to the mixture and then the whole was refluxed under a nitrogen atmosphere for 24 hours.

After the completion of the reaction, the sample was transferred to a separating funnel and extracted with dichloromethane several times. The resultant was dried with anhydrous magnesium sulfate, and was then filtered and concentrated. The concentrate was purified by silica gel chromatography (dichloromethane:hexane=6:4), and was then washed by being dispersed in methanol. Thus, a white solid (Compound (1-1)) was obtained.

Identification was performed by ¹H-NMR and molecular weight measurement based on FD/MS.

Product amount: 50.6 g
Yield: 62%

(2) Synthesis of Compound (1)

[Chem. 56]

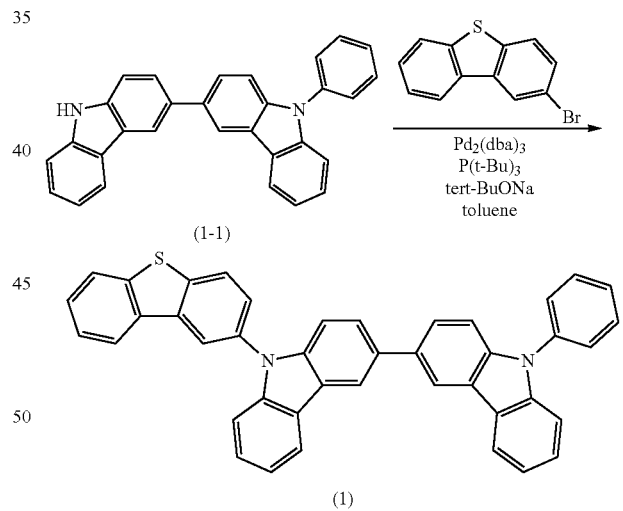

4.08 Grams (10 mmol) of Compound (1-1), 3.16 g (12 mmol) of 2-bromodibenzothiophene, 1.92 g (20 mmol) of sodium tert-butoxide, 183 mg (0.2 mmol) of Pd₂(dba)₃, 0.4 ml (0.8 mmol) of a solution of tri-tert-butylphosphine in toluene (2.0 M), and 40 ml of toluene were loaded into a three-necked flask, and then the mixture was refluxed under a nitrogen atmosphere for 16 hours.

After the completion of the reaction, the sample solution was cooled to room temperature. After that, the sample solution was diluted with toluene (500 ml) and then the diluted solution was filtered by being passed through Celite. The filtrate was further passed through a silica gel short column. Thus, a raw material impurity component was removed. After that, the remainder was purified by silica gel chromatography (hexane:toluene=5:5). After that, the purified product was washed by being dispersed in a mixed solvent of ethyl acetate and hexane. Thus, a white solid (Compound (1)) was obtained. It should be noted that the molecular weight of Compound (1) is 755.92.

Identification was performed by $^1$H-NMR and molecular weight measurement based on FD/MS.

Product amount: 2.84 g

Yield: 48%

Synthesis Example 2

Synthesis of Compound (70)

[Chem. 57]

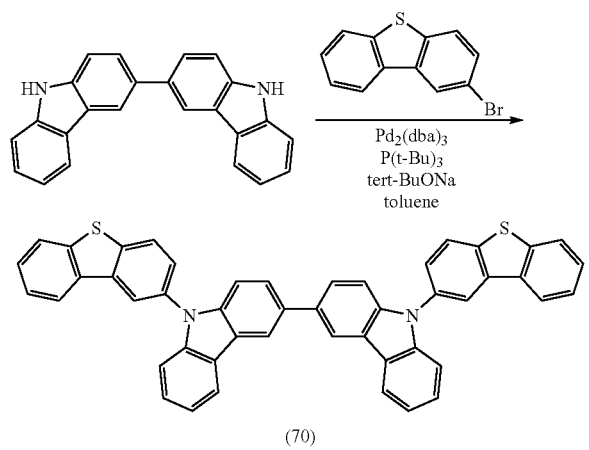

(70)

3.32 Grams (10 mmol) of 3,3'-bicarbazole, 6.32 g (24 mmol) of 2-bromodibenzothiophene, 3.84 g (40 mmol) of sodium tert-butoxide, 137 mg (0.15 mmol) of Pd$_2$(dba)$_3$, 0.3 ml (0.6 mmol) of a solution of tri-tert-butylphosphine in toluene (2.0 M), and 40 ml of toluene were loaded into a three-necked flask, and then the mixture was refluxed under a nitrogen atmosphere for 24 hours.

After the completion of the reaction, 500 ml of toluene were added to the sample solution and then the mixture was refluxed in a stream of nitrogen for 1 hour. After that, the resultant was cooled to room temperature and then filtered by being passed through Celite. The filtrate was further passed through a silica gel short column. Thus, a raw material impurity component was removed. After that, the remainder was recrystallized with ethyl acetate twice. Thus, a pale brownish solid (Compound (70)) was obtained. It should be noted that the molecular weight of Compound (70) is 696.88.

Identification was performed by $^1$H-NMR and molecular weight measurement based on FD/MS.

Product amount: 3.03 g

Yield: 43%

Synthesis Example 3

Synthesis of Compound (85)

(1) Synthesis of Compound (85-1)

[Chem. 58]

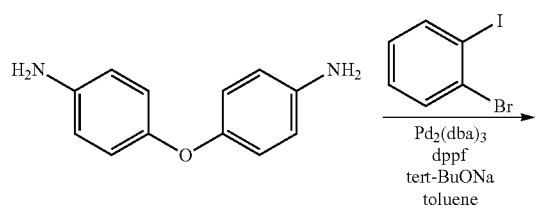

-continued

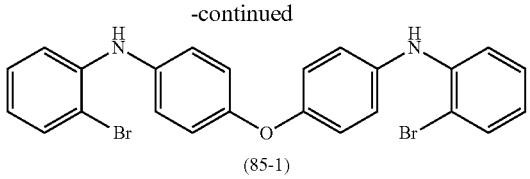

(85-1)

48.1 Grams (240 mmol) of 4,4'-diaminodiphenylether, 149.4 g (528 mmol) of 2-bromoiodobenzene, 92.3 g (960 mmol) of sodium tert-butoxide, 2.2 g (2.4 mmol) of Pd$_2$(dba)$_3$, 2.66 g (4.8 mmol) of 1,1'-Bis(diphenylphosphino)ferrocene, and 960 ml of toluene were loaded into a three-necked flask, and then the mixture was stirred under heat under a nitrogen atmosphere at 80° C. for 8 hours.

After the completion of the reaction, 500 ml of water were added to the sample solution, and then the mixture was transferred to a separating funnel and extracted with ethyl acetate several times. The resultant was dried with anhydrous magnesium sulfate, and was then filtered and concentrated. The concentrate was purified by silica gel chromatography (toluene:hexane=3:7). Thus, a colorless viscous body (Compound (85-1)) was obtained.

Identification was performed by $^1$H-NMR and molecular weight measurement based on FD/MS.

Product amount: 109.68 g

Yield: 90%

(2) Synthesis of Compound (85-2)

[Chem. 59]

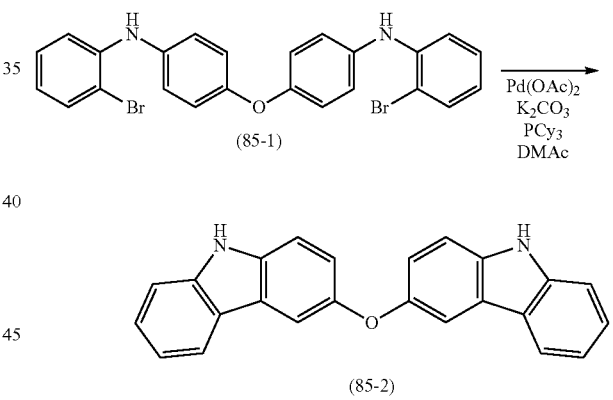

28.01 Grams (54.9 mmol) of Compound (85-1), 2.47 g (10.98 mmol) of palladium acetate, 30.35 g (mmol) of potassium carbonate, 274 ml of N,N-dimethylacetamide, and 30.8 ml (21.96 mmol) of tricyclohexylphosphine (toluene solution (20 wt %)) were loaded into a three-necked flask, and then the mixture was stirred under heat under a nitrogen atmosphere at 150° C. for 8 hours.

After the completion of the reaction, an inorganic salt was separated by filtration by passing the sample solution through Celite. The filtrate was poured into 1 l of water and then the precipitated sample was taken by filtration. The sample was washed by being dispersed in a mixed solvent containing 200 ml of methanol and 200 ml of ethyl acetate, and was then taken by filtration and dried in a vacuum (60° C., 4 hours). Thus, a white solid (Compound (85-2)) was obtained.

Identification was performed by $^1$H-NMR and molecular weight measurement based on FD/MS.

Product amount: 13.63 g

Yield: 71%

(3) Synthesis of Compound (85)

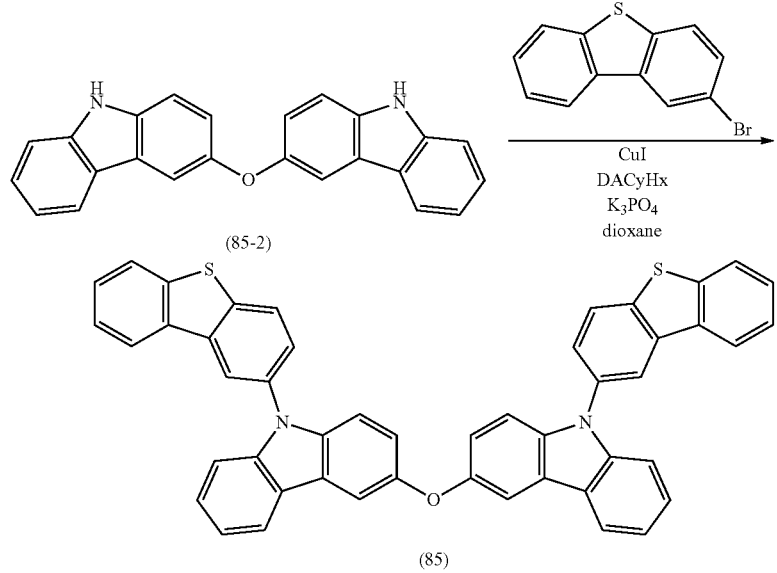

(85-2)

[Chem. 60]

(85)

5.23 Grams (15 mmol) of Compound (85-2), 9.47 g (36 mmol) of 2-bromodibenzothiophene, 12.74 g (60 mmol) of K$_3$PO$_4$, 1.43 g (7.5 mmol) of CuI, 1.80 ml (15 mmol) of trans-1,2-diaminocyclohexane, and 15 ml of 1,4-dioxane were loaded into a three-necked flask, and then the mixture was refluxed under a nitrogen atmosphere for 24 hours.

After the completion of the reaction, the resultant was diluted with toluene (200 ml) and then the diluted solution was filtered by being passed through Celite. Thus, an inorganic salt was removed. Then, the remainder was concentrated. The concentrate was purified by silica gel chromatography (toluene:hexane=5:5) and then recrystallized with ethyl acetate twice. Thus, a white solid (Compound (85)) was obtained. It should be noted that the molecular weight of Compound (85) is 712.88.

Identification was performed by $^1$H-NMR and molecular weight measurement based on FD/MS.
Product amount: 1.5 g
Yield: 21%

Synthesis Example 4

Synthesis of Compound (6)

(1) Synthesis of Compound (6-1)

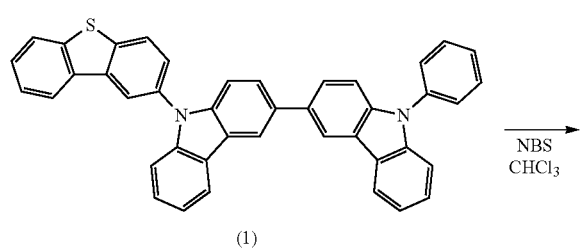

(1)

[Chem. 61]

NBS
CHCl$_3$

-continued

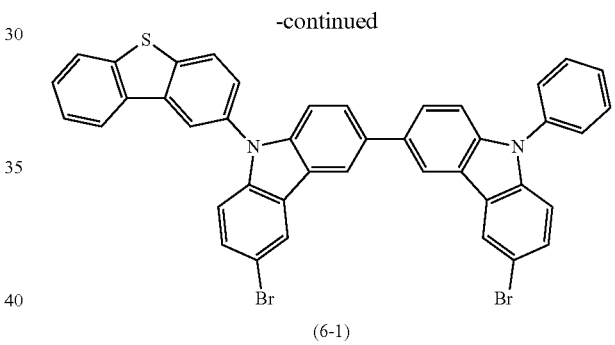

(6-1)

11.81 Grams (20 mmol) of Compound (1) and chloroform (400 ml) were loaded into a three-necked flask to dissolve the compound. 7.48 Grams (42 mmol) of N-bromosuccinimide dissolved in 40 ml of N,N-dimethylformamide were dropped to the solution over 10 minutes. After having been stirred at room temperature for 16 hours, the sample was diluted with chloroform (500 ml), transferred to a separating funnel, and washed with a salt solution twice. The washed product was dried with anhydrous magnesium sulfate, and was then filtered and concentrated. The concentrate was purified by silica gel chromatography (hexane:toluene=3:7). Thus, a pale brownish solid (Compound (6-1)) was obtained.

Identification was performed by $^1$H-NMR and molecular weight measurement based on FD/MS.
Product amount: 14.2 g
Yield: 95%

(2) Synthesis of Compound (6)

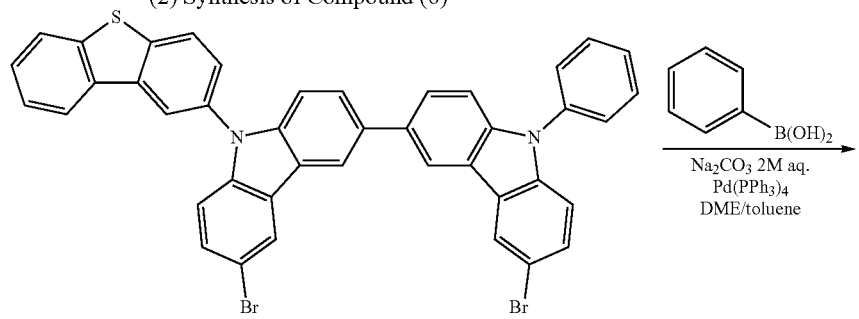

(6-1)

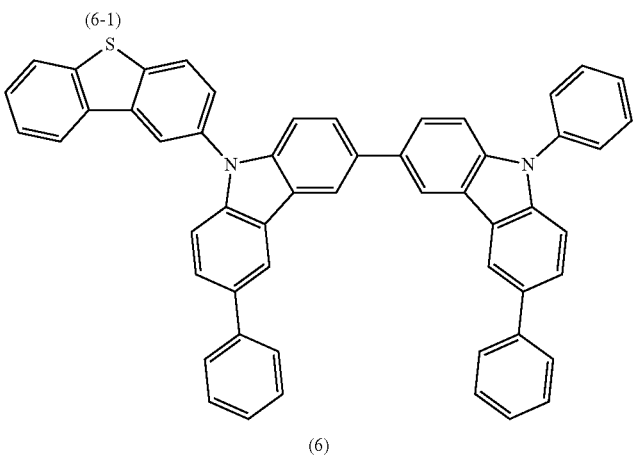

(6)

7.43 Grams (10 mmol) of Compound (6-1), 3.66 g (24 mmol) of phenylboronic acid, a 2-M aqueous solution of sodium carbonate (20 ml), 1,2-dimethoxyethane (80 ml), and toluene (80 ml) were loaded into a three-necked flask. Next, 0.58 g (0.5 mmol) of Pd(PPh$_3$)$_4$ were added to the mixture and then the whole was refluxed under a nitrogen atmosphere for 18 hours.

After the completion of the reaction, the solvent was removed with an evaporator. The sample was washed by being dispersed in methanol (200 ml) and water (200 ml) added thereto, and then the precipitated sample was taken by filtration. The sample was purified by silica gel chromatography (hexane:toluene=4:6) and then recrystallized from ethyl acetate. Thus, a solid (Compound (6)) was obtained. It should be noted that the molecular weight of Compound (6) is 742.93.

Identification was performed by $^1$H-NMR and molecular weight measurement based on FD/MS.
Product amount: 4.53 g
Yield: 61%

Synthesis Example 5

Synthesis of Compound (104)

[Chem. 63]

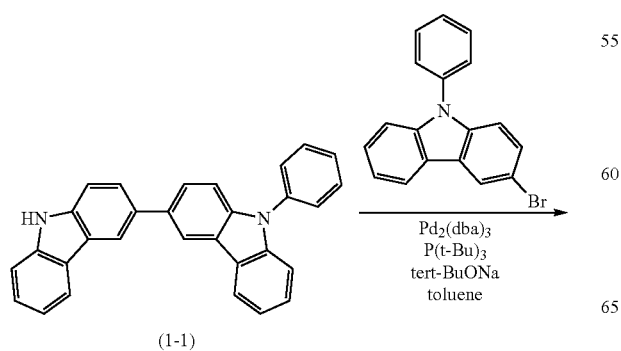

(1-1)

-continued

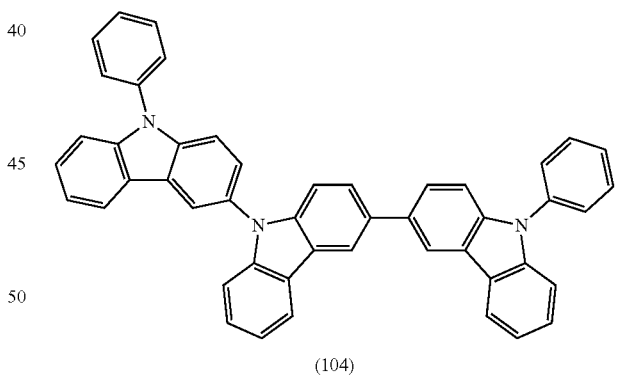

(104)

Compound (104) was synthesized in the same manner as in the synthesis of Compound (1) except that 2-bromodibenzothiophene as a raw material was changed to 3-bromo-9-phenylcarbazole. It should be noted that the molecular weight of Compound (104) is 649.78.

Synthesis Example 6

Synthesis of Compound (160)

(1) Synthesis of Compound (160-1)

[Chem. 64]

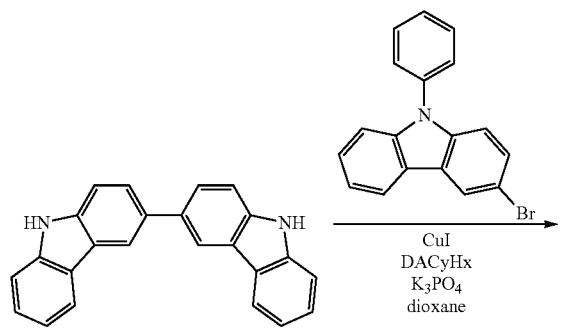

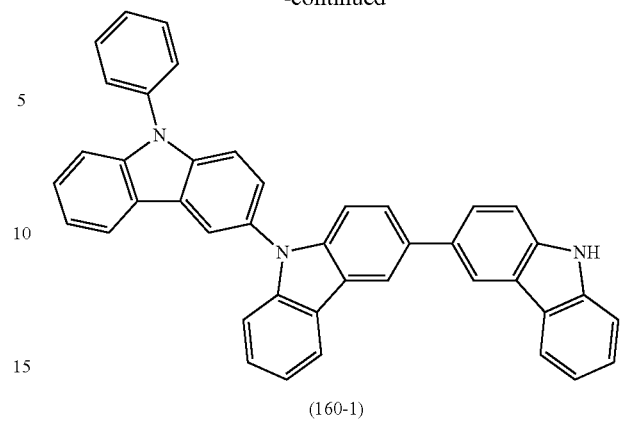

33.24 Grams (100 mmol) of 3,3'-bicarbazole, 29.0 g (90 mmol) of 3-bromo-9-phenylcarbazole, 63.68 g (300 mmol) of $K_3PO_4$, 3.81 g (20 mmol) of CuI, 7.2 ml (60 mmol) of trans-1,2-diaminocyclohexane, and 200 ml of 1,4-dioxane were loaded into a three-necked flask, and then the mixture was refluxed under a nitrogen atmosphere for 20 hours.

After the completion of the reaction, the resultant was diluted with dioxane (500 ml) and then the diluted solution was filtered by being passed through Celite. Thus, an inorganic salt was removed. Then, the remainder was concentrated. The concentrate was purified by silica gel chromatography (hexane:dicholoromethane=5:5), and was then washed by being dispersed in methanol. Thus, a white solid (Compound (160-1)) was obtained.

Identification was performed by $^1$H-NMR and molecular weight measurement based on FD/MS.
Product amount: 17.2 g
Yield: 30%

(2) Synthesis of Compound (160)

[Chem. 65]

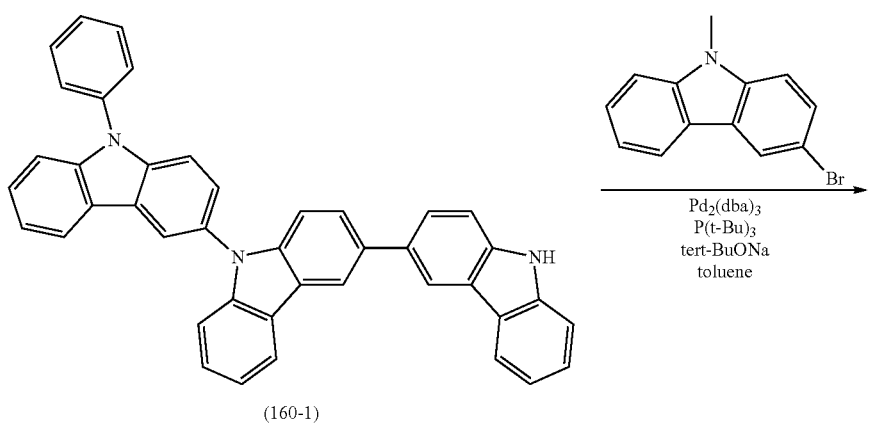

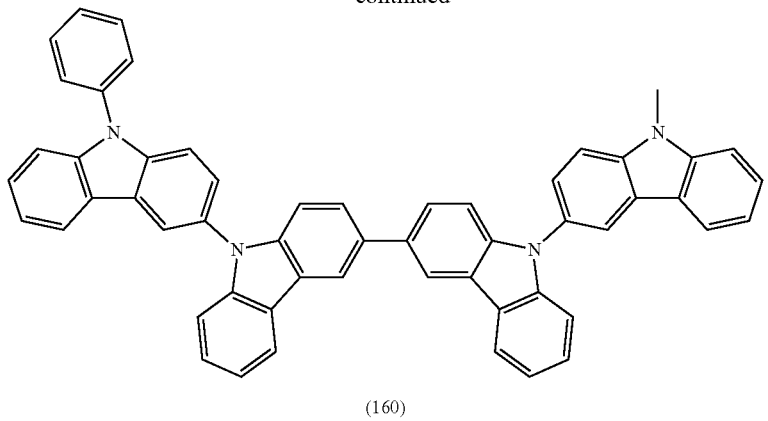
(160)
Compound (160) was synthesized in the same manner as in the synthesis of Compound (1) except that Compound (1-1) and 2-bromodibenzothiophene as a raw material were changed to Compound (160-1) and 3-bromo-9-methylcarbazole, respectively. It should be noted that the molecular weight of Compound (160) is 752.9.
Synthesis Example 7
Synthesis of Compound (194)
[Chem. 66]
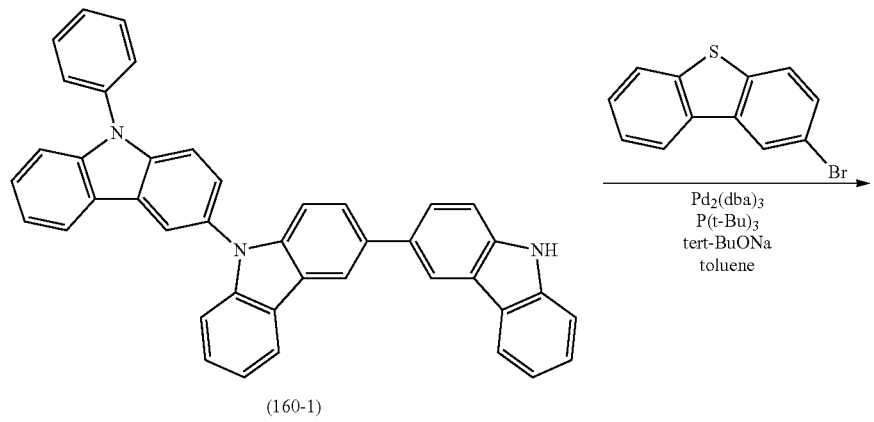
(160-1)
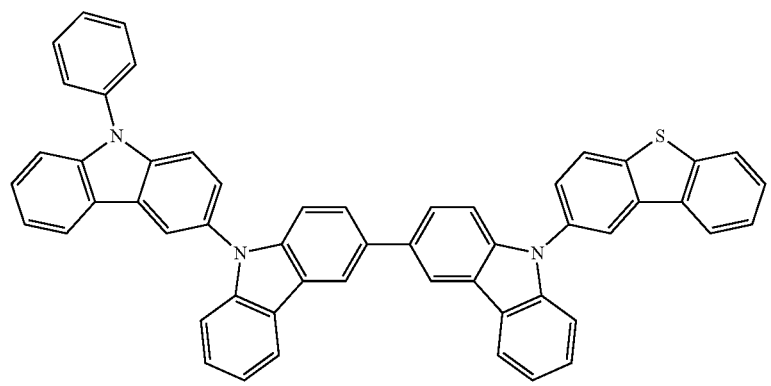
(194)

Compound (194) was synthesized in the same manner as in the synthesis of Compound (160) except that the compound 3-bromo-9-methylcarbazole as a raw material was changed to 2-bromodibenzothiophene. It should be noted that the molecular weight of Compound (194) is 755.92.

Synthesis Example 8

Synthesis of Compound (H-16)

(1) Synthesis of Compound (H-16-1)

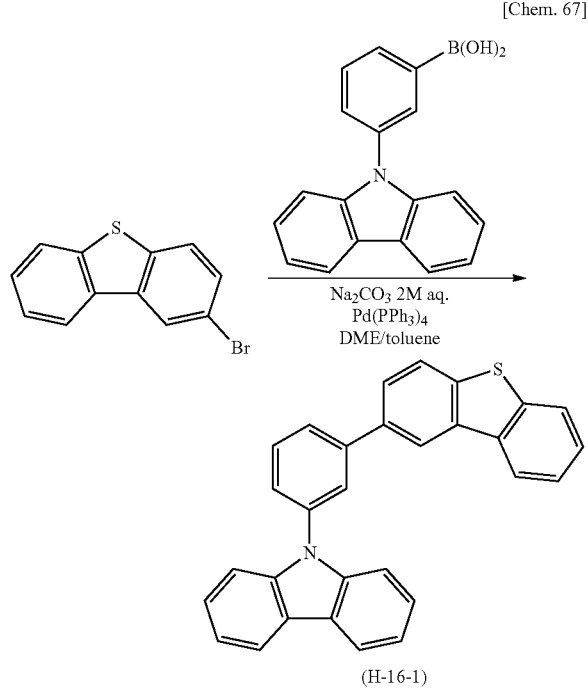

[Chem. 67]

(H-16-1)

26.32 Grams (100 mmol) of 2-bromodibenzothiophene, 31.58 g (110 mmol) of 3-(9-carbazolyl)phenylboronic acid, a 2-M aqueous solution of sodium carbonate (100 ml), 1,2-dimethoxyethane (100 ml), and toluene (100 ml) were loaded into a three-necked flask. Next, 2.31 g (2 mmol) of Pd(PPh$_3$)$_4$ were added to the mixture and then the whole was refluxed under a nitrogen atmosphere for 10 hours.

After the completion of the reaction, the sample was transferred to a separating funnel and extracted with dichloromethane several times. The resultant was dried with anhydrous magnesium sulfate, and was then filtered and concentrated. The concentrate was purified by silica gel chromatography (dichloromethane:hexane=4:6), was then washed by being dispersed in methanol, taken by filtration, and dried in a vacuum (60° C., 6 hours). Thus, a white solid (Compound (H-16-1)) was obtained.

Identification was performed by $^1$H-NMR and molecular weight measurement based on FD/MS.

Product amount: 39.6 g

Yield: 93%

(2) Synthesis of Compound (H-16-2)

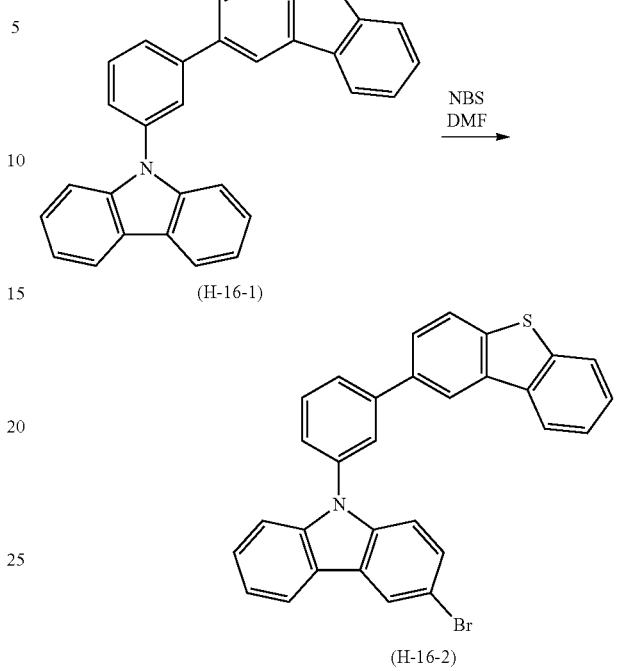

[Chem. 68]

(H-16-1)

(H-16-2)

18.72 Grams (44 mmol) of Compound (H-16-1) and N,N-dimethylformamide (200 ml) were loaded into a three-necked flask to dissolve the compound, and then the solution was cooled to 0° C. with ice water. 7.12 Grams (40 mmol) of N-bromosuccinimide dissolved in N,N-dimethylformamide (40 ml) were dropped to the solution over 10 minutes. After that, the mixture was stirred while being held at 0° C. for 4 hours, and was then stirred for 16 hours at room temperature. After the completion of the reaction, the sample solution was diluted with toluene (300 ml), transferred to a separating funnel, and washed with water twice. The toluene solution was dried with anhydrous magnesium sulfate and passed through a silica gel short column. Then, the solution was concentrated and exsiccated. Thus, a white solid (Compound (H-16-2)) was obtained.

Identification was performed by molecular weight measurement based on FD/MS.

Product amount: 20.5 g (3) Synthesis of Compound (H-16)

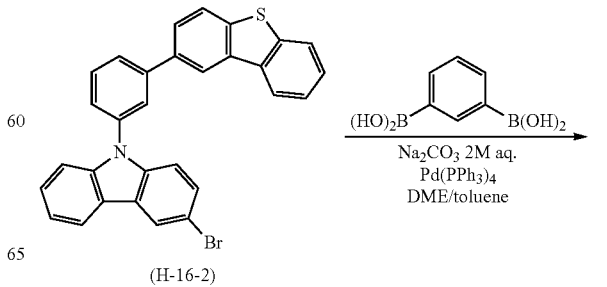

[Chem. 69]

(H-16-2)

-continued

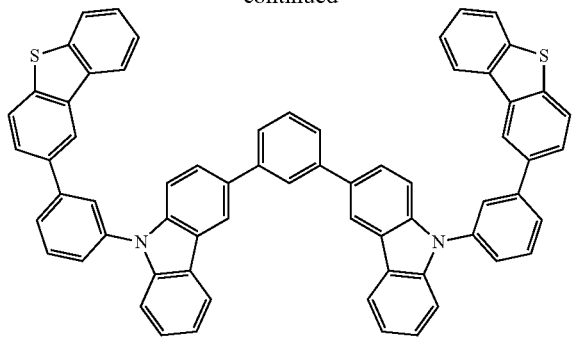

(H-16)

6.05 Grams (12 mmol) of Compound (H-16-2), 0.83 g (5 mmol) of 1,3-benzenediboronic acid, a 2-M aqueous solution of sodium carbonate (10 ml), 1,2-dimethoxyethane (20 ml), and toluene (20 ml) were loaded into a three-necked flask. Next, 0.29 g (0.25 mmol) of Pd (PPh$_3$)$_4$ were added to the mixture and then the whole was refluxed under a nitrogen atmosphere for 10 hours.

After the completion of the reaction, the sample solution was cooled to room temperature. After that, the sample solution was washed by being dispersed in methanol (200 ml) and water (200 ml) added thereto, and then the precipitated sample was taken by filtration. The sample was dried in a vacuum (60° C., 5 hours) and then purified by silica gel chromatography (toluene:hexane=7:3). Thus, a white solid (Compound (H-16)) was obtained.

Identification was performed by $^1$H-NMR and molecular weight measurement based on FD/MS.
Product amount: 2.64 g
Yield: 57%

Example 1

A glass substrate provided with an ITO electrode line having a thickness of 130 nm (manufactured by GEOMATEC Co., Ltd.) was subjected to ultrasonic cleaning in isopropyl alcohol for 5 minutes. After that, the substrate was subjected to UV-ozone cleaning for 30 minutes.

The glass substrate provided with an ITO electrode line thus cleaned was mounted on a substrate holder of a vacuum deposition apparatus. First, Compound (HT) was deposited from the vapor onto the surface of the glass substrate on the side where an ITO electrode line was formed by resistance heating so as to cover the ITO electrode line, whereby a thin film having a thickness of 60 nm was formed. The film formation rate was set to 1 Å/s. The thin film functions as a hole injecting layer and a hole transporting layer.

Next, Compound (1) and Compound (BD) were simultaneously deposited from the vapor onto the hole injecting/transporting layer by resistance heating to form a thin film having a thickness of 30 nm. At this time, the vapor deposition was performed so that a mass ratio of Compound (BD) with respect to the total mass of Compound (1) and Compound (BD) was 10%. The film formation rates of Compound (1) and Compound (BD) were set to 1.0 Å/s and 0.11 Å/s, respectively. The thin film functions as a phosphorescent light emitting layer.

Next, Compound (HB) was deposited from the vapor onto the phosphorescent light emitting layer by resistance heating to form an HB film having a thickness of 10 nm. The film formation rate was 1 Å/s. The HB film functions as a hole blocking layer.

A tris(8-quinolinol) aluminum (Alq) complex was deposited from the vapor onto the hole blocking layer at a film formation rate of 1 Å/s (to have a thickness of 30 nm). The film functions as an electron injecting layer.

After that, LiF was deposited from the vapor onto the electron injecting layer at a film formation rate of 0.1 Å/s (to have a thickness of 0.5 nm). Metal Al was deposited from the vapor onto the LiF film at a film formation rate of 1 Å/s to form a metal cathode (having a thickness of 100 nm). Thus, an organic EL device was obtained.

[Chem. 70]

Compound

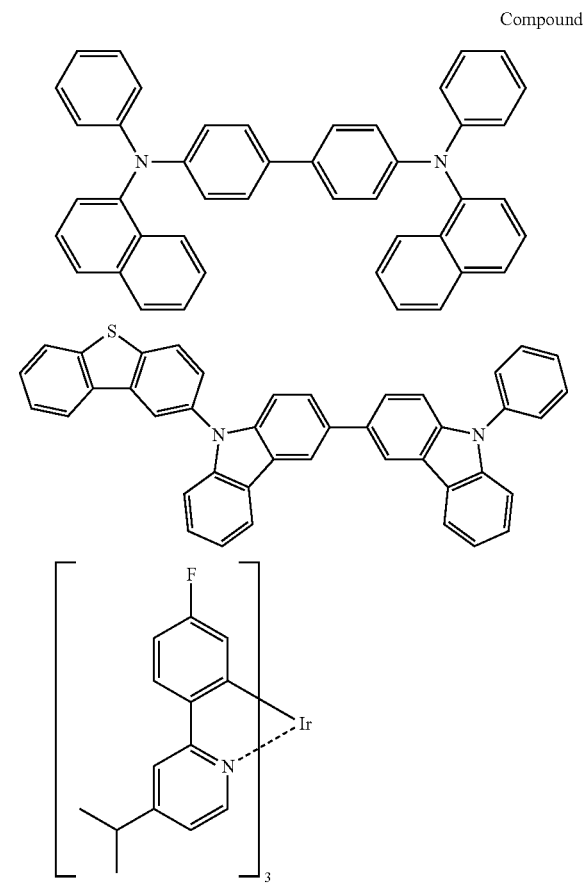

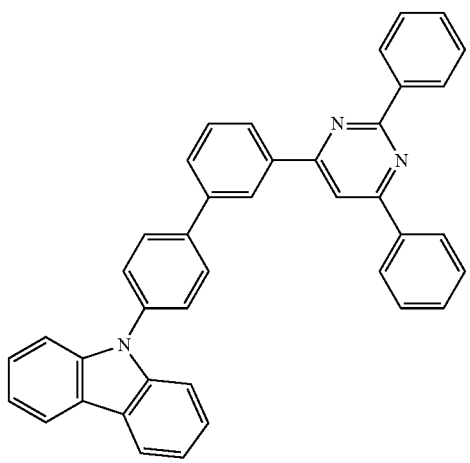

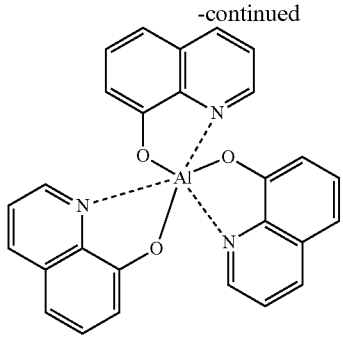

Exemplified Compound

[Chem. 71]

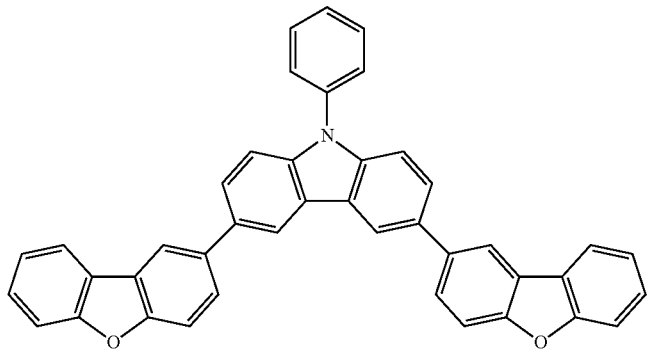

Compound (H1)

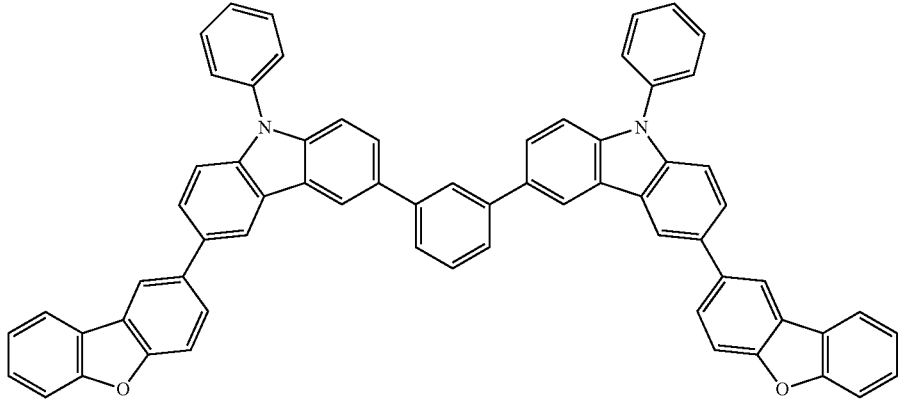

Compound (H2)

Examples 2 to 4

Organic EL devices were each produced in the same manner as in Example 1 except that a host material (Exemplified Compounds 70, 85, and 6) listed in Table 1 was used instead of Exemplified Compound (1) in Example 1.

Comparative Examples 1 to 6

Organic EL devices were produced in the same manner as in Example 1 except that the following compounds were used instead of Compound (1) as shown in Table 1.

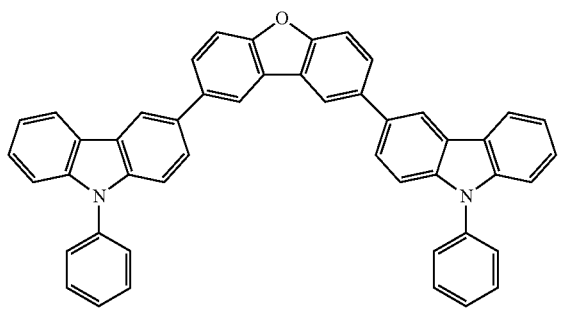

Compound (H4)

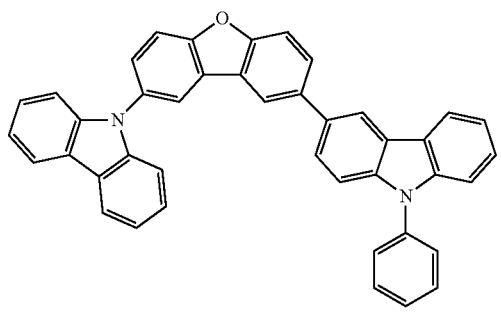

Compound (H5)

-continued
Compound (H6)

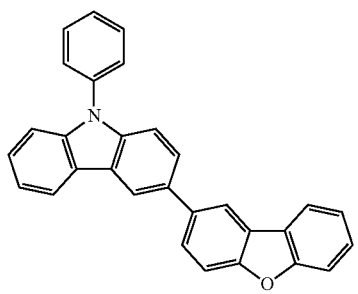
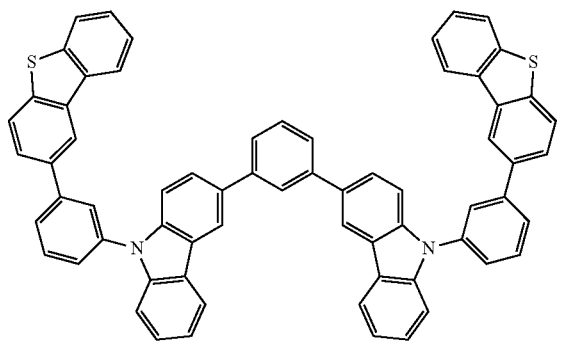

The organic EL devices produced in the examples and the comparative examples were each evaluated for the items, i.e., "external quantum efficiency," "half lifetime," and "voltage." Table 1 below summarizes the results.

TABLE 1

| | Host | Voltage (V) | External quantum efficiency (%) | Half lifetime (hour(s)) |
|---|---|---|---|---|
| Example 1 | Compound (1) | 7.5 | 9.6 | 900 |
| Example 2 | Compound (70) | 7.3 | 8.1 | 950 |
| Example 3 | Compound (85) | 7.1 | 11.4 | 700 |
| Example 4 | Compound (6) | 7.0 | 7.8 | 1000 |
| Comparative Example 1 | H1 | 8.8 | 7.0 | 700 |
| Comparative Example 2 | H2 | 8.8 | 7.1 | 650 |
| Comparative Example 3 | H4 | 9.3 | 6.4 | 450 |
| Comparative Example 4 | H5 | 9.5 | 6.9 | 480 |
| Comparative Example 5 | H6 | 9.3 | 6.9 | 250 |
| Comparative Example 6 | H-16 | — | — | — |

It was confirmed from the results of Table 1 above that the organic EL devices of the examples each using the compound of the present application each had high efficiency and a long lifetime. It was also confirmed that the compound of the present application enabled low-voltage driving. In other words, it was found that the use of the compound of the present application enabled the production of an organic EL device that consumed low power.

It should be noted that in Comparative Example 6, the decomposition of Compound H-16 at the time of its sublimation step was observed. As a result, no device could be produced in Comparative Example 6.

Example 5

A glass substrate provided with an ITO electrode line having a thickness of 130 nm (manufactured by GEOMATEC Co., Ltd.) was subjected to ultrasonic cleaning in isopropyl alcohol for 5 minutes. After that, the substrate was subjected to UV-ozone cleaning for 30 minutes.

The glass substrate provided with an ITO electrode line thus cleaned was mounted on a substrate holder of a vacuum deposition apparatus. First, Compound (HT) was deposited from the vapor onto the surface of the glass substrate on the side where an ITO electrode line was formed by resistance heating so as to cover the ITO electrode line, whereby a thin film having a thickness of 50 nm was formed. The film formation rate was set to 1 Å/s. The thin film functions as a hole injecting layer and a hole transporting layer.

Next, Compound (6) was deposited from the vapor onto the hole transporting layer by resistance heating to form a thin film having a thickness of 10 nm. The film formation rate was set to 1 Å/s. The thin film functions as a barrier layer.

Next, the following Compound (A-1) and Compound (BD) were simultaneously deposited from the vapor onto the barrier layer by resistance heating to form a thin film having a thickness of 30 nm. At this time, the vapor deposition was performed so that a mass ratio of Compound (BD) with respect to the total mass of Compound (A-1) and Compound (BD) was 10%. The film formation rates of Compound (A-1) and Compound (BD) were set to 1.0 Å/s and 0.11 Å/s, respectively. The thin film functions as a phosphorescent light emitting layer.

Next, Compound (HB) was deposited from the vapor onto the phosphorescent light emitting layer by resistance heating to form an HB film having a thickness of 10 nm. The film formation rate was 1 Å/s. The HB film functions as a hole blocking layer.

A tris(8-quinolinol) aluminum (Alq) complex was deposited from the vapor onto the hole blocking layer at a film formation rate of 1 Å/s (to have a thickness of 30 nm). The film functions as an electron injecting layer.

After that, LiF was deposited from the vapor onto the electron injecting layer at a film formation rate of 0.1 Å/s (to have a thickness of 0.5 nm). Metal Al was deposited from the vapor onto the LiF film at a film formation rate of 1 Å/s to form a metal cathode (having a thickness of 100 nm). Thus, an organic EL device was obtained.

[Chem. 72]
Compound

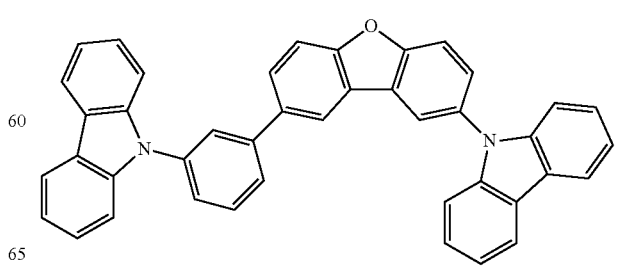

Examples 6 to 8

Organic EL devices were each produced in the same manner as in Example 5 except that a compound listed in Table 2 was used in a barrier layer instead of Compound (6) in Example 5.

Comparative Example 6

An organic EL device was produced in the same manner as in Example 5 except that Compound (HT) was used instead of Compound (6).

TABLE 2

| Barrier layer | | Voltage (V) | External quantum efficiency (%) | Half lifetime (hour(s)) |
|---|---|---|---|---|
| Example 5 | Compound (6) | 8.6 | 15.3 | 1,000 |
| Example 6 | Compound (104) | 8.5 | 16.9 | 950 |
| Example 7 | Compound (160) | 8.5 | 16.2 | 800 |
| Example 8 | Compound (194) | 8.6 | 16.0 | 1,100 |
| Comparative Example 7 | (HT) | 9.1 | 5.5 | 420 |

Table 2 above shows that each of the examples has a lower driving voltage, higher efficiency, and a longer lifetime than those of Comparative Example 7.

INDUSTRIAL APPLICABILITY

As described above in detail, the utilization of the material for an organic electroluminescence device of the present invention can provide an organic EL device which shows a low driving voltage, and high luminous efficiency, and has a long lifetime. Accordingly, the organic EL device of the present invention is extremely useful as, for example, a display and a light source for various electronic instruments.

The invention claimed is:

1. A material represented by formula (1):

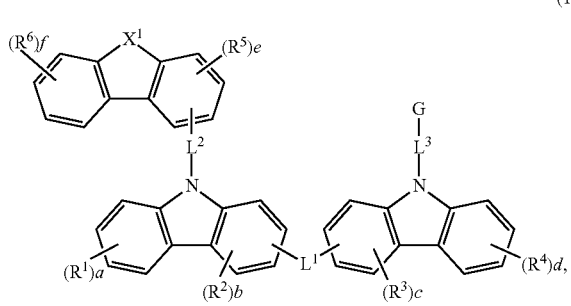

(1)

wherein:
G represents a substituted or unsubstituted aryl group having 6 to 18 ring carbon atoms, or formula (A):

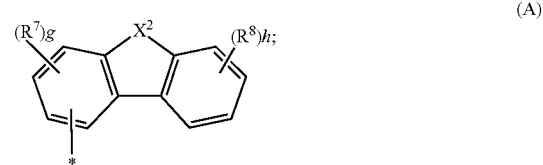

(A)

* represents a bond to $L^3$;
$X^1$ represents a sulfur atom or N—$R^9$;
$X^2$ represents a sulfur atom or N—$R^{10}$;
provided that, when $X^1$ represents a sulfur atom, G represents a substituted or unsubstituted aryl group having 6 to 18 ring carbon atoms;
and, when $X^1$ represents N—$R^9$; G represents a substituted or unsubstituted aryl group having 6 to 18 ring carbon atoms or formula (A);
$R^1$ to $R^8$ each independently represent a substituted or unsubstituted alkyl group having 1 to 5 carbon atoms, or a substituted or unsubstituted aryl group having 6 to 18 ring carbon atoms, such that alkyl groups represented by $R^1$ to $R^8$ optionally form a ring;
when G and $R^1$ to $R^8$ have substituents, the substituents R's each independently represent an alkyl group having 1 to 5 carbon atoms, or an aryl group having 6 to 18 ring carbon atoms;
a, d, and f each independently represent an integer of any one of 0 to 4, and b, c, and e represent 0, such that a relationship of 0≤(a+b+c+d+e+f)≤4 is established;
$R^9$ and $R^{10}$ each independently represent an alkyl group having 1 to 5 carbon atoms, a phenyl group, a toluyl group, a dimethylphenyl group, a trimethylphenyl group, or a biphenyl group;
g represents 0, and h represents an integer of any one of 0 to 4, such that a relationship of 0≤(g+h)≤4 is established;
provided that when $X^1$ and $X^2$ each represent nitrogen, and the substituent $R^9$ represents a phenyl group, a case where the substituent $R^{10}$ represents a phenyl group is excluded;
$L^1$ represents a single bond, a divalent linking group including N, a divalent linking group including O, a divalent linking group including Si, a divalent linking group including P, a divalent linking group including S, or an alkylene group having 1 to 5 carbon atoms; and
$L^2$ and $L^3$ represent a single bond.

2. The material according to claim 1, wherein in the formula (1), $X^1$ represents N—$R^9$ and G represents the formula (A) where the $X^2$ represents a sulfur atom.

3. The material according to claim 1, wherein:
the formula (1) is represented by formula (2):

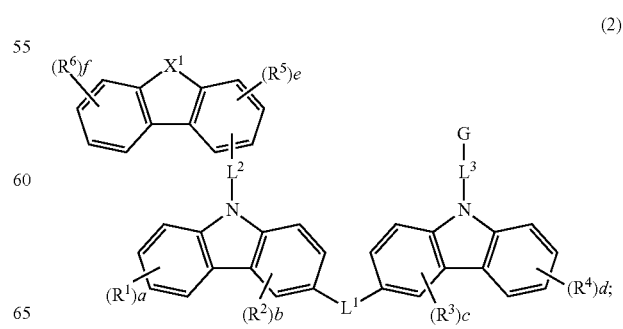

(2)

G represents a substituted or unsubstituted aryl group having 6 to 18 ring carbon atoms, or formula (A):

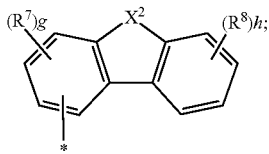

(A)

* represents a bond to $L^3$;
$X^1$ represents a sulfur atom or N—$R^9$;
$X^2$ represents a sulfur atom or N—$R^{10}$;
provided that, when $X^1$ represents a sulfur atom, G represents a substituted or unsubstituted aryl group having 6 to 18 ring carbon atoms;
and, when $X^1$ represents N—$R^9$; G represents a substituted or unsubstituted aryl group having 6 to 18 ring carbon atoms or formula (A);
$R^1$ to $R^8$ each independently represent a substituted or unsubstituted alkyl group having 1 to 5 carbon atoms, or a substituted or unsubstituted aryl group having 6 to 18 ring carbon atoms, such that alkyl groups represented by $R^1$ to $R^8$ optionally form a ring;
when G and $R^1$ to $R^8$ have substituents, the substituents R's each independently represent an alkyl group having 1 to 5 carbon atoms, or an aryl group having 6 to 18 ring carbon atoms;
a, d, and f each independently represent an integer of any one of 0 to 4, and b, c, and e represent 0, such that a relationship of 0≤(a+b+c+d+e+f)≤4 is established;
$R^9$ and $R^{10}$ each independently represent an alkyl group having 1 to 5 carbon atoms, a phenyl group, a toluyl group, a dimethylphenyl group, a trimethylphenyl group, or a biphenyl group;
g represents 0, and h represents an integer of any one of 0 to 4, such that a relationship of 0≤(g+h)≤4 is established;
provided that when $X^1$ and $X^2$ each represent nitrogen, and the substituent $R^9$ represents a phenyl group, a case where the substituent $R^{10}$ represents a phenyl group is excluded;
$L^1$ represents a single bond, a divalent linking group including N, a divalent linking group including O, a divalent linking group including Si, a divalent linking group including P, a divalent linking group including S, or an alkylene group having 1 to 5 carbon atoms; and
$L^2$ and $L^3$ represent a single bond.

4. The material according to claim 1, wherein:
the formula (1) is represented by formula (3):

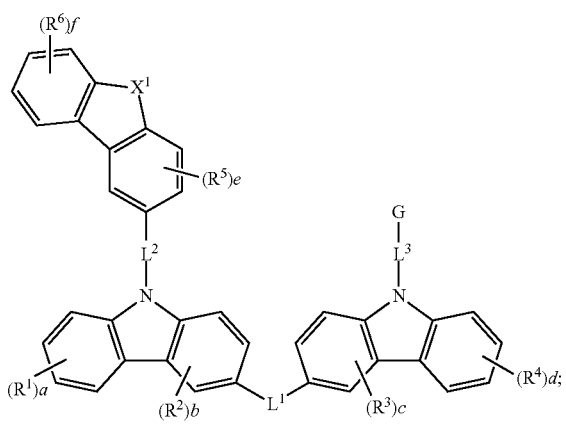

(3)

$R^1$, $R^4$, and $R^6$ each independently represent an aryl group having 6 to 18 ring carbon atoms, and the aryl group is optionally further substituted with the substituent R;
G represents a substituted or unsubstituted aryl group having 6 to 18 ring carbon atoms, or formula (A):

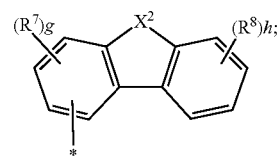

(A)

* represents a bond to $L^3$;
$X^1$ represents a sulfur atom or N—$R^9$;
$X^2$ represents a sulfur atom or N—$R^{10}$;
provided that, when $X^1$ represents a sulfur atom, G represents a substituted or unsubstituted aryl group having 6 to 18 ring carbon atoms;
and, when $X^1$ represents N—$R^9$; G represents a substituted or unsubstituted aryl group having 6 to 18 ring carbon atoms or formula (A);
$R^1$, $R^2$, $R^3$, $R^5$, $R^7$ and $R^8$ each independently represent a substituted or unsubstituted alkyl group having 1 to 5 carbon atoms, or a substituted or unsubstituted aryl group having 6 to 18 ring carbon atoms, such that alkyl groups represented by $R^1$ to $R^8$ optionally form a ring;
when G and $R^1$ to $R^8$ have substituents, the substituents R's each independently represent an alkyl group having 1 to 5 carbon atoms, or an aryl group having 6 to 18 ring carbon atoms;
a, d, and f each independently represent an integer of any one of 0 to 4, and b, c, and e represent 0, such that a relationship of 0≤(a+b+c+d+e+f)≤4 is established;
$R^9$ and $R^{10}$ each independently represent an alkyl group having 1 to 5 carbon atoms, a phenyl group, a toluyl group, a dimethylphenyl group, a trimethylphenyl group, or a biphenyl group;
g represents 0, and h represents an integer of any one of 0 to 4, such that a relationship of 0≤(g+h)≤4 is established;
provided that when $X^1$ and $X^2$ each represent nitrogen, and the substituent $R^9$ represents a phenyl group, a case where the substituent $R^{10}$ represents a phenyl group is excluded;
$L^1$ represents a single bond, a divalent linking group including N, a divalent linking group including O, a divalent linking group including Si, a divalent linking group including P, a divalent linking group including S, or an alkylene group having 1 to 5 carbon atoms; and
$L^2$ and $L^3$ represent a single bond.

5. The material according to claim 1, wherein in the formula (1), the $L^1$ represents one selected from the group consisting of a single bond, a divalent linking group including O, a divalent linking group including S, and an alkylene group having 1 to 5 carbon atoms.

6. The material according to claim 1, wherein the material has a molecular weight of 1,000 or less.

7. The material according to claim 1, wherein the material has a triplet energy of 2.70 eV or more.

8. The material according to claim 1, comprising any one of the following compounds:
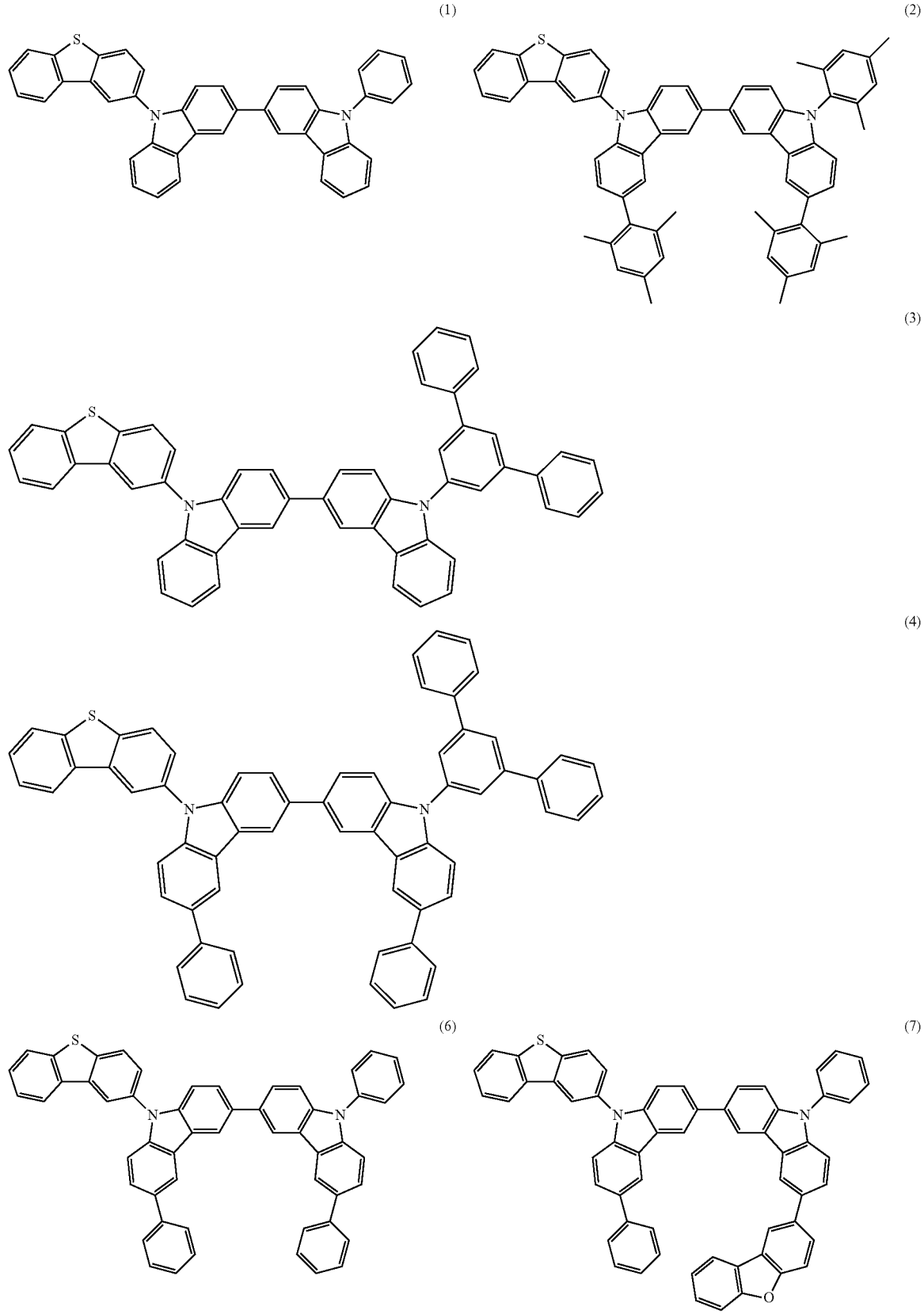

-continued
(8)
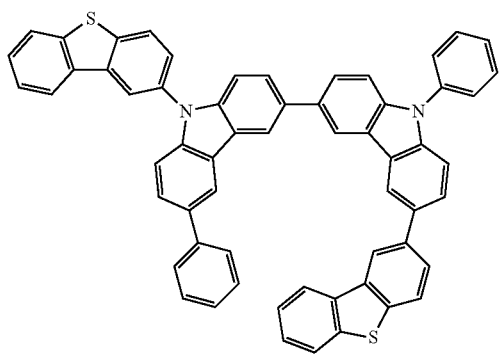
(9)
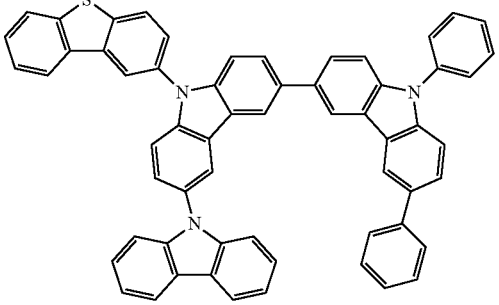
(14)
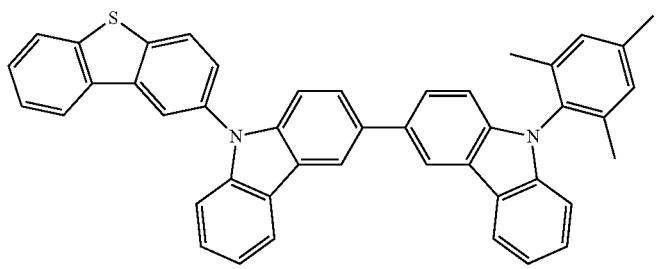
(22)
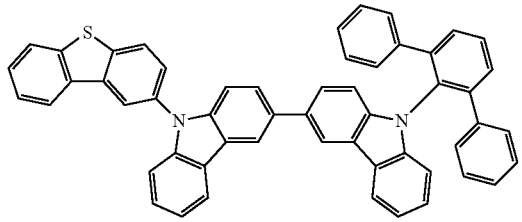
(23)
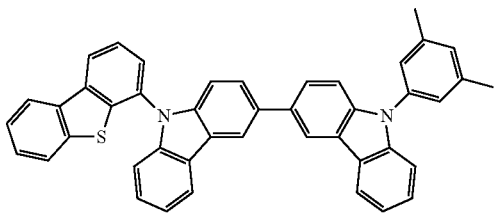
(30)
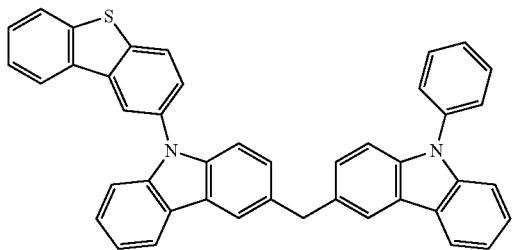
(31)
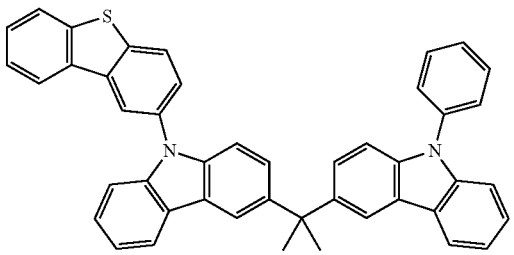
(35)
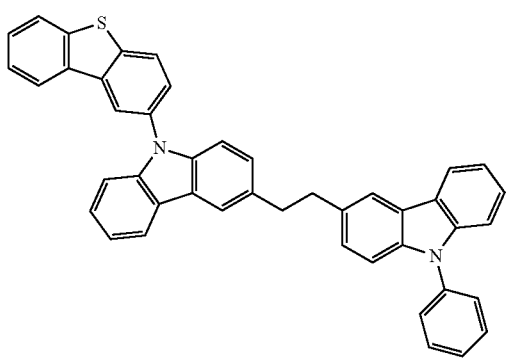
(32)
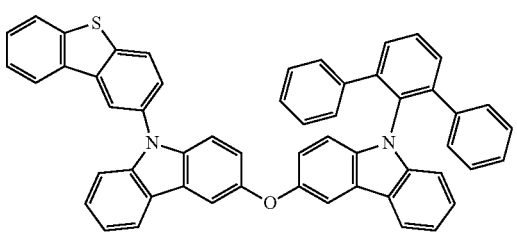

-continued
(36)
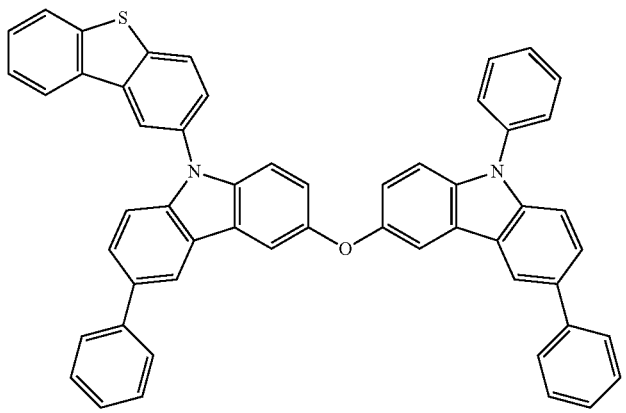
(38)
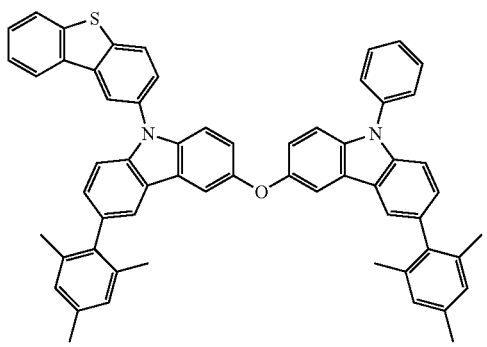
(39)
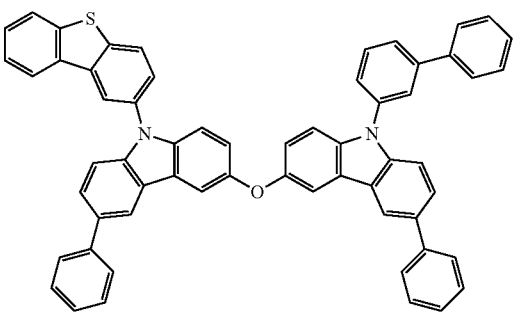
(42)
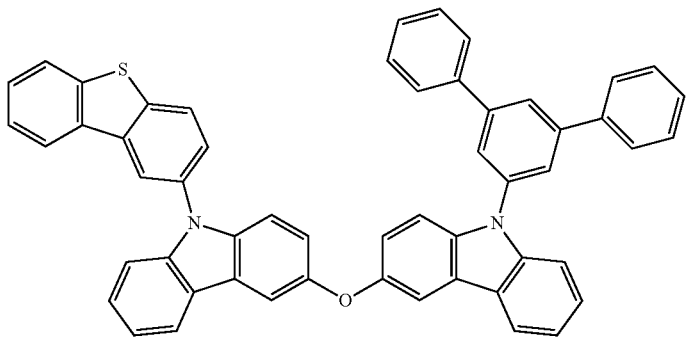
(46)
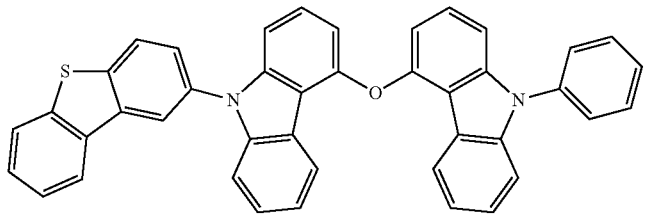
(49)
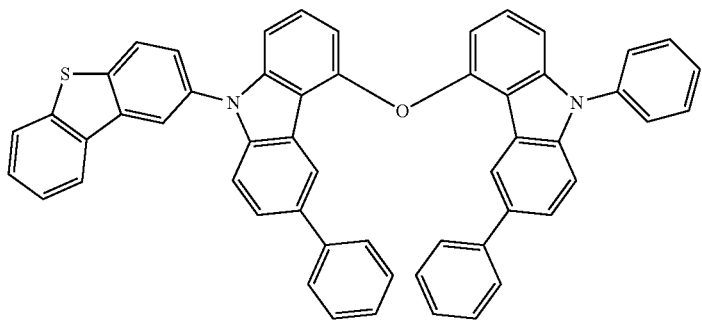

-continued
(51)
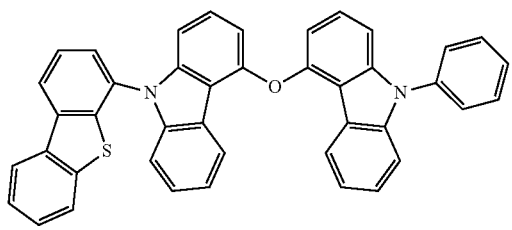
(52)
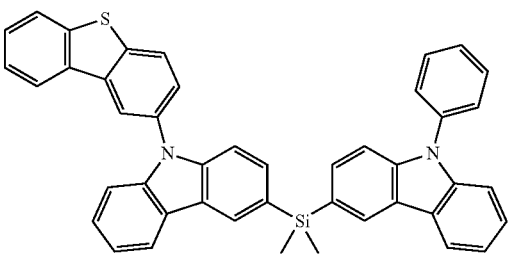
(53)
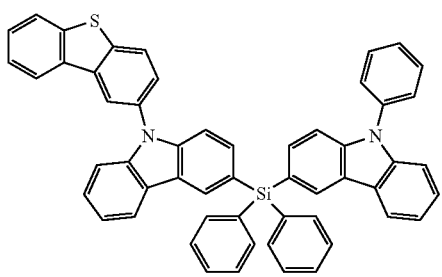
(54)
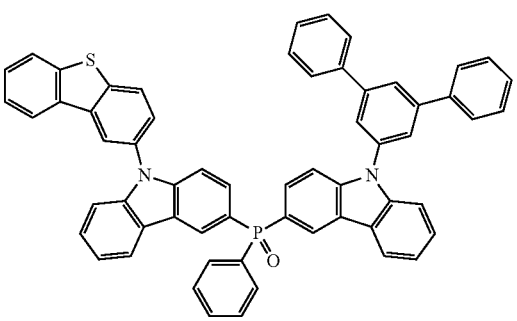
(56)
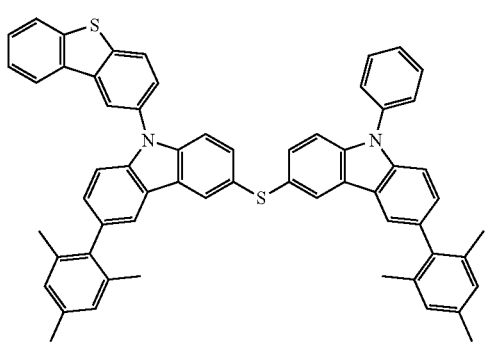
(57)
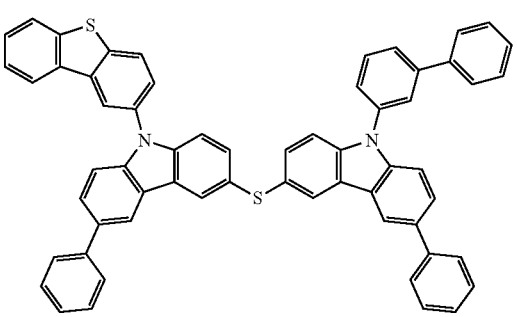
(60)
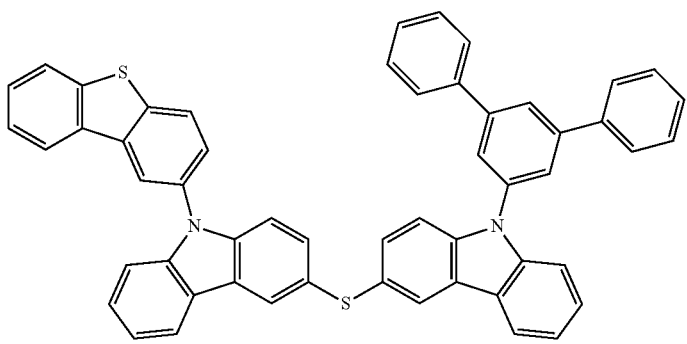
(64)
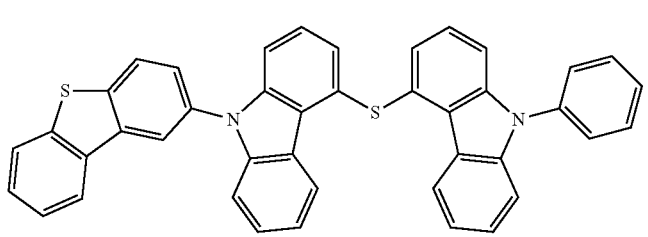

-continued
(67)
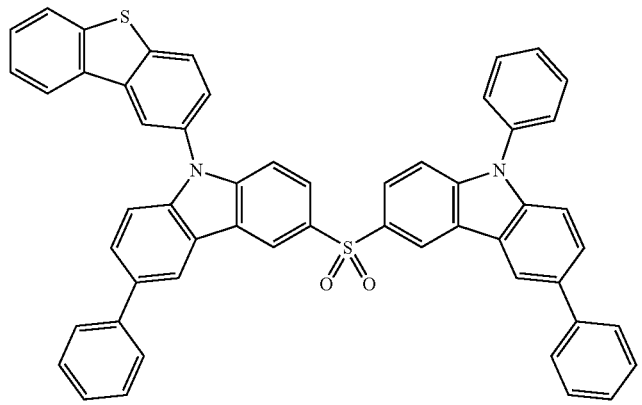
(104)
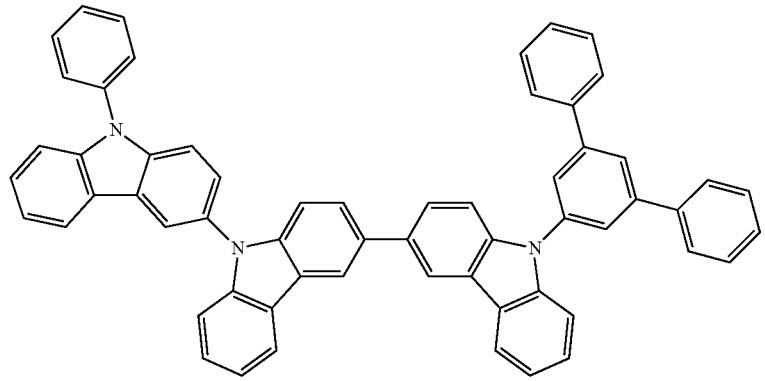
(105)
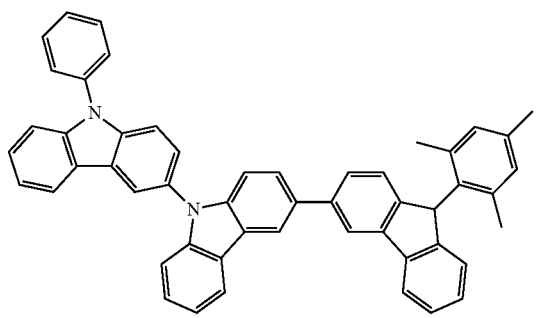
(106)
(107)
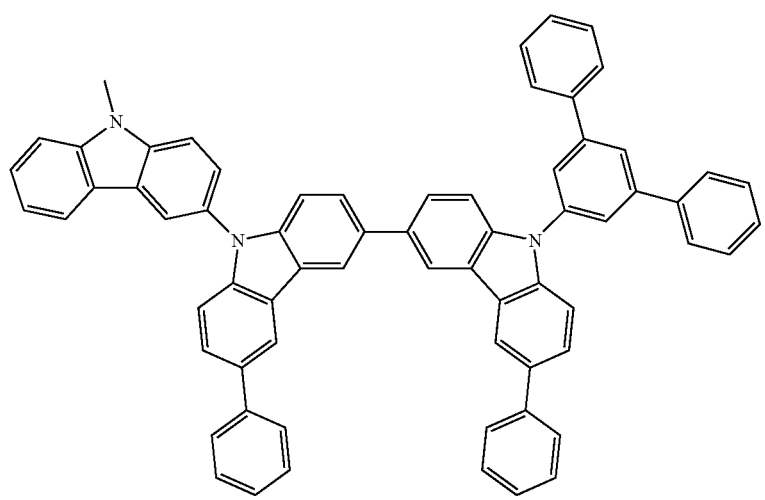

-continued
(108)
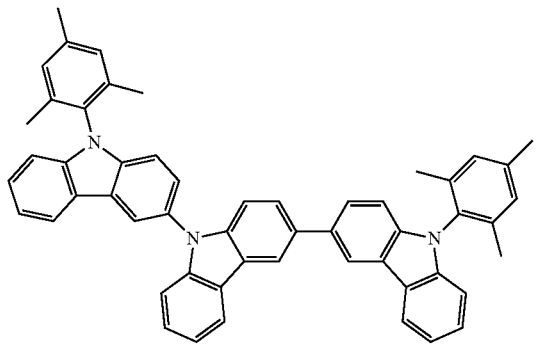
(109)
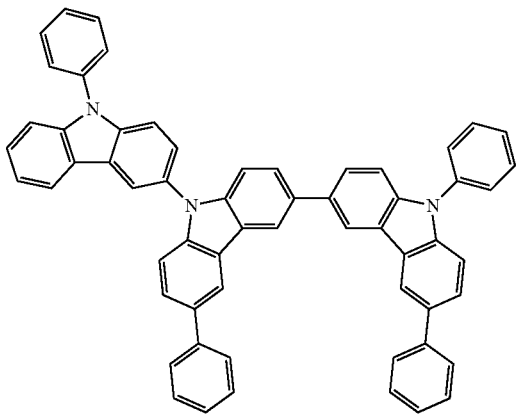
(111)
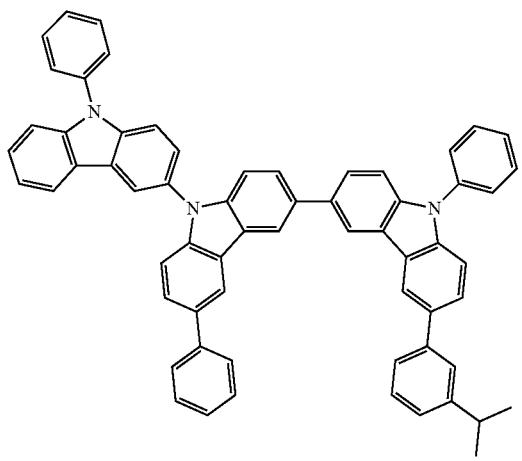
(114)
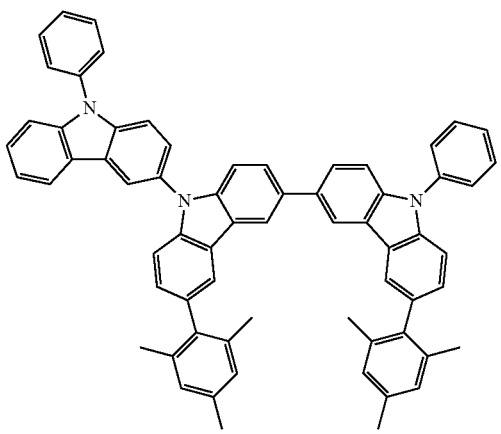
(115)
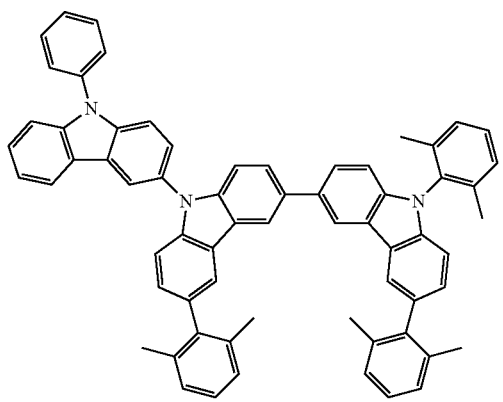
(116)
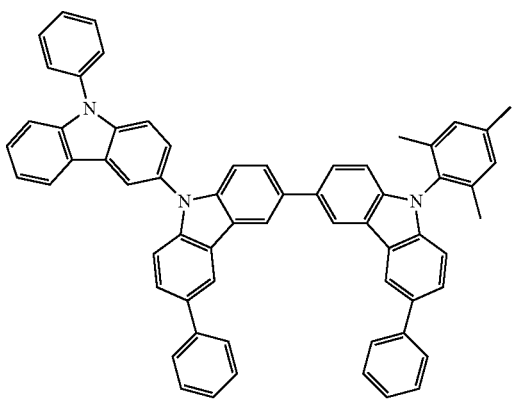

-continued
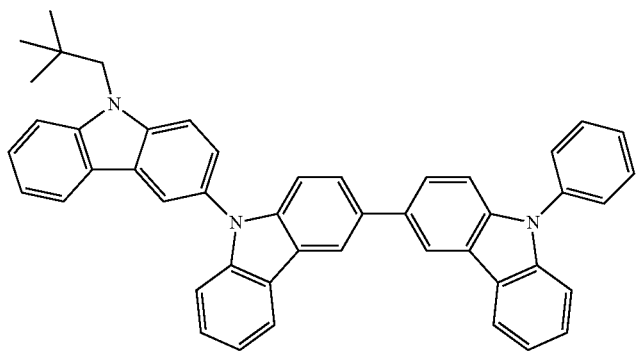
(117)
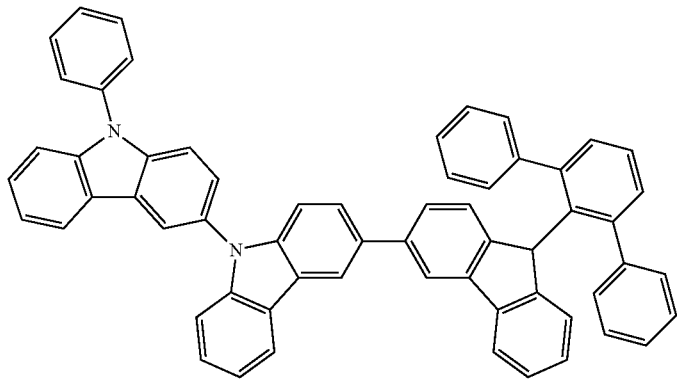
(120)
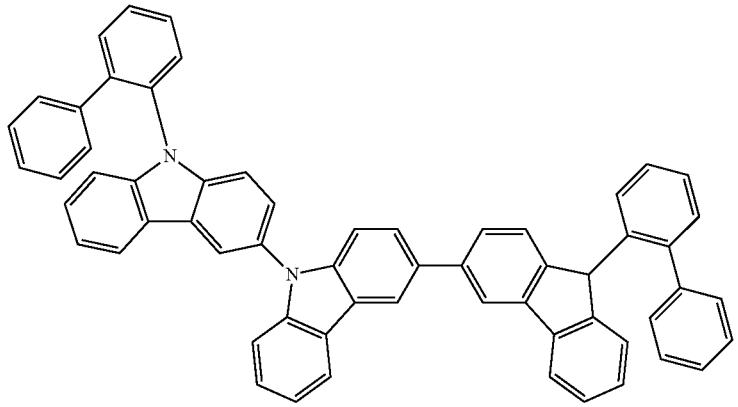
(121)
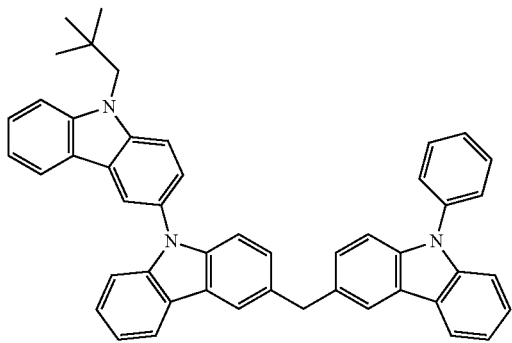
(127)
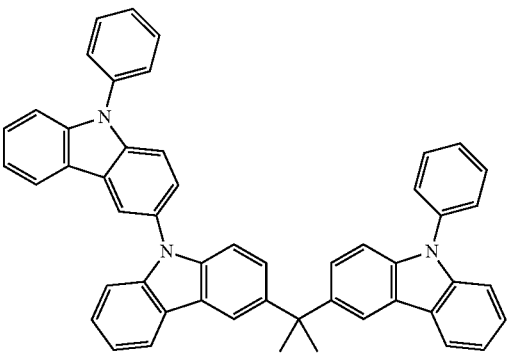
(128)

-continued
(129)
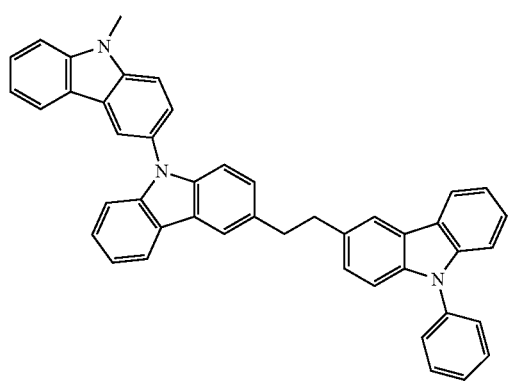
(132)
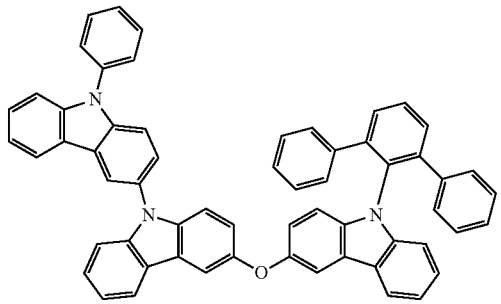
(133)
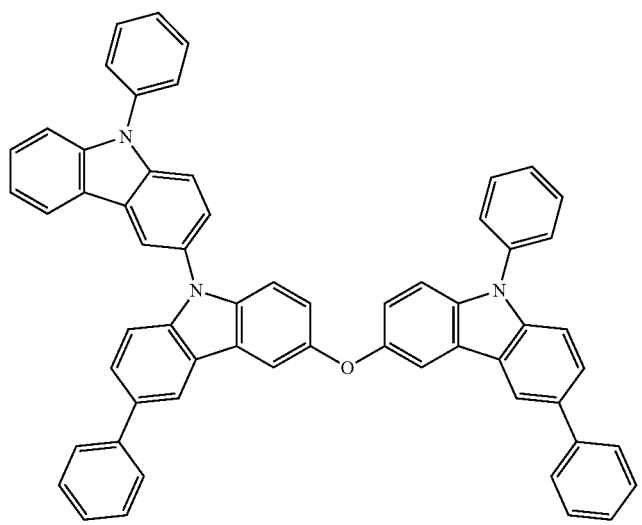
(135)
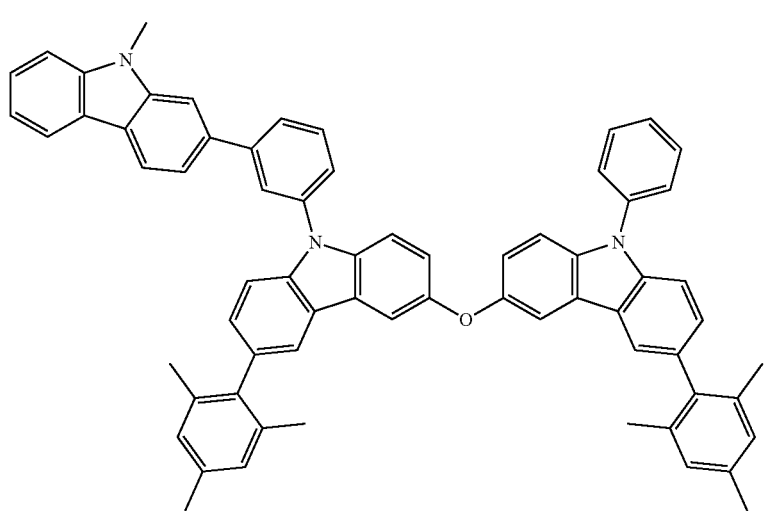

-continued
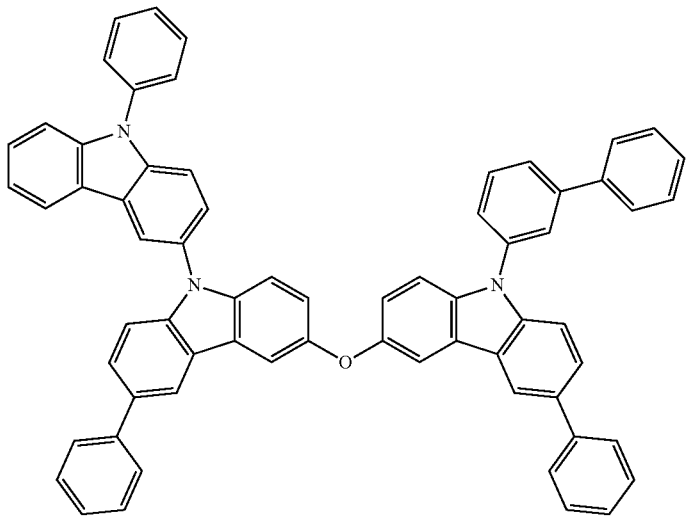
(136)
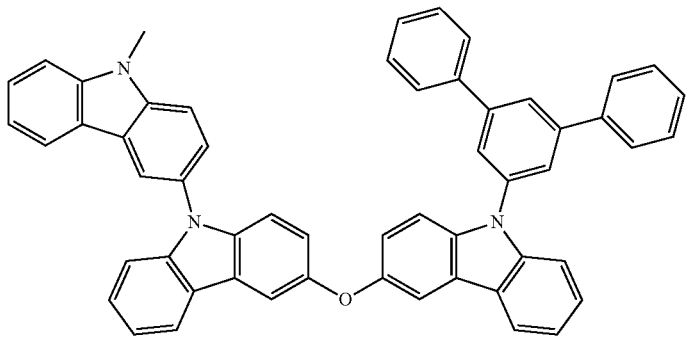
(139)
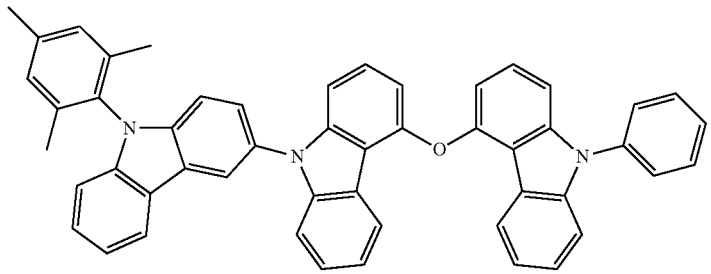
(143)
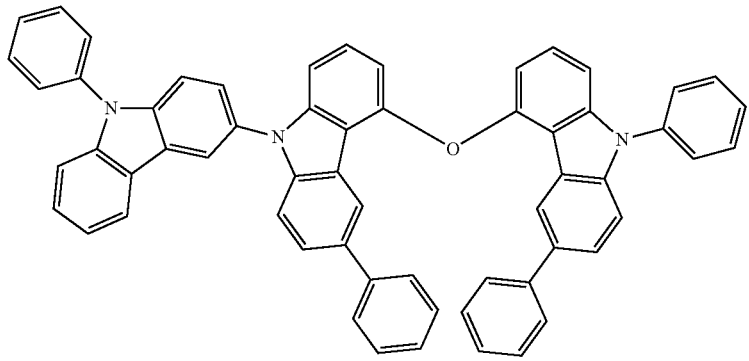
(145)

(146)
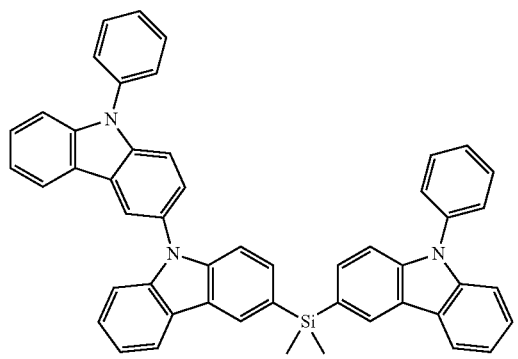
(147)
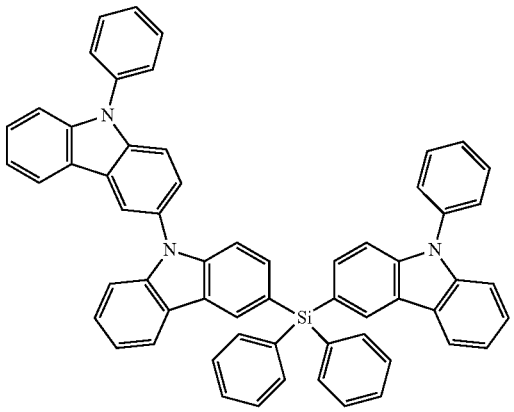
(148)
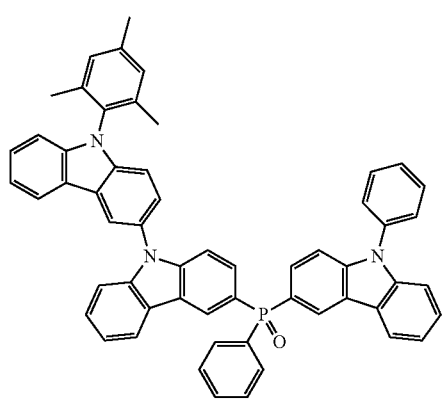
(150)
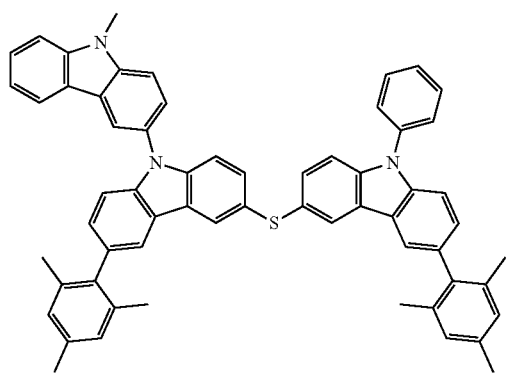
(151)
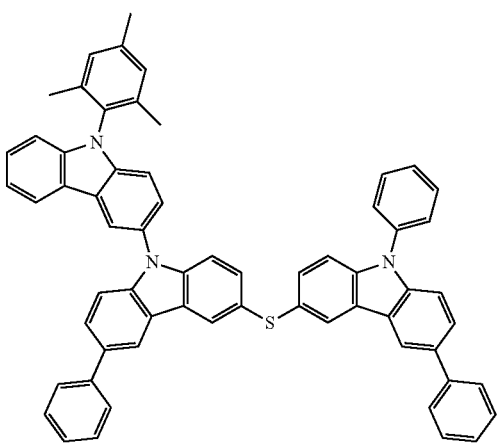

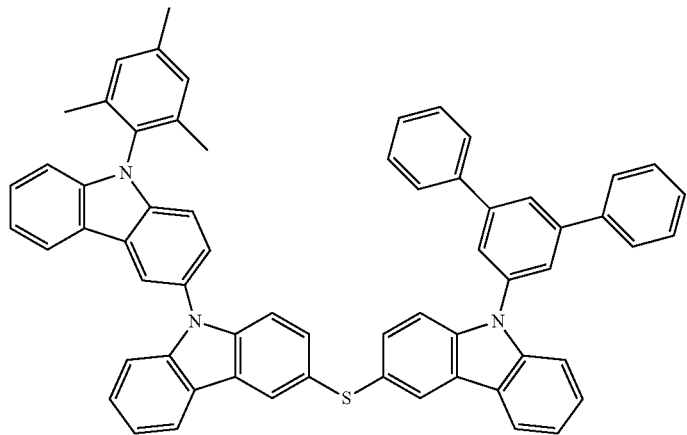
(153)
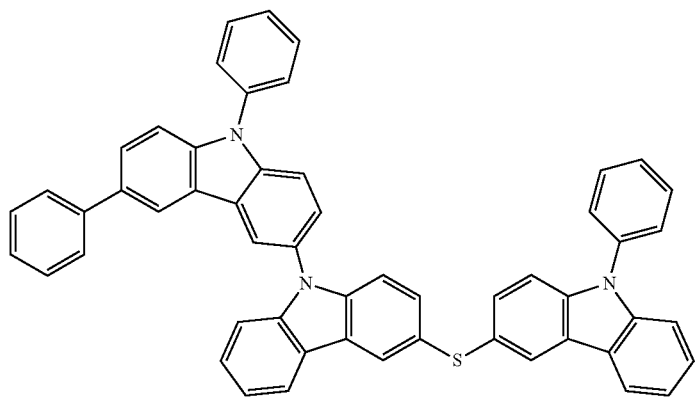
(154)
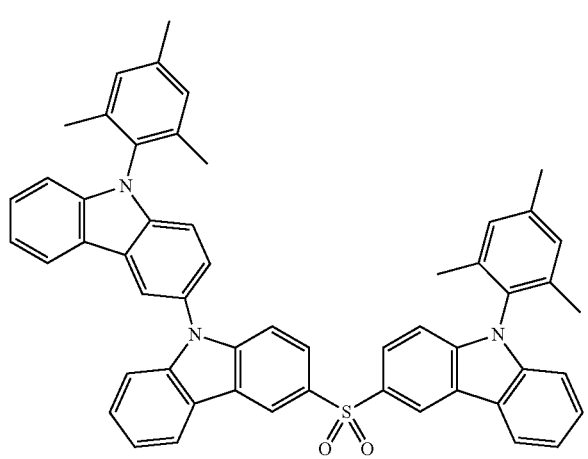
(156)

(158)
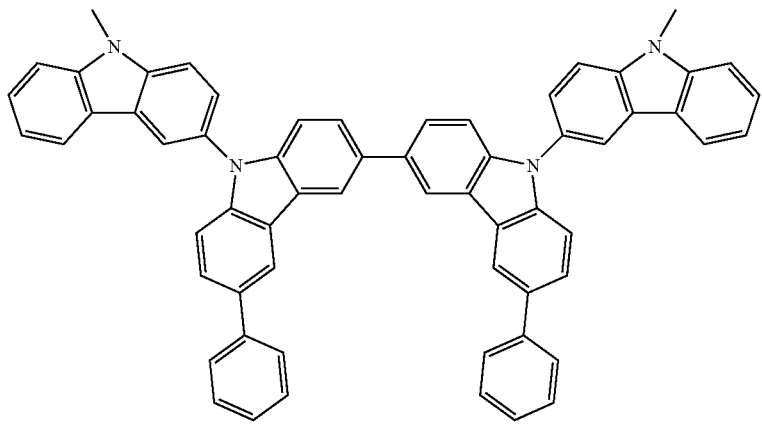
(159)
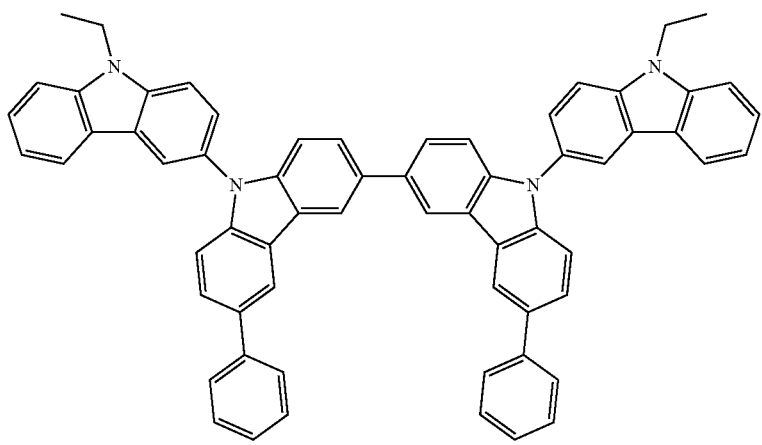
(160)
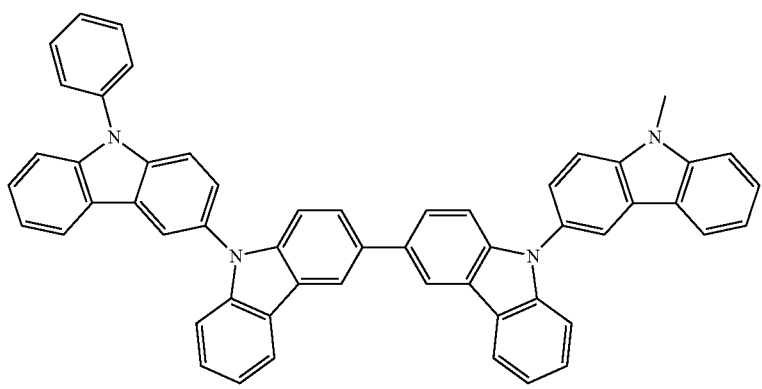
(161)
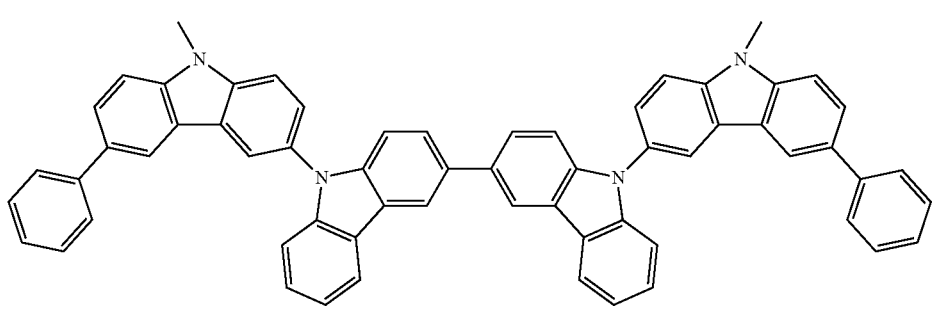

-continued
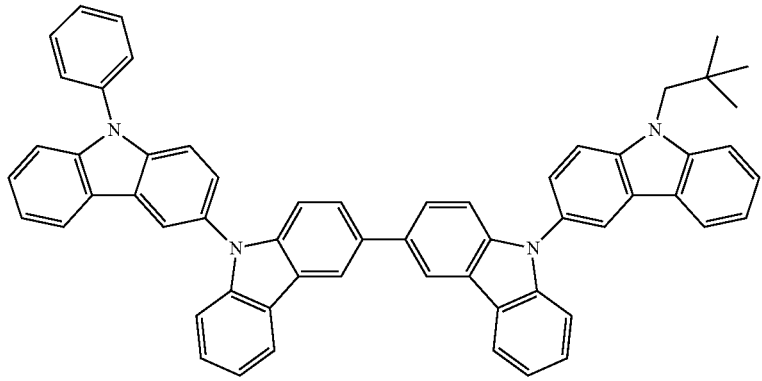
(162)
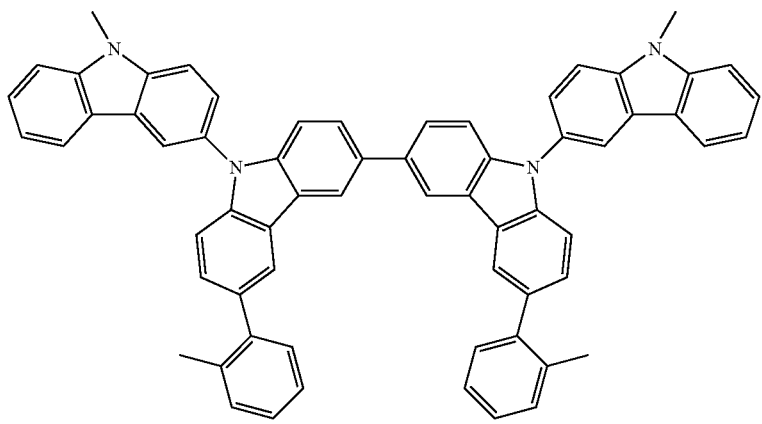
(168)
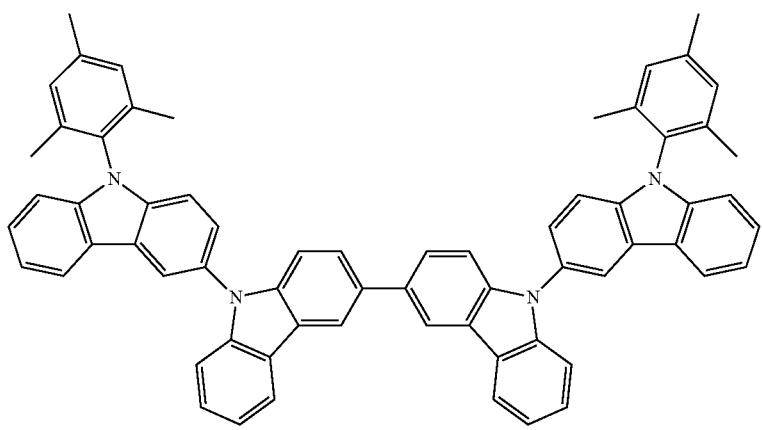
(169)
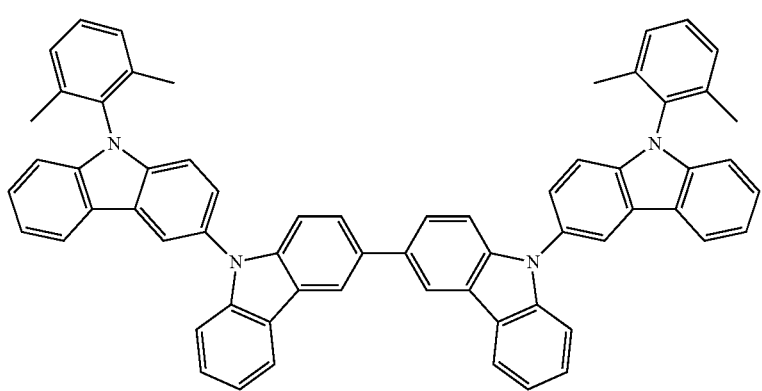
(170)

-continued
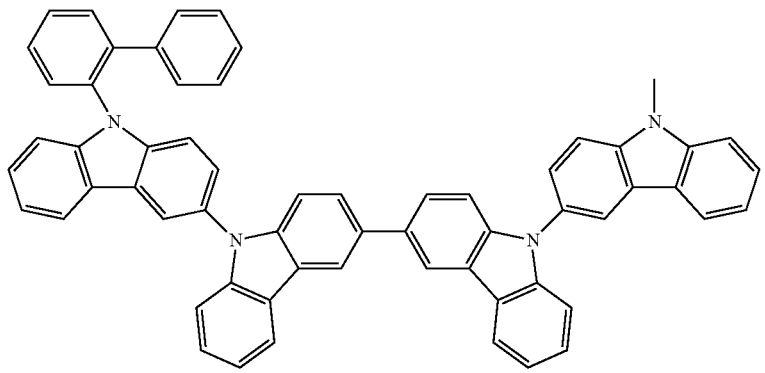
(171)
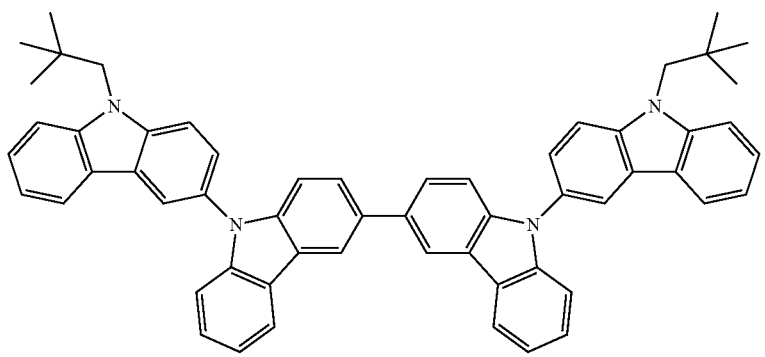
(172)
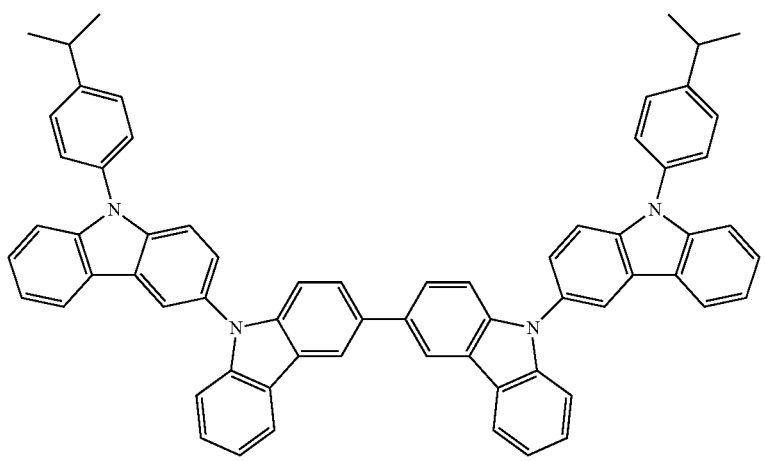
(173)
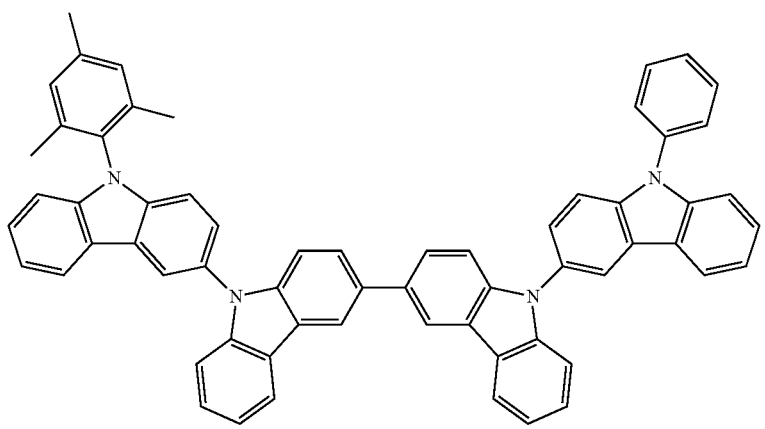
(174)

-continued
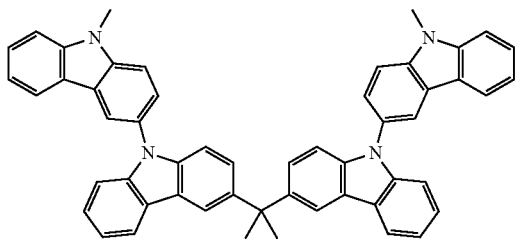
(175)
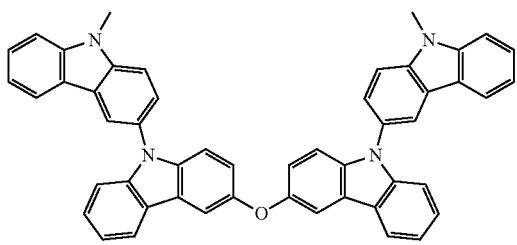
(177)
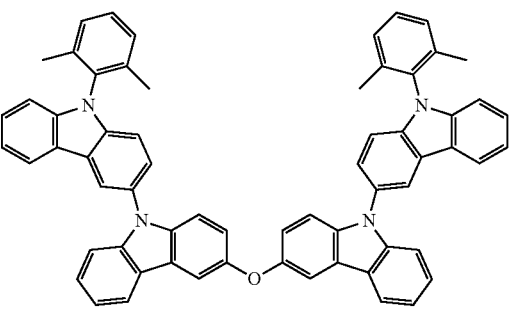
(178)
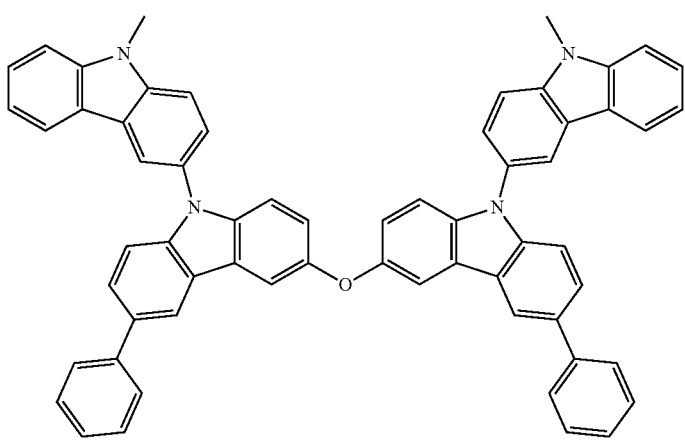
(179)
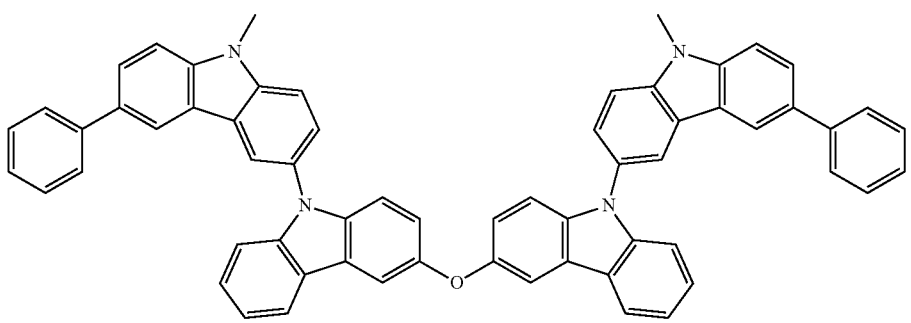
(180)
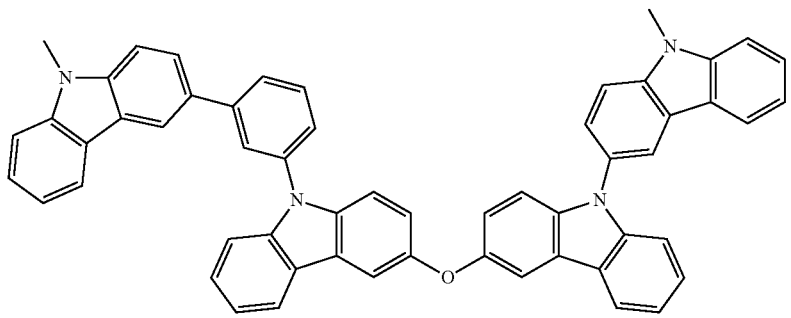
(181)

-continued
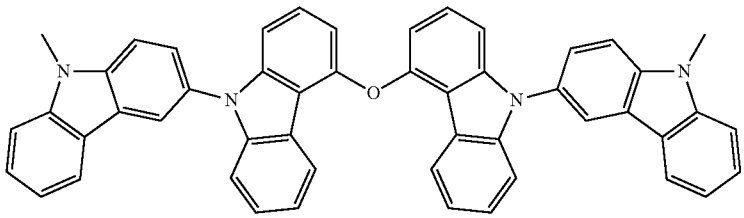
(183)
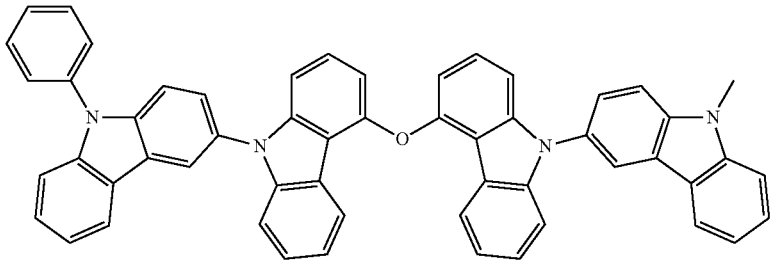
(184)
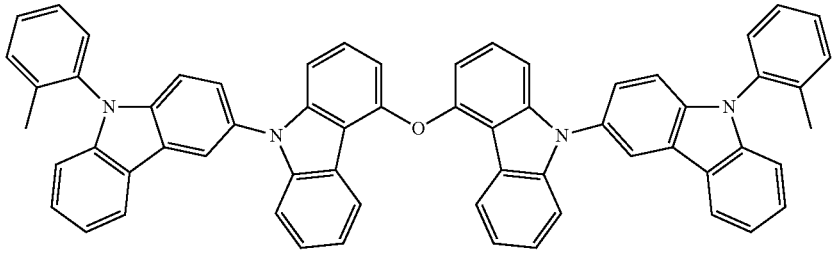
(185)
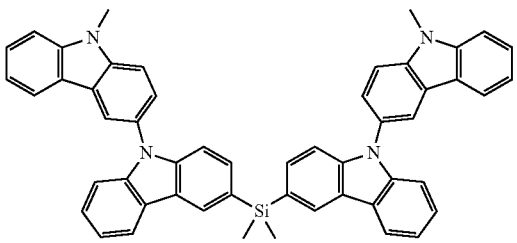
(187)
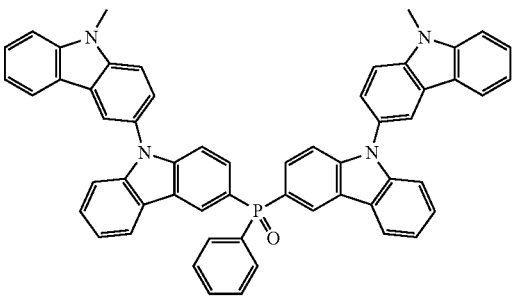
(188)
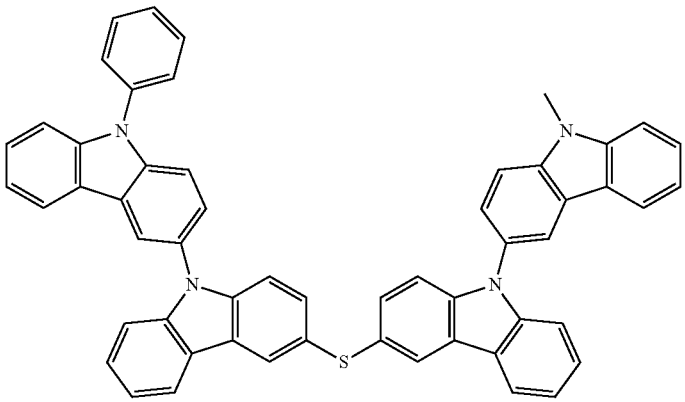
(190)

-continued
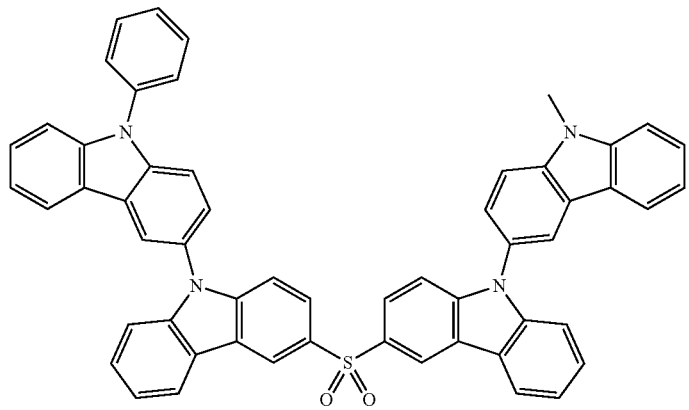
(192)
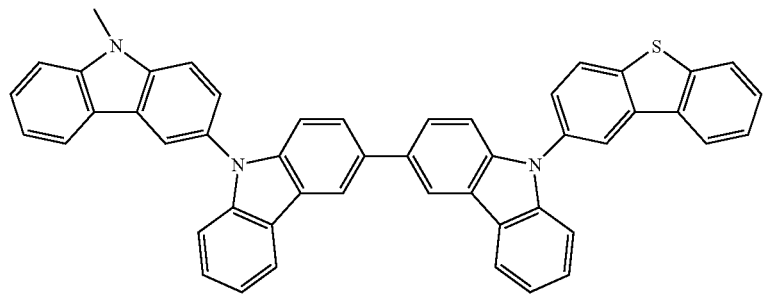
(193)
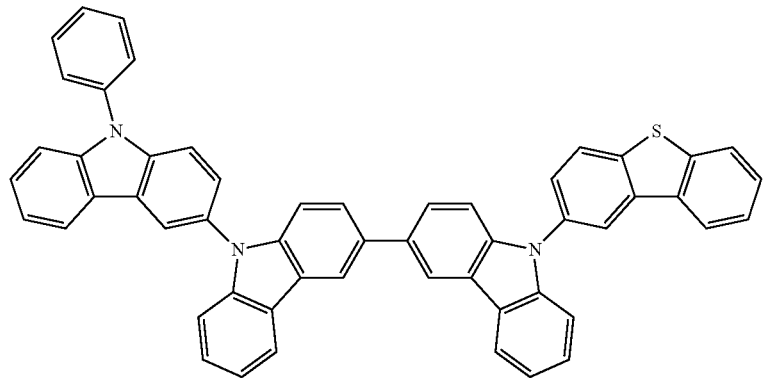
(194)
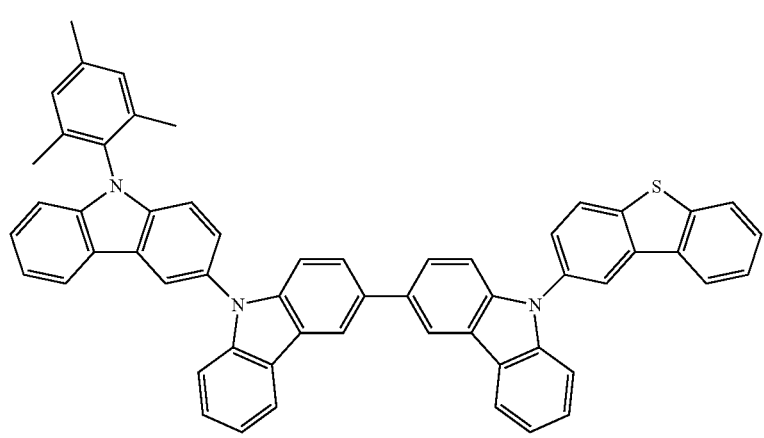
(195)

-continued
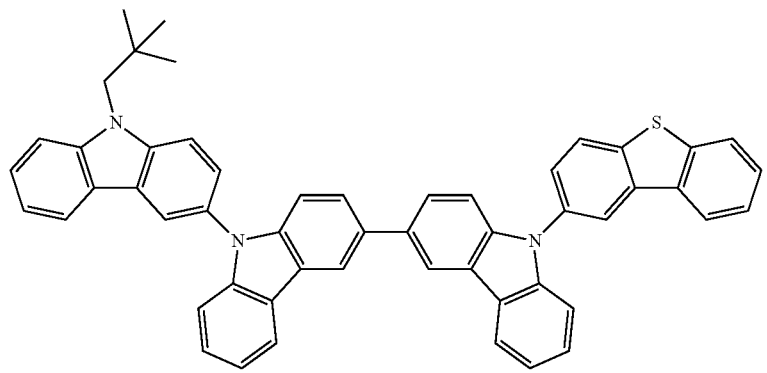
(196)
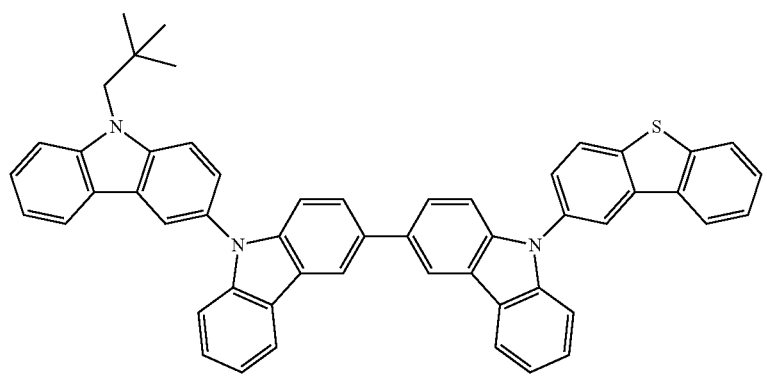
(196)
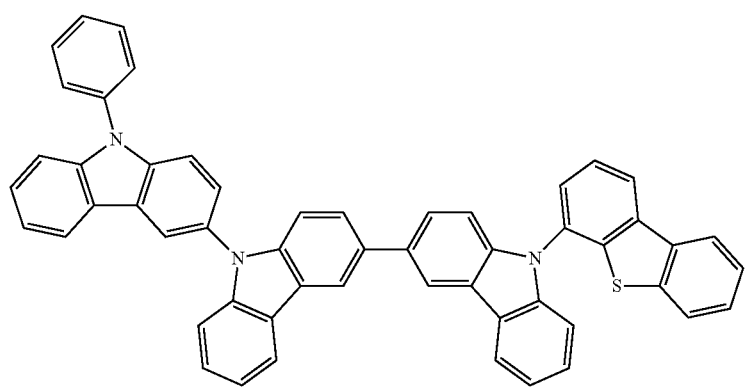
(198)
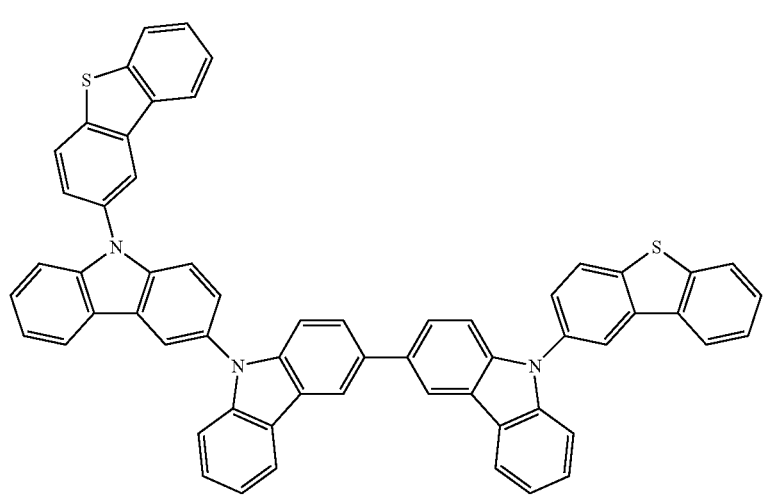
(199)

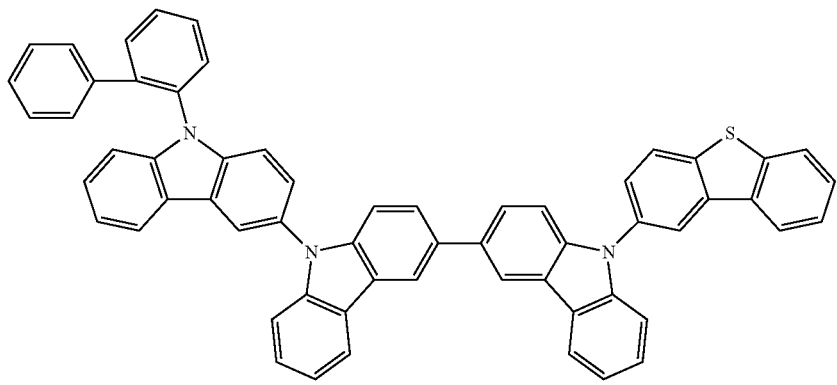
(200)
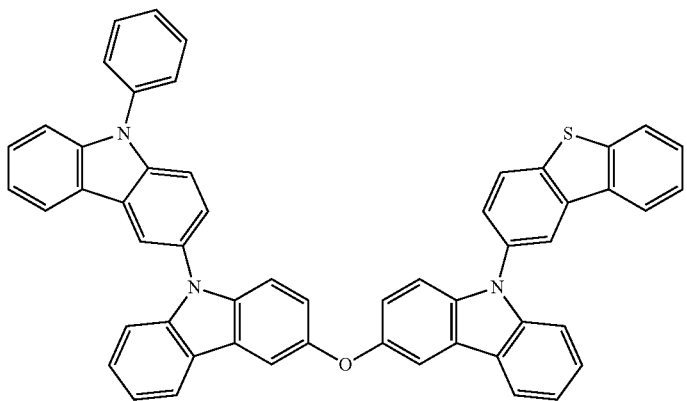
(201)
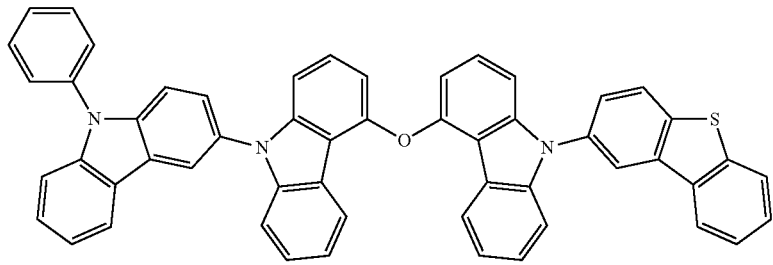
(202)
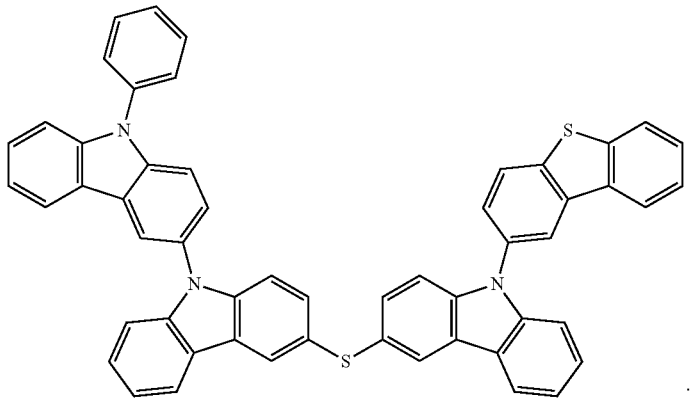
(203)

9. The material according to claim 1, wherein in the formula (1), f represents 0, and in the formula (A), h represents 0.

10. The material according to claim 1,
wherein in the formula (1), $X^1$ represents a sulfur atom, and
G represents a substituted or unsubstituted phenyl group, a substituted or unsubstituted o-biphenyl group, a substituted or unsubstituted m-biphenyl group, a substituted or unsubstituted p-biphenyl group, a substituted or unsubstituted o-terphenyl group, a substituted or unsubstituted m-terphenyl group, a substituted or unsubstituted p-terphenyl group, or a substituted or unsubstituted naphthyl group.

11. The material according to claim 1,
wherein in the formula (1), $X^1$ represents N—$R^9$, and
G represents a substituted or unsubstituted phenyl group, a substituted or unsubstituted o-biphenyl group, a substituted or unsubstituted m-biphenyl group, a substituted or unsubstituted p-biphenyl group, a substituted or unsubstituted o-terphenyl group, a substituted or unsubstituted m-terphenyl group, a substituted or unsubstituted p-terphenyl group, or a substituted or unsubstituted naphthyl group.

12. The material according to claim 1, wherein in the formula (1), $X^1$ represents N—$R^9$, and G represents the formula (A).

13. The material according to claim 1, wherein $R^1$ to $R^8$ each independently represent an unsubstituted alkyl group having 1 to 5 carbon atoms, or an unsubstituted aryl group having 6 to 18 ring carbon atoms.

14. The material according to claim 1, wherein $R^1$ to $R^8$ each independently represent a methyl group, an ethyl group, a propyl group, an isopropyl group, a n-butyl group, a s-butyl group, an isobutyl group, a t-butyl group, a phenyl group, an o-biphenyl group, a m-biphenyl group, a p-biphenyl group, or a naphthyl group.

15. The material according to claim 1, wherein when G and $R^1$ to $R^8$ have substituents, the substituents R's each independently represent a methyl group, an ethyl group, a propyl group, an isopropyl group, a n-butyl group, a s-butyl group, an isobutyl group, a t-butyl group, a phenyl group, an o-biphenyl group, a m-biphenyl group, a p-biphenyl group, or a naphthyl group.

16. The material according to claim 1, wherein $R^9$ and $R^{10}$ each independently represent a methyl group, an ethyl group, a propyl group, an isopropyl group, a n-butyl group, a s-butyl group, an isobutyl group, a t-butyl group, a phenyl group, or a biphenyl group.

17. The material according to claim 1, wherein $L^1$ represents a single bond.

18. An organic electroluminescence device, comprising an organic thin film layer comprising a light emitting layer between a cathode and an anode, wherein at least one organic film layer comprises the material according to claim 1.

19. The organic electroluminescence device according to claim 18, wherein the material for an organic electroluminescence device is incorporated into the light emitting layer.

20. The organic electroluminescence device according to claim 19, wherein the material for an organic electroluminescence device is incorporated as a host material for the light emitting layer.

21. The organic electroluminescence device according to claim 20, wherein the light emitting layer comprises a phosphorescent light emitting material.

22. The organic electroluminescence device according to claim 21, wherein the phosphorescent light emitting material comprises a compound comprising a metal selected from the group consisting of iridium (Ir), osmium (Os), and platinum (Pt).

23. The organic electroluminescence device according to claim 22, wherein the compound comprises an orthometallated metal complex.

24. The organic electroluminescence device according to claim 18, further comprising a reducing dopant at an interfacial region between the cathode and the organic thin film layer.

25. The organic electroluminescence device according to claim 18, wherein at least one organic thin film layer comprises an electron injecting layer provided between the light emitting layer and the cathode, and the electron injecting layer comprises a nitrogen-containing ring derivative.

26. The organic electroluminescence device according to claim 18, wherein at least one organic thin film layer comprises a hole transporting layer provided between the light emitting layer and the anode, and the hole transporting layer comprises the material for an organic electroluminescence device.

* * * * *